(12) United States Patent
Rajasekaran et al.

(10) Patent No.: US 10,486,129 B2
(45) Date of Patent: Nov. 26, 2019

(54) SUBSTRATES, PEPTIDE ARRAYS, AND METHODS

(71) Applicant: Vibrant Holdings, LLC, Hillsborough, CA (US)

(72) Inventors: John J. Rajasekaran, Hillsborough, CA (US); Vasanth Jayaraman, San Mateo, CA (US); Tianhao Wang, San Mateo, CA (US); Kang Bei, San Mateo, CA (US); Hari Krishnan Krishnamurthy, San Mateo, CA (US)

(73) Assignee: Vibrant Holdings, LLC, San Carlos, CA (US)

( * ) Notice: Subject to any disclaimer, the term of this patent is extended or adjusted under 35 U.S.C. 154(b) by 568 days.

(21) Appl. No.: 14/941,404

(22) Filed: Nov. 13, 2015

(65) Prior Publication Data
US 2016/0067667 A1  Mar. 10, 2016

Related U.S. Application Data

(60) Division of application No. 14/454,554, filed on Aug. 7, 2014, now Pat. No. 9,216,399, which is a
(Continued)

(51) Int. Cl.
*C40B 60/14* (2006.01)
*B01J 19/00* (2006.01)
(Continued)

(52) U.S. Cl.
CPC .......... *B01J 19/0046* (2013.01); *C07K 1/047* (2013.01); *G01N 33/54353* (2013.01);
(Continued)

(58) Field of Classification Search
None
See application file for complete search history.

(56) References Cited

U.S. PATENT DOCUMENTS 5,143,854 A   9/1992 Pirrung et al.
5,240,811 A   8/1993 Taylor et al.
(Continued)

FOREIGN PATENT DOCUMENTS

JP   H05-294995 A   11/1993
JP   H06-500308 A   1/1994
(Continued)

OTHER PUBLICATIONS

Piehler et al. (Jul. 1999) Colloids and Surfaces B Biointerfaces vol. 13 pp. 325 to 336.*
(Continued)

*Primary Examiner* — Christian C Boesen
(74) *Attorney, Agent, or Firm* — Goodwin Procter LLP

(57) ABSTRACT

Disclosed herein are formulations, substrates, and arrays. Also disclosed herein are methods for manufacturing and using the formulations, substrates, and arrays. Also disclosed are methods for identifying peptide sequences useful for diagnosis and treatment of disorders, and methods for using the peptide sequences for diagnosis and treatment of disorders, e.g., celiac disorder. In certain embodiments, substrates and arrays comprise a porous layer for synthesis and attachment of polymers or biomolecules.

1 Claim, 40 Drawing Sheets
Specification includes a Sequence Listing.

Related U.S. Application Data continuation of application No. PCT/US2013/025190, filed on Feb. 7, 2013.

(60) Provisional application No. 61/595,908, filed on Feb. 7, 2012, provisional application No. 61/595,988, filed on Feb. 7, 2012, provisional application No. 61/608,554, filed on Mar. 8, 2012, provisional application No. 61/609,003, filed on Mar. 9, 2012, provisional application No. 61/665,489, filed on Jun. 28, 2012, provisional application No. 61/726,515, filed on Nov. 14, 2012, provisional application No. 61/761,347, filed on Feb. 6, 2013.

(51) Int. Cl.
  *G01N 33/543* (2006.01)
  *C07K 1/04* (2006.01)
  *C40B 40/10* (2006.01)

(52) U.S. Cl.
  CPC .......... *B01J 2219/00432* (2013.01); *B01J 2219/00596* (2013.01); *B01J 2219/00621* (2013.01); *B01J 2219/00639* (2013.01); *B01J 2219/00659* (2013.01); *B01J 2219/00711* (2013.01); *B01J 2219/00725* (2013.01); *C40B 40/10* (2013.01); *C40B 60/14* (2013.01); *G01N 2800/00* (2013.01)

(56) References Cited

U.S. PATENT DOCUMENTS

| | | | |
|---|---|---|---|
| 5,310,687 A | 5/1994 | Bard et al. | |
| 5,866,434 A | 2/1999 | Massey et al. | |
| 5,919,523 A | 7/1999 | Sundberg et al. | |
| 6,017,696 A | 1/2000 | Heller | |
| 6,040,138 A | 3/2000 | Lockhart et al. | |
| 6,083,697 A | 7/2000 | Beecher et al. | |
| 6,140,045 A | 10/2000 | Wohlstadter et al. | |
| 6,319,726 B1 | 11/2001 | Schuppan et al. | |
| 6,506,558 B1 | 1/2003 | Fodor et al. | |
| 6,521,181 B1 | 2/2003 | Northrup et al. | |
| 6,943,034 B1 | 9/2005 | Winkler et al. | |
| 7,510,841 B2 | 3/2009 | Stuelpnagel et al. | |
| 7,544,638 B2 | 6/2009 | Gao et al. | |
| 8,128,908 B2 | 3/2012 | Santra et al. | |
| 9,417,236 B2 | 8/2016 | Rajasekaran et al. | |
| 2002/0086319 A1* | 7/2002 | Ellson .............. | B01J 19/0046 435/6.11 |
| 2003/0068446 A1 | 4/2003 | Mirkin et al. | |
| 2003/0124029 A1 | 7/2003 | Webb et al. | |
| 2003/0148401 A1 | 8/2003 | Agrawal et al. | |
| 2003/0228605 A1 | 12/2003 | Sloostra et al. | |
| 2005/0221351 A1 | 10/2005 | Ryu | |
| 2005/0244863 A1 | 11/2005 | Mir | |
| 2005/0260611 A1 | 11/2005 | Wang et al. | |
| 2006/0088863 A1 | 4/2006 | Yamamoto et al. | |
| 2006/0172340 A1 | 8/2006 | Wohlstadter et al. | |
| 2007/0122841 A1 | 5/2007 | Rajasekaran et al. | |
| 2007/0122842 A1 | 5/2007 | Rajasekaran et al. | |
| 2007/0154946 A1 | 7/2007 | Rajasekaran et al. | |
| 2007/0231794 A1 | 10/2007 | Dill et al. | |
| 2008/0108149 A1 | 5/2008 | Sundararajan et al. | |
| 2009/0311727 A1 | 12/2009 | Watkins et al. | |
| 2009/0325816 A1 | 12/2009 | Mirkin et al. | |
| 2010/0028559 A1 | 2/2010 | Yan et al. | |
| 2010/0093554 A1 | 4/2010 | Chu | |
| 2010/0120630 A1 | 5/2010 | Huang et al. | |
| 2010/0240555 A1 | 9/2010 | Sundararajan et al. | |
| 2011/0097762 A1 | 4/2011 | Gao et al. | |
| 2011/0190210 A1* | 8/2011 | Adini ............... | C07K 14/70596 514/15.6 |
| 2011/0281766 A1 | 11/2011 | Cooper | |
| 2011/0293644 A1 | 12/2011 | Anderson et al. | |
| 2012/0172309 A1 | 7/2012 | Dal Farra et al. | |
| 2012/0183981 A1 | 7/2012 | Norman et al. | |
| 2012/0245057 A1 | 9/2012 | Albert et al. | |
| 2014/0072963 A1 | 3/2014 | Qin | |

FOREIGN PATENT DOCUMENTS

| | | |
|---|---|---|
| JP | 2002-500362 A | 1/2002 |
| JP | 2002-502698 A | 1/2002 |
| JP | 2002-525577 A | 8/2002 |
| JP | 2003-517149 A | 5/2003 |
| JP | 2003-523348 A | 8/2003 |
| JP | 2003-03342354 A | 12/2003 |
| JP | 2005-512032 A | 4/2005 |
| JP | 2005-513999 A | 5/2005 |
| JP | 2005-521032 A | 7/2005 |
| JP | 2005-264156 A | 9/2005 |
| JP | 2005-530983 A | 10/2005 |
| JP | 2007-504462 A | 3/2007 |
| JP | 2008-170449 A | 7/2008 |
| JP | 2009-075131 A | 4/2009 |
| JP | 2009-534200 A | 9/2009 |
| JP | 2010-507099 A | 3/2010 |
| JP | 2010-215816 A | 9/2010 |
| JP | 2011-017711 A | 1/2011 |
| JP | 2011-519168 A | 6/2011 |
| JP | 2011-234723 A | 11/2011 |
| JP | 2012-163491 A | 8/2012 |
| JP | 2012-518294 A | 8/2012 |
| WO | WO 98/03872 A2 | 1/1998 |
| WO | WO 98/12539 A1 | 3/1998 |
| WO | WO 99/41007 A2 | 8/1999 |
| WO | WO 00/16089 A2 | 3/2000 |
| WO | WO 01/43870 A2 | 6/2001 |
| WO | WO 03/001889 A2 | 1/2003 |
| WO | WO 03/023360 A2 | 3/2003 |
| WO | WO 03/038033 A2 | 5/2003 |
| WO | WO 2003/104273 A2 | 12/2003 |
| WO | WO 2004/027093 A1 | 4/2004 |
| WO | WO 2007/078868 A1 | 7/2007 |
| WO | WO 2008/097370 A2 | 8/2008 |
| WO | WO 2008/118167 A1 | 10/2008 |
| WO | WO 2008/151146 A2 | 12/2008 |
| WO | WO 2009/132321 A1 | 10/2009 |
| WO | WO 2010/060155 A1 | 6/2010 |
| WO | WO 2010/085763 A1 | 7/2010 |
| WO | WO 2010/096593 A2 | 8/2010 |
| WO | WO 2011/027048 A1 | 3/2011 |
| WO | WO 2011/034620 A2 | 3/2011 |
| WO | WO 2011/058136 A1 | 5/2011 |
| WO | WO 2012/122929 A1 | 9/2012 |
| WO | WO 2012/122959 A1 | 9/2012 |
| WO | WO 2012/154594 A1 | 11/2012 |
| WO | WO 2012/174479 A1 | 12/2012 |
| WO | WO 2013/119845 A1 | 8/2013 |
| WO | WO 2014/052989 A2 | 4/2014 |

OTHER PUBLICATIONS

Beyer et al. (Dec. 21, 2007) Science vol. 318 p. 1888.
Beyer et al. (Dec. 21, 2007) Science vol. 318 p. 1888 supporting online material.
Meinl et al. (Dec. 1993) The Journal of Clinical Investigation vol. 92 pp. 2633 to 2643.
Lim, J-H. et al., "Direct-Write Dip-Pen Nanolithography of Proteins on Modified Silicon Oxide Surfaces," Angewandte Chemie International Edition, Wiley--VCH Verlag GmbH & Co. KGaA, DE, May 23, 2003, pp. 2309-2312, vol. 42, No. 20.
Lin et al., "Synthesis of Water Soluble Photoinitiators of Thioxanthone Derivatives III" Huadong Ligong Daxue Xuebao, Journal of East China University of Science and Technology, 2000, pp. 212-214, 220, vol. 26, No. 2 (with English abstract).
Merrifield, R.B., "Solid Phase Peptide Synthesis. I. The Synthesis of a Tetrapeptide," J Am. Chem. Soc., Jul. 20, 1963, pp. 2149-2154, vol. 85, No. 14.
PCT International Search Report and Written Opinion, PCT Application No. PCT/US13/25190, dated Jun. 26, 2013, 22 pages.

(56) References Cited

OTHER PUBLICATIONS

PCT International Search Report and Written Opinion, PCT Application No. PCT/US2013/062773, dated May 28, 2014, 20 pages.
Pellois, J.P. et al., "Individually Addressable Parallel Peptide Synthesis on Microchips". Nature Biotechnology, Sep. 2002, pp. 922-926, vol. 20, No. 9.
Shin, et al., "Automated Maskless Photolithography System for Peptide Microarray Synthesis on a Chip," J. Comb Chem., 2010, pp. 463-471, vol. 12, No. 4.
Tapia, et al., "Evaluating the Coupling Efficiency of Phosphorylated Amino Acids for Spot Synthesis," Journal of Peptide Science, 2008, pp. 1309-1314, vol. 14, No. 12.
Wagner, J. "Quality Control for Peptide Chip Array Production," PhD. Thesis, 2011, 141 pages, [Online] [Retrieved on Jun. 14, 2013] Retrieved from the Internet<URL:http://artiv.ub.uni-heidelberg.de/volltextserver- /12602/1/report.pdf>.
Zhao, et al., "A Fluorescent Amino Acid Probe to Monitor Efficiency of Peptide Conjugation to Glass Surfaces for High Density Microarrays," Molecular Biosystems Epub, Jan. 13, 2012, pp. 879-887, vol. 8, No. 3.
Alawode, O. E. et al., "Clean Photodecompositionof 1-Methyl-4-Phenyl-1HTetrazole-5(4H)-Thiones to Carbodiimides Proceeds Via a Biradical," The Journal of Organic Chemistry, Jan. 7, 2011, pp. 216-222, vol. 76, No. 1.
Gundagola, A.S.V., Synthesis, Photochemistry, and DNA Photocleavage of Compounds Containing Tetrazolethione Scaffolds, Kansas State University, 2011, 3 pages, [Online] [Retrieved on May 1, 2015] Retrieved from the Internet<URL:http://krex.kstate.edu/dspace/handle/2097/12022>.
PCT Invitation to Pay Additional Fees, PCT Application No. PCT/US2013/062773, Mar. 7, 2014, 9 pages.
PCT International Preliminary Report on Patentability, PCT Application No. PCT/US2013/062773, dated Dec. 18, 2014, 7 pages.
PCT International Search Report and Written Opinion, PCT Application No. PCT/US15/17173, dated Jun. 3, 2015, 16 pages.
PCT Invitation to Pay Additional Fees, PCT Application No. PCT/US13/25190, May 1, 2013, 4 pages.
PCT International Preliminary Report on Patentability, PCT Application No. PCT/US13/25190, dated Apr. 4, 2014, 19 pages.
Arimitsu, K., "Development of Highly Sensitive Photoreactive Materials Utilitizing Photobase-Generating Reactions and Base Proliferation Reactions," Journal of Organic Chemistry, Jan. 2012, pp. 508-516, vol. 70, No. 5.
European Extended Search Report, European Application No. 13747275.9, dated Sep. 25, 2015, 9 pages.
Han, S-Y. et al., "Recent Development of Peptide Coupling Reagents in Organic Synthesis," Tetrahedron, Report No. 672, Mar. 8, 2004, pp. 2447-2467, vol. 60, No. 11.
"Solid-Phase Peptide Synthesis (SPPS) and Applications of Synthetic Peptides," Proteomics 2010, 63 pages, [Online] [Retrieved on Sep. 16, 2015] Retrieved from the Internet<URL:http://bas.niu.edu.tw/download.php?filename=12155_c-f09f16c.ppt&dir=community_forum/31&title=Topic+10-SPPS>.
Sun, X. et al., "Bicyclic Guanidinium Tetraphenylborate: A Photobase Generator and a Photocatalyst for Living Anionic Ring-Opening Polymerization and Cross-Linking of Polymeric Materials Containing Ester and Hydroxy Groups," Journal of the American Chemical Society, Jul. 2008, pp. 8130-8131, vol. 130, No. 26.
Suyama, K. et al., "Photobase Generators: Recent Progress and Application Trend in Polymer Systems," Progress in Polymer Science, Feb. 2009, pp. 194-209, vol. 34, No. 2.
United States Office Action, U.S. Appl. No. 14/454,554, dated Mar. 16, 2015, 14 pages.
Canadian Office Action, Canadian Application No. 2,864,080, dated Nov. 19, 2015, 6 pages.
PCT International Search Report and Written Opinion, PCT Application No. PCT/US15/49528, dated Feb. 1, 2016, 18 pages.
PCT Invitation to Pay Additional Fees, PCT Application No. PCT/US15/49528, Nov. 20, 2015, 3 pages.

Camarero, J., "Recent Developments in the Site-Specific Immobilization of Proteins Onto Solid Supports," Biopolymers, 2008, pp. 450-458, vol. 90, No. 3.
Compound Summary for: CID 44140583, Tris(2,2'-bipyridine)ruthenium(II) dicholoride, 2009, 2 pages, [Online] [Retrieved on Jun. 29, 2014] Retrieved from the InternetURL:http://pubchem.ncbi.nlm.nih.gov/summary/summary.cgi?cid=44140593&loc=ec_rcs]>.
PCT International Search Report and Written Opinion, PCT Application No. PCT/US2013/070207, dated Jun. 23, 2014, 19 pages.
PCT Invitation to Pay Additional Fees, PCT Application No. PCT/US2013/070207, Mar. 14, 2014, 8 pages.
PCT Written Opinion for PCT International Application No. PCT/US2013/070207, dated Feb. 12, 2015, 13 pages.
PCT International Preliminary Report on Patentability for PCT International Application No. PCT/US2013/070207, dated Mar. 30, 2015, 12 pages.
PCT International Search Report and Written Opinion, PCT Application No. PCT/US14/16737, dated Aug. 11, 2014, 17 pages.
PCT Invitation to Pay Additional Fees, PCT Application No. PCT/US14/16737, May 19, 2014, 2 pages.
PCT International Preliminary Report on Patentability for PCT International Application No. PCT/US14/16737, dated Feb. 24, 2015, 6 pages.
Sardesai, N.P. et al., "A Microfluidic Electrochemiluminescent Device for Detecting Cancer Biomarker Proteins," Anal. Bioanal. Chem. Epub Jan. 11, 2013, pp. 3831-3138, vol. 405, No. 11.
Uddayasankar, U. "Towards a Surface Microarray Based Multiplexed Immunoassay on a Digital Microfluidics Platform," Master of Science Thesis, 2010, 78 pages, [Online] [Retrieved on Jun. 29, 2014] Retrieved from the Internet<URL:https://cipweb.cardinal-lp.com/PCTSRS/PCTSRS_DATA/PCT-US%2014-16737/PRIOR_ART_PCT-US_14-16737_Uddayasankar_Master_Thesis_2010.pdf>.
United States Office Action, U.S. Appl. No. 14/672,123, dated Dec. 21, 2015, 10 pages.
Canadian Office Action, Canadian Application No. 2,891,651, dated Jun. 2, 2016, 5 pages.
European Examination Report, European Application No. 13783134.3, dated Apr. 1, 2016, 4 pages.
European Invitation to Pay Additional Search Fees, European Application No. 13783134.3, May 2, 2016, 4 pages.
Japanese Office Action, Japanese Application No. 2014-556684, dated Apr. 4, 2016, 5 pages.
Meinl, E. et al., "Myelin Basic Protein-Specific T Lymphocyte Repertoire in Multiple Sclerosis, Complexity of the Response and Dominance of Nested Epitopes Due to Recruitment of Multiple T Cell Clones," The Journal of Clinical Investigation, Dec. 1993, pp. 2633-2643, vol. 92, No. 6.
Australian First Examination Report, Australian Application No. 2015314934, dated Feb. 13, 2018, 3 pages.
Ballew, J.T., "Antibody Biomarker Discovery Through in Vitro Directed Evolution of Consensus Recognition Epitopes," Proceedings of the National Academy of Sciences of the United States of America, Nov. 26, 2013, pp. 19330-19335, vol. 110, No. 48.
Beyer, M. et al., "Combinatorial Synthesis of Peptide Arrays Onto a Microchip," Science, Dec. 21, 2007, p. 1888, vol. 318, No. 5858.
Buus, S. et al., "High-Resolution Mapping of Linear Antibody Epitopes Using Ultrahigh-Density Peptide Microarrays," Molecular & Cellular Proteomics, Dec. 2012, pp. 1790-1800, vol. 11, No. 12.
Canadian Office Action, Canadian Application No. 2,901,029, dated Sep. 8, 2015, 4 pages.
Canadian Office Action, Canadian Application No. 2,901,029, dated May 5, 2016, 7 pages.
Canadian Office Action, Canadian Application No. 2,885,839, dated Jul. 22, 2016, 4 pages.
Canadian Office Action, Canadian Application No. 2,901,029, dated Dec. 2, 2016, 7 pages.
Canadian Second Office Action, Canadian Application No. 2,885,839, dated Apr. 20, 2017, 4 pages.
Canadian Second Office Action, Canadian Application No. 2,864,080, dated Dec. 1, 2016, 5 pages.
Canadian Second Office Action, Canadian Application No. 2,891,651, dated Feb. 10, 2017, 4 pages.

(56) References Cited

OTHER PUBLICATIONS

Canadian Office Action, Canadian Application No. 2,864,080, dated Jul. 10, 2017, 5 pages.
Canadian Office Action, Canadian Application No. 2,885,839, dated Sep. 15, 2017, 4 pages.
Canadian Office Action, Canadian Application No. 2,891,651, dated Sep. 15, 2017, 4 pages.
Carra, C. et al., "Proton-Coupled Electron Transfer in a Model for Tyrosine Oxidation in Photosystem II," Journal of the American Chemical Society, 2003, pp. 10429-10436, vol. 125.
Choung, R.S. et al., "Determination of B-Cell Epitopes in Patients with Celiac Disease: Peptide Microarrays," PLOS One, e0147777, Jan. 29, 2016, pp. 1-16, vol. 11, No. 1.
"Compound Summary for: CID 44140593, Tris(2,2'-bipyridine)ruthenium(II) dichloride," PubChem Compound, 2009 [Retrieved from the Internet Jun. 29, 2014: <http://pubchem.ncbi.nlm.Qov.summary/summary.cQi?cid=44140593&loc=ec res>.
European Communication Under Rule 164(2)(a) EPC, European Application No. 13798499.3, dated Jun. 29, 2016, 4 pages.
European Examination Report, European Application No. 13798499.3, dated Sep. 23, 2016, 10 pages.
European Second Examination Report, European Application No. 13798499.3, dated May 23, 2017, 6 pages.
European Examination Report, European Application No. 13783134.3, dated Jun. 29, 2016, 12 pages.
European Extended Search Report, European Application No. 14751871.6, dated Aug. 2, 2016, 6 pages.
European Examination Report, European Application No. 14751871.6, dated Jul. 20, 2017, 5 pages.
European Examination Report, European Application No. 13747275.9, dated Sep. 21, 2017, 6 pages.
European Examination Report, European Application No. 13783134.3, dated Dec. 19, 2017, 5 pages.
European Partial Supplementary Search Report, European Application No. 15839169.8, dated Mar. 12, 2018, 20 pages.
Japanese Office Action, Japanese Application No. 2015-558184, dated Jan. 25, 2016, 4 pages.
Japanese Office Action, Japanese Application No. 2016-126181, dated May 22, 2017, 10 pages.
Japanese Office Action, Japanese Application No. 2016-148004, dated Jun. 21, 2017, 7 pages.
Japanese Office Action, Japanese Application No. 2015-534809, dated Aug. 28, 2017, 6 pages.
New Zealand First Examination Report, New Zealand Application No. 730519, dated Oct. 25, 2017, 6 pages.
Resch-Genger et al., "Quantum Dots Versus Organic Dyes as Fluorescent Labels," Nature Methods, Sep. 2008, pp. 763-775, vol. 5, No. 9.
United States Office Action, U.S. Appl. No. 14/432,200, dated Jul. 19, 2017, 17 pages.
United States Office Action, U.S. Appl. No. 14/768,196, dated Sep. 22, 2017, 18 pages.
Wang et al, Microfluidic DNA microarray analysis: A review, 2011, Analytica Chimica Acta, 687, 12-27.
Wei, H. et al., "Electrochemiluminescence oftris(2,2'-bipyridyl)ruthenium and Its Applications in Bioanalysis: A Review," Luminescence, Mar.-Apr. 2011, pp. 77-85.
Young, et al., Peptide Research, Jul. 1990, pp. 194-200, vol. 3, No. 4.
Yuan, L., et al., "Integrated Tyramide and Polymerization-Assisted Signal Amplification for a Highly-Sensitive Immunoassay," Anal. Chem., 2012, pp. 10737-10744, vol. 84, No. 24.

* cited by examiner

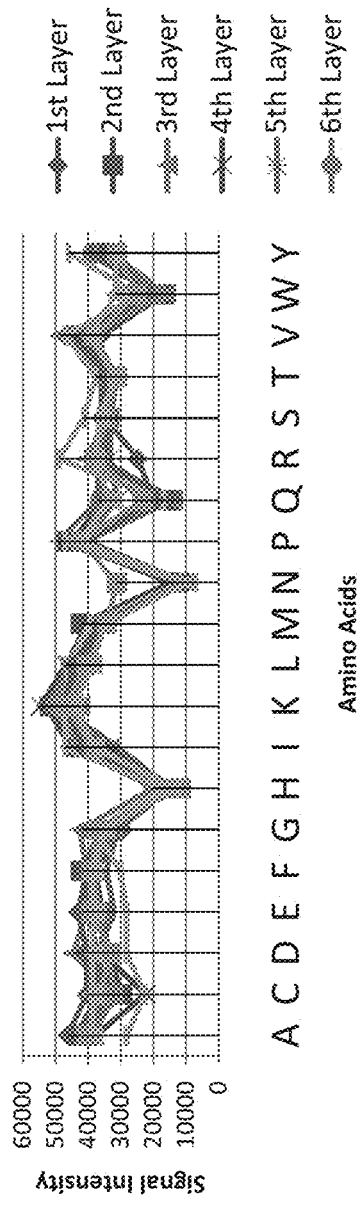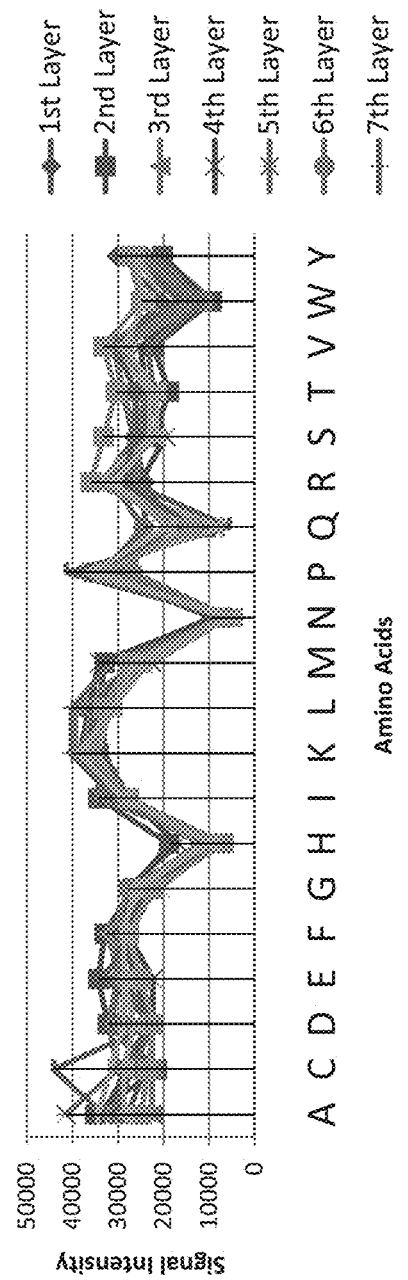
Figure 10

DEAMIDATION OF ALPHA GLIADIN
- ONE Q AT A TIME
PEPTIDE 9 –
PEPTIDE 10 –
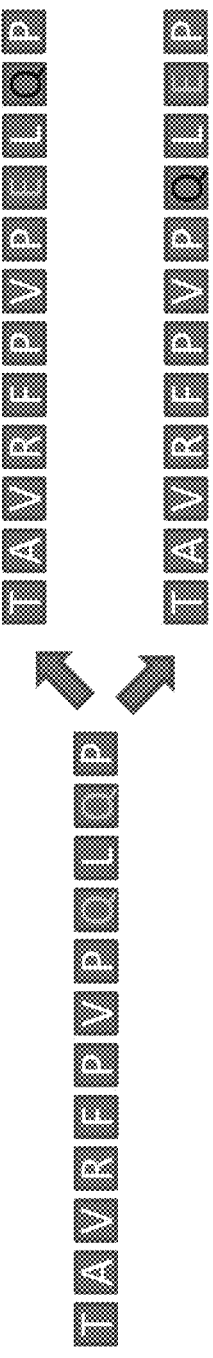
- TWO Q AT A TIME
PEPTIDE 10 –
Figure 16

Matrix combination of Celiac Sequences

IgA

| | QPE | EQP | QPF | FPE | PEQ | PFP | FPQ | PQP | PQQ |
|---|---|---|---|---|---|---|---|---|---|
| %QPE | 10.96% | 21.92% | 91.78% | 21.92% | 26.03% | 83.56% | 36.99% | 9.59% | 2.74% |
| %EQP | 15.07% | 47.95% | 30.14% | 24.66% | 30.14% | 24.66% | 42.47% | 9.59% | 4.11% |
| %QPF | 26.03% | 36.99% | 19.18% | 0.00% | 39.73% | 13.70% | 4.11% | 16.44% | 4.11% |
| %FPE | 12.33% | 8.22% | 6.85% | 1.37% | 8.22% | 4.11% | 2.74% | 1.37% | 0.00% |
| %PEQ | 12.33% | 38.36% | 19.18% | 23.29% | 42.47% | 90.41% | 42.47% | 9.59% | 4.11% |
| %PFP | 27.40% | 36.99% | 19.18% | 1.37% | 24.66% | 13.70% | 6.85% | 2.74% | 1.37% |
| %FPQ | 2.74% | 16.44% | 15.07% | 0.00% | 17.81% | 12.33% | 6.85% | 2.74% | 1.37% |
| %PQP | 5.48% | 23.29% | 21.92% | 0.00% | 5.48% | 19.18% | 9.59% | 1.37% | 0.00% |
| %PQQ | 0.00% | 6.85% | 6.85% | 0.00% | 6.85% | 6.85% | 4.11% | 0.00% | 0.00% |

Figure 18

Matrix combination of Celiac Sequences

IgG

| | QPE | EQP | QPF | FPE | PEQ | PFP | FPQ | PQP | PQQ |
|---|---|---|---|---|---|---|---|---|---|
| %QPE | 7.58% | 12.88% | 67.42% | 14.39% | 16.67% | 63.64% | 25.00% | 7.58% | 1.52% |
| %EQP | 9.09% | 25.76% | 18.94% | 15.91% | 18.94% | 15.91% | 29.55% | 8.33% | 2.27% |
| %QPF | 16.67% | 21.21% | 11.36% | 0.00% | 25.76% | 9.85% | 3.03% | 12.88% | 2.27% |
| %FPE | 6.82% | 3.79% | 3.79% | 0.76% | 3.79% | 3.03% | 1.52% | 0.76% | 0.00% |
| %PEQ | 7.58% | 19.70% | 10.61% | 15.91% | 24.24% | 68.94% | 28.79% | 7.58% | 2.27% |
| %PFP | 22.73% | 28.03% | 18.18% | 0.76% | 20.45% | 14.39% | 6.82% | 3.03% | 0.76% |
| %FPQ | 3.03% | 16.67% | 15.91% | 0.00% | 17.42% | 13.64% | 6.06% | 1.52% | 0.76% |
| %PQP | 3.03% | 19.70% | 18.94% | 0.00% | 3.03% | 16.67% | 6.06% | 0.76% | 0.00% |
| %PQQ | 0.76% | 5.30% | 4.55% | 2.27% | 6.82% | 6.06% | 2.27% | 0.00% | 0.00% |

Figure 19

Process Flow

There are two cells – coater/developer and litho cell which are connected inline. The wafers which are placed on the foup can be passed between two machines without requiring any manual intervention Process Flow
Step 4 - The wafers are cooled at 21C for 60 seconds

Process Flow

Step 5 - The wafers are transferred from the coater/developer machine to the scanner through the inline connection and exposed in the scanner with the use of a particular reticle

Process Flow

Step 9 (a) - The wafers were coated with Amino Acid Solution. The amino acid solution was prepared using the corresponding amino acid. Reagent R1 was added to it in the corresponding reservoir, heated at 60C for 15 minutes and then Reagent R2 was added. Then, the solution was transferred from a particular reservoir to the corresponding nozzle. The same process occurred for AA1 – AA10 or AA11 - AA20

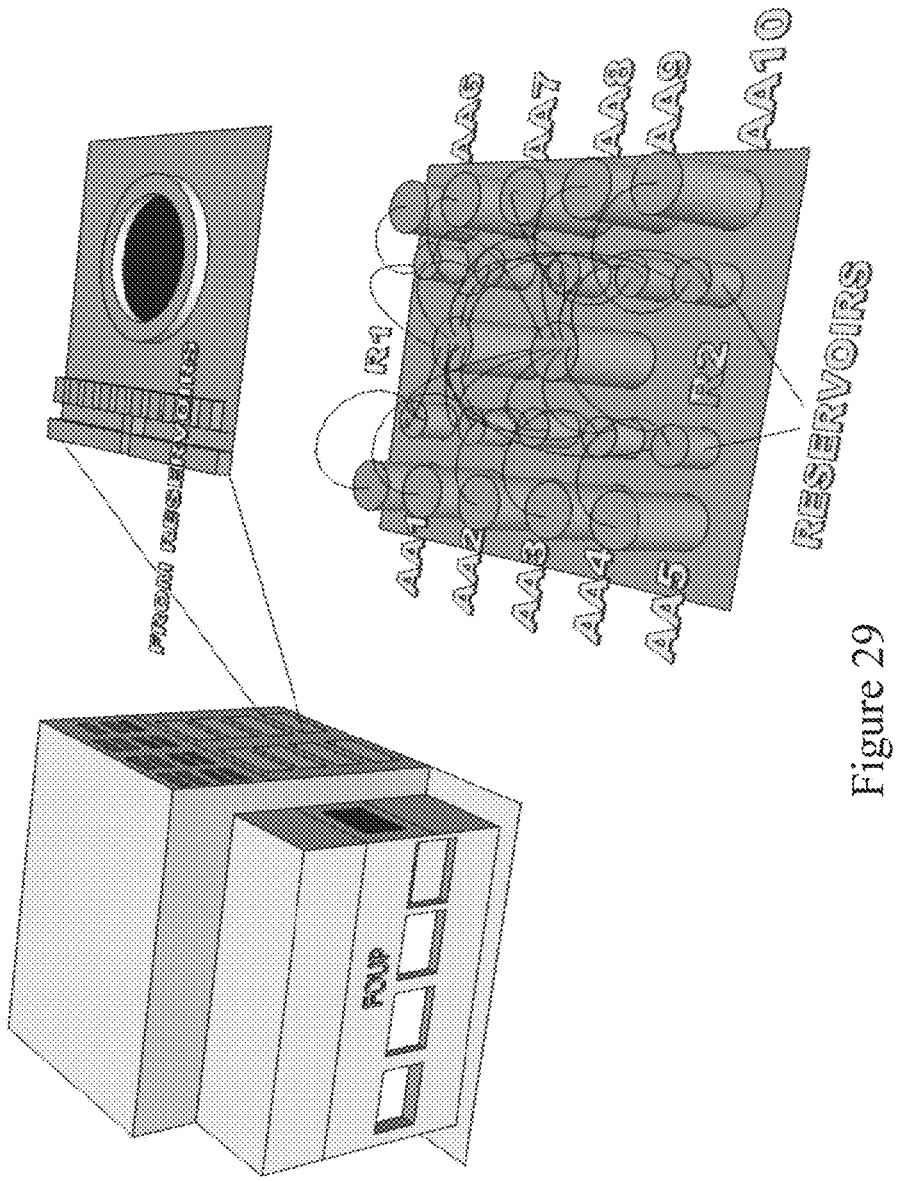

Figure 29

Process Flow

Step 9 (b) - The wafers were coated with Amino Acid Solution. The amino acid solution was prepared using the corresponding amino acid. Reagent R1 was added to it in the corresponding reservoir, heated at 60C for 15 minutes and then Reagent R2 was added. Then, the solution was transferred from a particular reservoir to the corresponding nozzle. The same process occurred for AA1 – AA10 or AA11- AA20

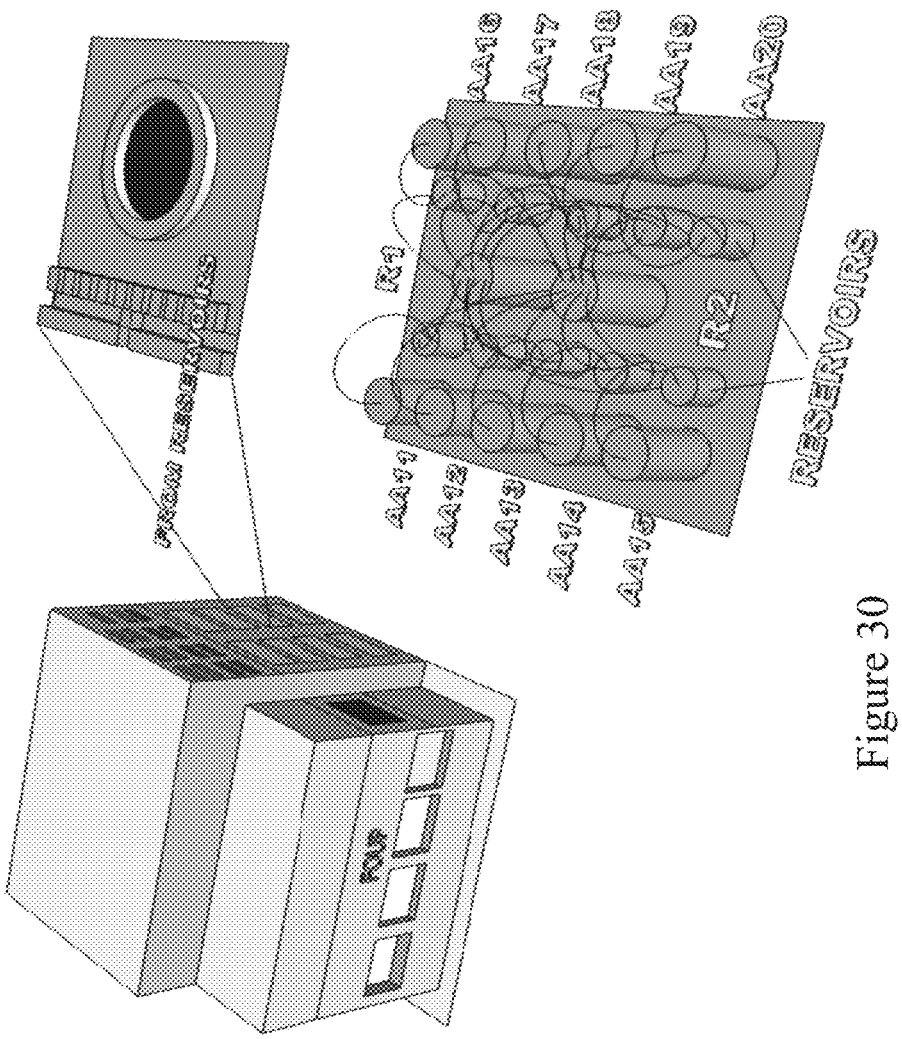

Figure 30

Process Flow
Step 10 - The wafers are baked at 60C for 60 seconds

```
                        SEQUENCE LISTING

<160> NUMBER OF SEQ ID NOS: 60

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Pro Glu Gln Pro Phe
1               5

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Ala Ala Ala Ala Ala Ala Ala Ala Ala Ala Ala Ala Ala Ala
1               5                   10                  15

Ala Ala Ala Ala
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Asp Asp Asp Asp Asp Asp Asp Asp Asp Asp Asp Asp Asp Asp Asp
1               5                   10                  15

Asp Asp Asp Asp
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His His His His His His His His His His His His His His His His
1               5                   10                  15

His His His His
            20
```

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Leu Glu Arg Ser Thr Val Met Ile Lys Gly Asp
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Leu Glu Arg
1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Leu Glu Arg Ser
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Leu Glu Arg Ser Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Leu Glu Arg Ser Thr Val
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 10

Lys Leu Glu Arg Ser Thr Val Met
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Leu Glu Arg Ser Thr Val Met Ile
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Leu Glu Arg Ser Thr Val Met Ile Lys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Leu Glu Arg Ser Thr Val Met Ile Lys Gly
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ala Ala Ala Ala Ala Ala Ala Ala Ala Ala
1               5                   10

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ala Ala
1

<210> SEQ ID NO 16
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 16

Ala Ala Ala Ala Ala
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Ala Ala Ala Ala
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Ala Ala Ala Ala Ala
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Ala Ala Ala Ala Ala Ala
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Ala Ala Ala Ala Ala Ala Ala
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ala Ala Ala Ala Ala Ala Ala Ala Ala
1               5                   10
```

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Ala Ala Ala Ala Ala Ala Ala Ala Ala
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Gln Gln Pro Glu Gln Ile Ile
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ala Ile Gln Thr Phe Gln Asn Thr Tyr Gln Val
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Ile Glu Thr Phe Gln Asn Thr Tyr Gln Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Ala Ile Gln Thr Phe Glu Asn Thr Tyr Gln Val
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ala Ile Gln Thr Phe Gln Asn Thr Tyr Glu Val
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ala Ile Glu Thr Phe Glu Asn Thr Tyr Gln Val
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Ile Gln Thr Phe Glu Asn Thr Tyr Glu Val
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Ala Ile Glu Thr Phe Gln Asn Thr Tyr Glu Val
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ala Ile Glu Thr Phe Glu Asn Thr Tyr Glu Val
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Ala Leu Glu Lys Asp
1               5

<210> SEQ ID NO 33
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Pro Leu Glu Glu Val Glu Asn Leu
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Pro Tyr Asp Val Glu Pro Asp Tyr Ala
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg His Ser Val Val
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Pro Asp Asp Ile Glu Gln Trp Phe Thr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Lys Trp Leu Asp Ser Phe Thr Glu Gln
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Lys Thr Phe Leu Ile Leu Val Leu Leu Ala Thr
```

```
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Phe Leu Ile Leu Val Leu Leu Ala Thr Ile Val
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Ile Leu Val Leu Leu Ala Thr Ile Val Ala Thr
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Val Leu Leu Ala Thr Ile Val Ala Thr Ala Thr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Leu Ala Thr Ile Val Ala Thr Ala Thr Thr Ala
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Thr Ile Val Ala Thr Ala Thr Thr Ala Val Arg
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 44

Ile Val Ala Thr Ala Thr Thr Ala Val Arg Phe Pro
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Thr Ala Thr Thr Ala Val Arg Phe Pro Val Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Thr Thr Ala Val Arg Phe Pro Val Pro Gln Leu
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Ala Val Arg Phe Pro Val Pro Gln Leu Gln Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Arg Phe Pro Val Pro Gln Leu Gln Pro Gln Asn
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Thr Ile Ala Pro Phe Gly Ile Phe Gly Thr Asn
1               5                   10

<210> SEQ ID NO 50

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Thr Thr Ala Val Arg Phe Pro Val Pro Glu Leu
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ala Val Arg Phe Pro Val Pro Glu Leu Gln Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ala Val Arg Phe Pro Val Pro Gln Leu Glu Pro
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ala Val Arg Phe Pro Val Pro Glu Leu Glu Pro
1               5                   10

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Pro Gln Gln Pro Phe Pro Gln Gln Pro Glu Gln Ile Ile Pro Gln
1               5                   10                  15

Gln Pro Gln Gln
            20

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 55

Gln Pro Gln Gln Pro Phe Pro Gln Gln Pro Glu Gln
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Pro Phe Pro Gln Gln Pro Glu Gln Ile Ile
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Phe Pro Gln Gln Pro Glu Gln Ile Ile Pro Gln
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Pro Gln Gln Pro Glu Gln Ile Ile Pro Gln Gln Pro
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Pro Glu Gln Ile Ile Pro Gln Gln Pro Gln Gln
1               5                   10

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Cys Asp Glu Phe Gly His Ile Lys Leu Met Asn Pro Gln Arg Ser
1               5                   10                  15

Thr Val Trp Tyr
            20
```

SUBSTRATES, PEPTIDE ARRAYS, AND METHODS

CROSS-REFERENCE TO RELATED APPLICATIONS

This application is a divisional application of U.S. application Ser. No. 14/454,554, filed Aug. 7, 2014, which claims the benefit of International Application No. PCT/US2013/025190, filed Feb. 7, 2013, which claims the benefit of the following U.S. Provisional Applications: U.S. Provisional Application No. 61/595,908, filed Feb. 7, 2012, U.S. Provisional Application No. 61/595,988, filed Feb. 7, 2012, U.S. Provisional Application No. 61/608,554, filed Mar. 8, 2012, U.S. Provisional Application No. 61/609,003, filed Mar. 9, 2012, U.S. Provisional Application No. 61/665,489, filed Jun. 28, 2012, U.S. Provisional Application No. 61/726,515, filed Nov. 14, 2012, and U.S. Provisional Application No. 61/761,347, filed Feb. 6, 2013. The disclosures of the International Application No. PCT/US2013/02590 and the above cited U.S. Provisional Applications are incorporated by reference in their entirety for all purposes.

SEQUENCE LISTING

The instant application contains a Sequence Listing which has been submitted via EFS-Web and is hereby incorporated by reference in its entirety. Said ASCII copy, created on Nov. 13, 2015, is named 32561_US_CRF_Sequence_Listing.txt, and is 15,130 bytes in size.

BACKGROUND

A typical microarray system generally comprises biomolecular probes, such as DNA, proteins, or peptides, formatted on a solid planar surface like glass, plastic, or silicon chip, plus the instruments needed to handle samples (automated robotics), to read the reporter molecules (scanners) and analyze the data (bioinformatic tools). Microarray technology can facilitate monitoring of many probes per square centimeter. Advantages of using multiple probes include, but are not limited to, speed, adaptability, comprehensiveness and the relatively cheaper cost of high volume manufacturing. The uses of such an array include, but are not limited to, diagnostic microbiology, including the detection and identification of pathogens, investigation of anti-microbial resistance, epidemiological strain typing, investigation of oncogenes, analysis of microbial infections using host genomic expression, and polymorphism profiles.

Recent advances in genomics have culminated in sequencing of entire genomes of several organisms, including humans. Genomics alone, however, cannot provide a complete understanding of cellular processes that are involved in disease, development, and other biological phenomena; because such processes are often directly mediated by polypeptides. Given that huge numbers of polypeptides are encoded by an organism's genome, the development of high throughput technologies for analyzing polypeptides is of paramount importance.

Peptide arrays with distinct analyte-detecting regions or probes can be assembled on a single substrate by techniques well known to one skilled in the art. A variety of methods are available for creating a peptide microarray. These methods include: (a) chemo selective immobilization methods; and (b) in situ parallel synthesis methods which can be further divided into (1) SPOT synthesis and (2) photolithographic synthesis. However, the prior art methods suffer from several deficiencies, including limitations on feature density, consistent feature quality (e.g., for step-wise synthesis, coupling efficiencies consistently approaching 98% or higher), and in some aspects, the use of toxic chemicals. The present invention addresses these and other shortcomings of the prior art, as described below.

SUMMARY

The invention encompasses, in several aspects formulations, substrates, and arrays. The invention also includes methods for manufacturing and using the formulations, substrates, and arrays.

In one embodiment, the invention includes an array of features attached to a porous surface layer at positionally-defined locations, the features each comprising: a collection of peptide chains of determinable sequence and intended length, wherein within an individual feature, the fraction of peptide chains within the collection having the intended length is characterized by an average coupling efficiency for each coupling step of at least 98%.

In certain embodiments, the porous layer comprises a plurality of free carboxylic acid groups. In one embodiment, the carboxylic acid groups are oriented in multiple directions. In some embodiments, the porous layer comprises a plurality of coupling molecules each attached to the array via a carboxylic acid group. In other embodiments, the porous layer comprises a plurality of peptide chains each attached to the array via a carboxylic acid group.

In one embodiment, the average coupling efficiency of each coupling step is at least 98.5%. In some embodiments, the average coupling efficiency of each coupling step is at least 92%, 93%, 94%, 95%, 96%, 97%, 98%, or 99%. In certain embodiments, each intended length is from 4 to 60 amino acids in length. In some embodiments, each intended length is at least 5 amino acids in length. In one embodiment, each intended length is at least 6, 10, 15, 20, 25, 30, 35, 40, 45, 50, 55, or 60 amino acids in length.

In certain embodiments, each peptide chain comprises one or more L amino acids. In one embodiment, each peptide chain comprises one or more D amino acids. In certain embodiments, each peptide chain comprises one or more naturally occurring amino acids. In some embodiments, each peptide chain comprises one or more synthetic amino acids. In some embodiments, the array comprises at least 1,000 different features. In some embodiments, the array comprises at least 10,000 different features.

In certain embodiments, each of the positionally-defined locations is at a different, known location that is physically separated from each of the other positionally-defined locations. In some embodiments, each of the positionally-defined locations comprises a plurality of identical sequences. In some embodiments, each positionally-defined location comprises a plurality of identical sequences unique from the other positionally-defined locations. In some embodiments, each of the positionally-defined locations is a positionally-distinguishable location. In some embodiments, each determinable sequence is a known sequence. In some embodiments, each determinable sequence is a distinct sequence.

In one embodiment, the features are covalently attached to the surface. In one embodiment, the peptide chains are attached to the porous surface layer through a linker molecule or a coupling molecule. In one embodiment, the features comprise a plurality of distinct, nested, overlapping peptide chains comprising subsequences derived from a source protein having a known sequence. In one embodiment, each peptide chain in the plurality is at least 5 amino acids in length. In some embodiments, each peptide chain in the plurality is at least 5, 10, 15, 20, 25, 30, 35, 40, 45, 50, 55, or 60 amino acids in length.

In some embodiments, the features comprise a plurality of peptide chains each having a random, determinable sequence of amino acids. In some embodiments, the surface comprises any of the substrates described above.

In one embodiment, the invention comprises an array of features attached to a surface at positionally-defined locations, the features each comprising: a collection of peptide chains of determinable sequence and intended length, wherein within an individual feature, the fraction of peptide chains within the collection having the intended length is characterized by an average coupling efficiency for each coupling step of at least 98%.

In one embodiment, the average coupling efficiency for each coupling step is at least 98.5%. In one embodiment, the average coupling efficiency for each coupling step is at least 99%. In one embodiment, each intended length is from 4 to 60 amino acids in length. In some embodiments, each intended length is at least 3 amino acids in length. In certain embodiments, each intended length is at least 5 amino acids in length.

In some embodiments, each intended length is at least 5, 10, 15, 20, 25, 30, 35, 40, 45, 50, 55, or 60 amino acids in length. In certain embodiments, each peptide chain comprises one or more L amino acids. In certain embodiments, each peptide chain comprises one or more D amino acids. In some embodiments, each peptide chain comprises one or more naturally occurring amino acids. In one embodiment, each peptide chain comprises one or more synthetic amino acids.

In one embodiment, the array comprises at least 1,000 different features. In some embodiments, the array comprises at least 10,000 different features.

In certain embodiments, each of the positionally-defined locations is at a different, known location that is physically separated from each of the other positionally-defined locations. In some embodiments, each of the positionally-defined locations is a positionally-distinguishable location. In one embodiment, each determinable sequence is a known sequence. In one embodiment, each determinable sequence is a distinct sequence. In some embodiments, the features are covalently attached to the surface. In some embodiments, the peptide chains are attached to the surface through a linker molecule or a coupling molecule.

In one embodiment, the features comprise a plurality of distinct, nested, overlapping peptide chains comprising subsequences derived from a source protein having a known sequence. In certain embodiments, each peptide chain in the plurality is at least 5 amino acids in length.

In one embodiment, each peptide chain in the plurality is at least 5, 10, 15, 20, 25, 30, 35, 40, 45, 50, 55, or 60 amino acids in length. In some embodiments, the features comprise a plurality of peptide chains each having a random, determinable sequence of amino acids. In some embodiments, the surface comprises the substrate disclosed herein.

In one embodiment, the invention includes a method of producing an array of features, comprising: obtaining a surface; and attaching the features to the surface, the features each comprising a collection of peptide chains of determinable sequence and intended length, wherein within an individual feature, the fraction of peptide chains within the collection having the intended length is characterized by an average coupling efficiency for each coupling step of at least 98%.

In one embodiment, the features are attached to the surface using a coupling formulation, comprising a solvent, a water soluble polymer, a water soluble coupling molecule, a water soluble neutralization reagent, and a water soluble coupling reagent.

In one embodiment, the invention includes a method of producing an array of features, comprising: obtaining a substrate comprising a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein the surface of each pillar is parallel to the upper surface of the layer, and wherein the plurality of pillars are present at a density of greater than $10,000/cm^2$; and coupling through a series of coupling reactions the features to the plurality of pillars, the features each comprising a collection of peptide chains of determinable sequence and intended length, wherein within an individual feature, the fraction of peptide chains within the collection having the intended length is characterized by an average coupling efficiency for each coupling step of at least 98%.

In one embodiment, the features are coupled to the pillars using a coupling formulation, comprising a solvent, a water soluble polymer, a water soluble coupling molecule, a water soluble neutralization reagent, and a water soluble coupling reagent.

In one embodiment, the invention includes a photoactive formulation, comprising: a water soluble photosensitizer, a water soluble photo active compound, a water soluble polymer, and a solvent.

In certain embodiments, the formulation is selected from the photoactive formulations shown in Table 1

In some embodiments, the water soluble photosensitizer is a thioxanthenone. In some embodiments the water soluble photosensitizer is about 0.5-5% by weight of the total formulation concentration. In some embodiments, the water soluble photoactive compound comprises a photoacid generator (PAG) or a photobase generator (PBG). In some embodiments, the photoacid generator is a water soluble iodonium salt, a water soluble polonium salt, or a water soluble sulfonium salt. In some embodiments, the photoacid generator is (4-Methoxyphenyl)phenyliodoniumtrifluoromethanesulfonate. In some embodiments, the photoacid generator is (2,4-dihydroxyphenyl)dimethylsulfonium triflate or (4 methoxyphenyl)dimethylsulfonium triflate. In some embodiments, the photoacid generator is iodonium and sulfonium salts of triflates, phosphates and/or antimonates. In some embodiments, the photoacid generator is about 0.5-5% by weight of the total formulation concentration. In some embodiments, the water soluble polymer is a water soluble non-crosslinking inert polymer. In some embodiments, the water soluble polymer is a vinyl pyrrolidone. In some embodiments, the water soluble polymer is polyvinyl pyrrolidone. In some embodiments, the water soluble polymer is about 0.5-5% by weight of the total formulation concentration. In some embodiments, the solvent is water, ethyl lactate, or a combination thereof. In some embodiments, the solvent is about 80-90% by weight of the total formulation concentration.

In other embodiments, the invention includes a linker formulation, comprising: a solvent, a water soluble polymer, a water soluble linker molecule, and a water soluble coupling reagent. In some embodiments, the polymer is 1% by weight polyvinyl alcohol and 2.5% by weight poly vinyl pyrrollidone, the linker molecule is 1.25% by weight polyethylene oxide, the coupling reagent is 1% by weight 1-ethyl-3-(3-dimethylaminopropyl) carbodiimide, and the solvent is water.

In some embodiments, the solvent is water, an organic solvent, or a combination thereof. In some aspects, the organic solvent is N Methyl pyrrolidone, Di methyl formamide, Di chloromethane, Di methyl sulfoxide, or a combination thereof. In some embodiments, the water soluble polymer is a polyvinyl pyrrolidone or a polyvinyl alcohol. In some embodiments, the coupling reagent is a water soluble carbodimide or a water soluble triazole. In some embodiments, the coupling reagent is 1-ethyl-3-(3-dimethylaminopropyl) carbodiimide. In some embodiments, the linker molecule comprises a carboxylic group at a first end of the molecule and a protecting group at a second end of the molecule. In some embodiments, the protecting group is a t-Boc protecting group or an F-Moc protecting group. In some embodiments, the linker molecule is an aryl acetylene, a polyethyleneglycol, a nascent polypeptide, a diamine, a diacid, a peptide, or combinations thereof.

Also encompassed is a coupling formulation, comprising: a solvent, a water soluble polymer, a water soluble coupling molecule, a water soluble neutralization reagent, and a water soluble coupling reagent.

In some embodiments, the formulation is selected from the coupling film contacting formulations shown in Table 2.

In some aspects, the solvent is water, an organic solvent, or combination thereof. In some embodiments, the organic solvent is N Methyl pyrrolidone, di methyl formamide or combinations thereof. In some embodiments, the polymer is a water soluble vinyl pyrrolidone or a water soluble vinyl alcohol. In some embodiments, the polymer is 2.5-5% by weight of the total formulation concentration. In some embodiments, the neutralization reagent comprises Hunig's base. In some embodiments, the neutralization reagent is 1-2% by weight of the total formulation concentration. In some embodiments, the coupling molecule comprises a naturally occurring or artificial amino acid or polypeptide. In some embodiments, the artificial amino acid is a D-amino acid. In some embodiments, the coupling molecule is 1-2% by weight of the total formulation concentration. In some embodiments, the coupling molecule comprises a protected side group. In some embodiments, the coupling reagent is water soluble carbodimide or water soluble triazole. In some embodiments, the coupling reagent is 2-4% by weight of the total formulation concentration.

In some embodiments, the invention includes a substrate, comprising: a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein the surface of each pillar is parallel to the upper surface of the layer, and wherein the plurality of pillars are present at a density of greater than 10,000/cm$^2$.

In some embodiments, the surface area of each pillar surface is at least 1 µm$^2$. In some embodiments, the surface area of each pillar surface has a total area of less than 10,000 µm$^2$. In some embodiments, the distance between the surface of each pillar and the lower surface of the layer is 2,000-7,000 angstroms. In some embodiments, the layer is 1,000-2,000 angstroms thick. In some embodiments, the center of each pillar is at least 2,000 angstroms from the center of any other pillar. In some embodiments, the metal is chromium. In some embodiments, the metal is chromium, titanium, aluminum, tungsten, gold, silver, tin, lead, thallium, or indium. In some embodiments, the layer is at least 98.5-99% metal. In some embodiments, the layer is a homogenous layer of metal. In some embodiments, each pillar comprises silicon dioxide or silicon nitride. In some embodiments, each pillar is at least 98-99% silicon dioxide.

In some embodiments, the substrate further includes a linker molecule having a free amino terminus attached to the surface of each pillar. In some embodiments, the substrate further includes a linker molecule having a free amino terminus attached to the surface of at least one pillar. In some embodiments, the substrate further includes a linker molecule having a protecting group attached to the surface of each pillar. In some embodiments, the substrate further includes a linker molecule having a protecting group attached to the surface of at least one pillar. In some embodiments, the substrate further includes a coupling molecule attached to the surface of at least one pillar. In some embodiments, the substrate further includes a coupling molecule attached to the surface of each pillar. In some embodiments, the substrate further includes a water soluble polymer in contact with the surface of at least one of the pillars. In some embodiments, the substrate further includes a water soluble polymer in contact with the surface of each pillar. In some embodiments, the substrate further includes a gelatinous form of a water soluble polymer in contact with the surface of at least one of the pillars. In some embodiments, the substrate further includes a solid form of a water soluble polymer in contact with the surface of at least one of the pillars.

In some embodiments, the surface of at least one of the pillars is derivatized. In some embodiments, the substrate further includes a polymer chain attached to the surface of at least one of the pillars. In some embodiments, said polymer chain comprises a peptide chain. In some embodiments, said attachment to the surface of said at least one pillar is via a covalent bond. In some embodiments, the surface of each pillar is square or rectangular in shape. In some embodiments, the substrate is coupled to a silicon wafer.

In still other embodiments, the invention includes a method of preparing a substrate for attachment of features, comprising: obtaining a substrate comprising a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein the surface of each pillar is parallel to the upper surface of the layer, and wherein the plurality of pillars are present at a density of greater than 10,000/cm$^2$; and attaching one or more linker molecules to the plurality of pillars. In some embodiments, the linker molecule is attached using a linker formulation, comprising a solvent, a water soluble polymer, a water soluble linker molecule, and a water soluble coupling reagent. In some embodiments, the linker molecule comprises a protecting group.

In some embodiments, the surface of each pillar is parallel to the upper surface of the layer. In other embodiments, the surface of each pillar is substantially parallel to the upper surface of the layer.

The invention also encompasses a method of preparing a surface for attachment of features, comprising: obtaining a surface and attaching a linker molecule to the surface using a linker formulation, comprising a solvent, a water soluble polymer, a water soluble linker molecule, and a water soluble coupling reagent. In some embodiments, the linker molecule comprises a protecting group.

In yet other embodiments the invention includes a method of attaching a coupling reagent to a substrate, comprising: obtaining a substrate comprising a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein a linker molecule is attached to the surface of each pillar, and wherein the plurality of pillars are present at a density of greater than $10,000/cm^2$; and attaching the coupling reagent to one or more linker molecules. In some embodiments, the coupling reagent is attached to the one or more linker molecules using a coupling formulation, comprising: a solvent, a water soluble polymer, a water soluble coupling molecule, a water soluble neutralization reagent, and a water soluble coupling reagent. In some embodiments, at least one the linker molecule is a deprotected linker molecule. In some embodiments, the coupling reagent is an amino acid. In some embodiments, the coupling reagent comprises a protecting molecule.

In some embodiments, the surface of each pillar is parallel to the upper surface of the layer. In other embodiments, the surface of each pillar is substantially parallel to the upper surface of the layer.

In still other embodiments the invention includes a method of attaching a coupling reagent to a surface, comprising: obtaining a surface having a linker molecule attached to the surface and attaching the coupling reagent to the linker molecule using a coupling formulation, comprising a solvent, a water soluble polymer, a water soluble coupling molecule, a water soluble neutralization reagent, and a water soluble coupling reagent. In some aspects, the linker molecule is a deprotected linker molecule. In some embodiments, the coupling reagent is an amino acid. In some embodiments, the coupling reagent comprises a protecting molecule.

The invention further includes a method of preparing a substrate for attachment of a coupling reagent, comprising: obtaining a substrate comprising a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein a linker molecule is attached to the surface of each pillar, wherein the substrate is contacted with a photoactive formulation, and wherein the plurality of pillars are present at a density of greater than $10,000/cm^2$; and applying ultraviolet light to the substrate. In some embodiments, the photoactive formulation comprises a water soluble photosensitizer, a water soluble photo active compound, a water soluble polymer, and a solvent. In some embodiments, the linker molecule comprises a protecting group. In some embodiments, application of the light to the substrate results in removal of the protecting group from the linker molecule. In some embodiments, the light is 248 nm light.

In some embodiments, the surface of each pillar is parallel to the upper surface of the layer. In other embodiments, the surface of each pillar is substantially parallel to the upper surface of the layer.

The invention further includes a method of preparing a surface for attachment of a coupling reagent, comprising: obtaining a surface having a linker molecule attached to the surface and contacted with a photoactive formulation comprising a water soluble photosensitizer, a water soluble photo active compound, a water soluble polymer, and a solvent; and applying ultraviolet light to the surface. In some embodiments, the linker molecule comprises a protecting group. In some embodiments, application of the light to the substrate results in removal of the protecting group from the linker molecule. In some embodiments, the light is 248 nm light.

In still other embodiments the invention includes a method of producing a substrate comprising coupling a planar layer to a plurality of pillars, wherein the planar layer comprises a metal and has an upper surface and a lower surface, wherein the plurality of pillars are coupled to the layer in positionally-defined locations, wherein each pillar has a planar surface extended from the layer, wherein the distance between the surface of each pillar and the upper surface of the layer is between 1,000-5,000 angstroms, and wherein the plurality of pillars are present at a density of greater than $10,000/cm^2$.

In some embodiments, the surface of each pillar is parallel to the upper surface of the layer. In other embodiments, the surface of each pillar is substantially parallel to the upper surface of the layer.

In yet other embodiments the invention includes a method of preparing a surface comprising: obtaining a surface comprising silicon dioxide and contacted with a photoactive formulation comprising a water soluble photosensitizer, a water soluble photo active compound, a water soluble polymer, and a solvent; and applying ultraviolet light to positionally-defined locations located on the top of the surface and in contact with the photoactive formulation, wherein the surface area of each positionally-defined location on the surface has a total area of less than $10,000/\mu m^2$. In some embodiments, the method further includes removing the photoactive formulation located external to the positionally-defined locations. In some embodiments, the method further includes reducing the thickness of the top of the surface located external to the positionally-defined locations. In some embodiments, the method further includes depositing a metal layer on the top of the surface with reduced thickness. In some embodiments, the method further includes removing the photoactive formulation in contact with the positionally-defined locations located on the top of the surface.

The invention also includes a method of detecting the presence or absence of a protein of interest in a sample, comprising: obtaining an array disclosed herein contacted with a sample suspected of comprising the protein of interest; and determining whether the protein of interest is present in the sample by detecting the presence or absence of binding to one or more features of the array.

In still other embodiments the invention includes a method of identifying a vaccine candidate, comprising: obtaining an array disclosed herein contacted with a sample derived from a subject previously administered the vaccine candidate, wherein the sample comprises a plurality of antibodies; and determining the binding specificity of the plurality of antibodies to one or more features of the array. In some embodiments, the features comprise a plurality of distinct, nested, overlapping peptide chains comprising subsequences derived from a source protein having a known sequence.

In some embodiments, the invention comprises a peptide array, comprising: a plurality of peptides coupled to a support; wherein the plurality of peptides comprises overlapping subsequences of a source protein of known sequence. In some embodiments, the source protein is selected from the group consisting of: an alpha gliadin protein, a secalin protein, a hordein protein, a savina protein, a prolamin protein, or a transglutaminase protein. In certain embodiments, the source protein is an alpha gliadin protein and wherein the overlapping subsequences further comprise at least one sequence variant comprising a substitution of a glutamine residue with a glutamic acid residue.

In some embodiments, the invention comprises a peptide array, comprising: a plurality of peptides coupled to a support; wherein the plurality of peptides comprises a peptide sequence comprising an epitope recognized by an antibody from a subject diagnosed with celiac disease.

In one embodiment, the plurality of peptides comprises a peptide further comprising at least two epitope sequences recognized by an antibody from a subject. In some embodiments, the array is prepared at a density of at least 10,000 peptide molecules per square centimeter of the substrate surface. In some embodiments, the support comprises a pillar on the surface of the peptide array. In some embodiments, the peptide array comprises a plurality of peptides with a length of 12 or fewer amino acids.

In some embodiments, the invention comprises a method of diagnosing an disorder in a subject suspected of having the disorder, comprising: obtaining a peptide array, wherein the peptide array comprises a peptide sequence comprising an epitope recognized by an antibody obtained from a subject diagnosed with the disorder; contacting the peptide array with a sample obtained from the subject suspected of having the disorder to generate a signal; and diagnosing the disorder in the subject based on the signal.

In one embodiment, the disorder is an autoimmune disorder, an infectious disease, or a cancer. In some embodiments, the antibody is an autoimmune antibody. In some embodiments, the antibody is selected from the group consisting of: IgG, IgA, IgM, IgD, and IgE.

In certain embodiments, the peptide sequence comprising the epitope is capable of stimulating an immune response in the subject suspected of having the disorder or in a sample comprising lymphocytes obtained from the subject suspected of having the disorder. In some embodiments, the immune response is measured by an increased quantity of interferon in the presence of a peptide comprising the epitope. In some embodiments, the epitope is capable of stimulating a B cell from the subject. In some embodiments, the peptide array has a feature density of at least 10,000 peptides molecules per square centimeter. In some embodiments, the peptide array is the array disclosed herein.

In one embodiment, the peptide array comprises a peptide comprising a plurality of epitopes. In certain embodiments, the epitope comprises the sequence: 'QPEQPF' (SEQ ID NO: 1). In some embodiments, the method of diagnosis has a sensitivity of greater than 99%. In some embodiments, the method of diagnosis has a specificity of greater than 99%. In some embodiments, the method of diagnosis determines subtype of the disorder. In some embodiments, the method of diagnosis determines severity of the disorder. In certain embodiments, the disorder is celiac disease.

In some embodiments, the invention comprises a method of identifying an epitope sequence associated with a disorder, comprising: providing a first peptide array disclosed herein; contacting the first peptide array with a biological fluid obtained from a subject known to have the disorder; analyzing the first peptide array to detect binding of an antibody associated with the disorder to at least one peptide sequence attached to the first peptide array; and identifying an epitope sequence comprising at least 3 contiguous amino acids by comparing the binding pattern of antibody to epitope peptide sequences attached to the surface of the first peptide array.

In one embodiment, the disorder is an autoimmune disorder, an infectious disease, or a cancer. In some embodiments, the biological fluid is selected from the group consisting of: blood, serum, plasma, bile, mucus, pus, or urine. In some embodiments, at least 60% of peptides comprising the epitope are bound by an antibody associated with the disorder. In certain embodiments, at least 70% of peptides comprising the epitope are bound by an antibody associated with the disorder. In certain embodiments, at least 80% of peptides comprising the epitope are bound by an antibody associated with the disorder. In certain embodiments, at least 90% of peptides comprising the epitope are bound by an antibody associated with the disorder. In some embodiments, the percentage of peptides comprising the epitope that are bound to antibody associated with the disorder during the first screen is greater when the sample is positive for the disorder than when the sample is negative for the disorder.

In some embodiments, the invention comprises method of generating a peptide array for diagnosis of an disorder, comprising: providing a first peptide array disclosed herein; contacting the first peptide array with a biological fluid obtained from a subject known to have the disorder; analyzing the first peptide array to detect binding of an antibody associated with the disorder to at least one peptide sequence attached to the first peptide array; analytically determining an epitope sequence comprising at least 3 contiguous amino acids from the binding pattern of antibody to the first peptide array; and generating a peptide array for diagnosis of the disorder, wherein the peptide array comprises a peptide comprising the epitope sequence.

In some embodiments, the disorder is an autoimmune disorder, an infectious disease, or cancer. In certain embodiments, the autoimmune disorder is celiac disease. In certain embodiments, the biological fluid is selected from the group consisting of: blood, serum, plasma, bile, mucus, pus, or urine.

In some embodiments, the invention comprises an isolated peptide comprising an epitope identified by the method described herein.

In some embodiments, the invention comprises a method of treating a disorder, comprising administering a composition comprising the isolated peptide identified by the method described herein to a subject suspected of having the disorder. In one embodiment, the disorder is an autoimmune disease or an infectious disease. In some embodiments, the autoimmune disorder is celiac disease. In certain embodiments, the peptide is part of a vaccine. In some embodiments, the peptide is administered to the subject in combination with an adjuvant.

In some embodiments, the invention comprises a peptide array for diagnosing celiac disease in a suspect suspected of having celiac disease, comprising: a set of peptides comprising a set of epitope sequences that bind to an antibody associated with celiac disease; and a set of peptide sequences comprising an epitope sequence that binds to an inflammatory response molecule associated with celiac disease. In some embodiments, the peptide array has a feature density of 10,000 peptides molecules per square centimeter.

In some embodiments, the invention comprises a substrate, comprising: a first layer, wherein the layer comprises a plurality of unprotected carboxylic acid side groups. In some embodiments, the first layer is a porous layer. In some embodiments, the carboxylic acid side groups are oriented in multiple directions on the surface of the porous layer.

In an embodiment, the first layer is coupled to a support layer. In an embodiment, the first layer is coupled to a silicon wafer. In certain embodiments, the porous layer comprises dextran. In other embodiments, the porous layer comprises porous silica. In an embodiment, the porous layer comprises pores of a pore size of about 2 nm to 100 μm. In an embodiment, the porous layer comprises a porosity of about 10-80%. In an embodiment, the porous layer comprises a thickness of about 0.01 μm to about 10,000 μm.

In some embodiments, the substrate further comprises a planar layer comprising a metal having an upper surface and a lower surface. In some embodiments, the first layer is coupled to the planar layer. In some embodiments, the first layer is coated on top of the planar layer. In some embodiments, the substrate further comprises a plurality of wells.

In an embodiment, the substrate further comprises a plurality of pillars operatively coupled to the planar layer in positionally-defined locations, wherein each pillar has a planar surface extended from the planar layer, wherein the distance between the surface of each pillar and the upper surface of the layer is between 1,000-5,000 angstroms, and wherein the plurality of pillars are present at a density of greater than 10,000/cm$^2$, and wherein the first layer is deposited on the planar surface of the pillars. In some embodiments, the surface area of each pillar surface is at least 1 μm$^2$. In some embodiments, the surface area of each pillar surface has a total area of less than 10,000 μm$^2$. In some embodiments, the distance between the surface of each pillar and the lower surface of the layer is 2,000-7,000 angstroms. In some embodiments, the planar layer is 1,000-2,000 angstroms thick. In some embodiments, the center of each pillar is at least 2,000 angstroms from the center of any other pillar. In some embodiments, the surface of each pillar is parallel to the upper surface of the planar layer. In some embodiments, the surface of each pillar is substantially parallel to the upper surface of the planar layer. In certain embodiments, the metal is chromium. In some embodiments, the metal is chromium, titanium, aluminum, tungsten, gold, silver, tin, lead, thallium, or indium. In some embodiments, the planar layer is at least 98.5-99% metal by weight. In some embodiments, the planar layer is a homogenous layer of metal. In some embodiments, each pillar comprises silicon dioxide or silicon nitride. In some embodiments, each pillar is at least 98-99% silicon dioxide by weight.

In some embodiments, the substrate comprises a linker molecule having a free amino terminus attached to at least one of the carboxylic acid groups. In some embodiments, the substrate comprises a linker molecule having a free carboxylic acid group attached to at least one of the carboxylic acid groups. In some embodiments, the substrate comprises a coupling molecule attached to at least one of the carboxylic acid groups. In some embodiments, the substrate comprises a polymer chain attached to at least one of the carboxylic acid groups. In certain embodiments, the polymer chain comprises a peptide chain. In some embodiments, the polymer chain is attached to at least one of the carboxylic acid groups via a covalent bond.

In some embodiments, the invention comprises a method for identifying a set of informative peptide sequences, comprising obtaining a dataset comprising quantitative data indicating specific binding of a ligand present in a sample obtained from a subject having a condition to a plurality of peptide sequences; determining, using a specifically programmed computer, a plurality of subsequences present in the plurality of peptide sequences; determining using the specifically programmed computer, the rank number of occurrences of the plurality of subsequences in the plurality of peptide sequences; and identifying the set of informative peptide sequences according to the determined ranking of the plurality of subsequences.

In certain embodiments, the method comprises obtaining a dataset comprising quantitative data indicating specific binding of the ligand present in a plurality of samples obtained from subjects having the condition to a plurality of informative peptides each informative peptide comprising a plurality of informative peptide sequences; determining using a specifically programmed computer, the fraction of samples specifically binding to each of the informative peptides; and identifying according to the determining a subset of informative peptides capable of specifically binding to at least 50% of the samples.

In one embodiment, the condition is an autoimmune condition, an infectious disease condition, or a cancer. In some embodiments, the condition is an autoimmune condition. In certain embodiments, the autoimmune condition is celiac disease, lupus erythematosis, or rheumatoid arthritis.

In some embodiments, the subset of informative peptides is capable of specifically binding to at least 60%, at least 70%, at least 80%, or at least 90% of the samples.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 10 shows the normalized signal intensity for all twenty amino acids grown at each layer (total of 12 layers) on each wafer.

FIG. 16 shows the "deamidation" of peptide sequences (SEQ ID NOS: 46, 50, 47, 51, 52, 47, and 53, respectively, in order of appearance) from alpha gliadin.

FIG. 18 shows the binding of an IgA from a celiac positive sample to sequences comprising the epitopes combined according to the matrix.

FIG. 19 shows the binding of an IgG from a celiac positive sample to sequences comprising the epitopes combined according to the matrix.

FIG. 29 depicts coating of the wafers with amino acid from one of the first set of a plurality of reservoirs comprising the selected amino acid according to the process flow.

FIG. 30 depicts coating of the wafers with amino acid from one of the second set of a plurality of reservoirs comprising the selected amino acid according to the process flow.

DETAILED DESCRIPTION

Figure 1:
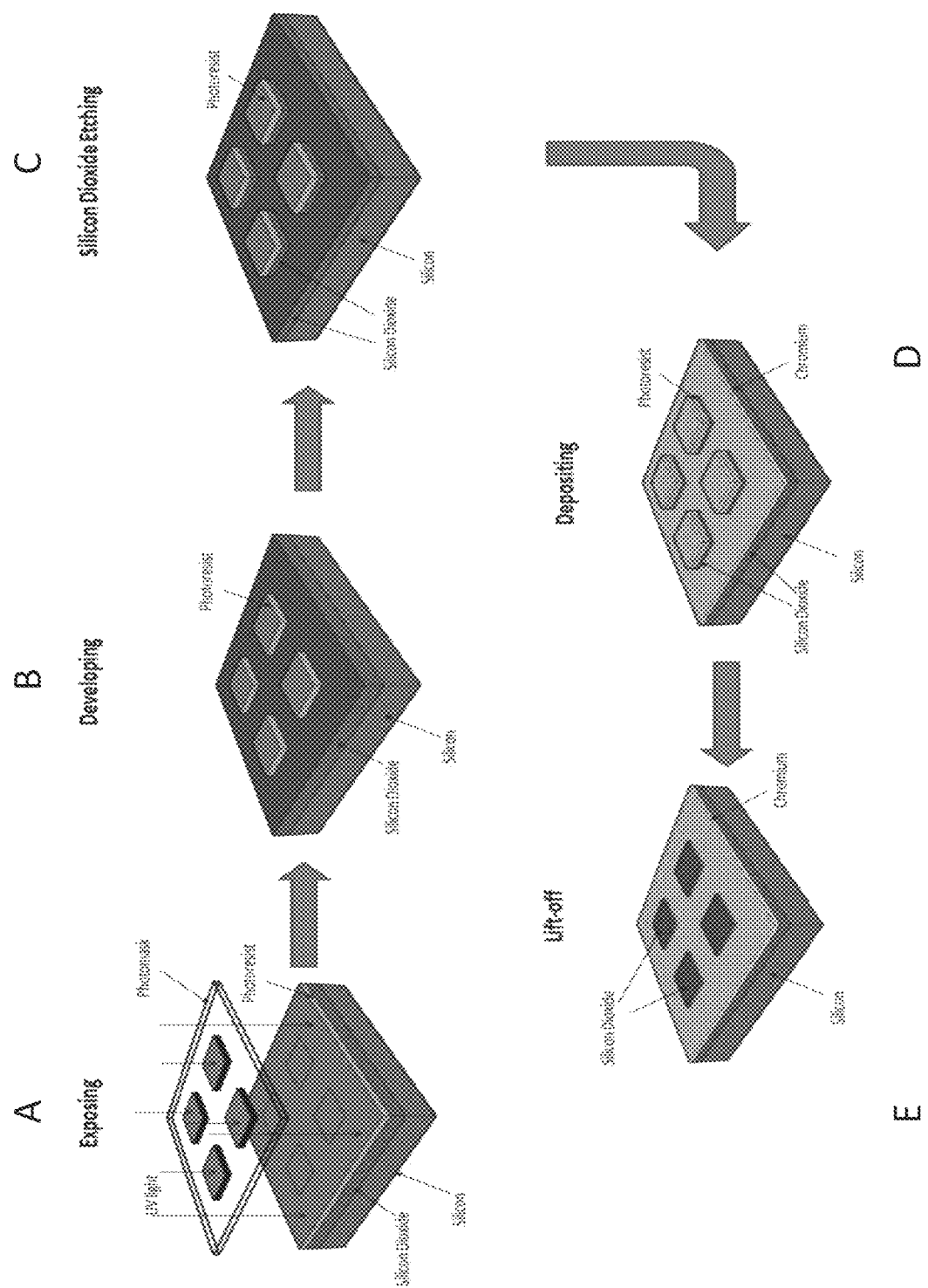
FIG. 1 shows a method of manufacturing a substrate.

Terms used in the claims and specification are defined as set forth below unless otherwise specified.

As used herein the term "wafer" refers to a slice of semiconductor material, such as silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 µm to 775 µm.

As used herein the term "photoresist" or "resist" or "photoactive material" refers to a light-sensitive material that changes its solubility in a solution when exposed to ultra violet or deep ultra violet radiation. Photoresists are organic or inorganic compounds that are typically divided into two types: positive resists and negative resists. A positive resist is a type of photoresist in which the portion of the photoresist that is exposed to light becomes soluble to the photoresist developer. The portion of the photoresist that is unexposed remains insoluble to the photoresist developer. A negative resist is a type of photoresist in which the portion of the photoresist that is exposed to light becomes insoluble to the photoresist developer. The unexposed portion of the photoresist is dissolved by the photoresist developer.

As used herein the term "photomask" or "reticle" or "mask" refers to an opaque plate with transparent patterns or holes that allow light to pass through. In a typical exposing process, the pattern on a photomask is transferred onto a photoresist.

As used herein the term "coupling molecule" or "monomer molecule" includes any natural or artificially synthesized amino acid with its amino group protected with a fluorenylmethyloxycarbonyl group or a t-butoxycarbonyl group. These amino acids may have their side chains protected as an option. Examples of coupling molecules include Boc-Gly-Oh, Fmoc-Trp-Oh. Other examples are described below.

As used herein the term "coupling" or "coupling process" or "coupling step" refers to a process of forming a bond between two or more molecules such as a linking molecule or a coupling molecule. A bond can be a covalent bond such as a peptide bond. A peptide bond can be a chemical bond formed between two molecules when the carboxyl group of one coupling molecule reacts with the amino group of the other coupling molecule, releasing a molecule of water ($H_2O$). This is a dehydration synthesis reaction (also known as a condensation reaction), and usually occurs between amino acids. The resulting CO—NH bond is called a peptide bond, and the resulting molecule is an amide.

As used herein the terms "biomolecule," "polypeptide," "peptide," or "protein" are used interchangeably to describe a chain or polymer of amino acids that are linked together by bonds. Accordingly, the term "peptide" as used herein includes a dipeptide, tripeptide, oligopeptide, and polypeptide. The term "peptide" is not limited to any particular number of amino acids. In some aspects, a peptide contains about 2 to about 50 amino acids, about 5 to about 40 amino acids, or about 5 to about 20 amino acids. A molecule, such as a protein or polypeptide, including an enzyme, can be a "native" or "wild-type" molecule, meaning that it occurs naturally in nature; or it may be a "mutant," "variant," "derivative," or "modification," meaning that it has been made, altered, derived, or is in some way different or changed from a native molecule or from another molecule such as a mutant.

As used herein the term "linker molecule" or "spacer molecule" includes any molecule that does not add any functionality to the resulting peptide but spaces and extends out the peptide from the substrate, thus increasing the distance between the substrate surface and the growing peptide. This generally reduces steric hindrance with the substrate for reactions involving the peptide (including uni-molecular folding reactions and multi-molecular binding reactions) and so improves performance of assays measuring one or more aspects of peptide functionality.

As used herein the term "developer" refers to a solution that can selectively dissolve the materials that are either exposed or not exposed to light. Typically developers are water-based solutions with minute quantities of a base added. Examples include tetramethyl ammonium hydroxide in water-based developers. Developers are used for the initial pattern definition where a commercial photoresist is used. Use of developers is described in Example 1 below.

As used herein the term "protecting group" includes a group that is introduced into a molecule by chemical modification of a functional group in order to obtain chemoselectivity in a subsequent chemical reaction. Chemoselectivity refers to directing a chemical reaction along a desired path to obtain a pre-selected product as compared to another. For example, the use of tboc as a protecting group enables chemoselectivity for peptide synthesis using a light mask and a photoacid generator to selectively remove the protecting group and direct pre-determined peptide coupling reactions to occur at locations defined by the light mask.

As used herein the term "microarrays" refers to a substrate on which different probe molecules of protein or specific DNA binding sequences have been affixed at separate locations in an ordered manner thus forming a microscopic array.

As used herein the term "microarray system" refers to a system usually comprised of biomolecular probes formatted on a solid planar surface like glass, plastic or silicon chip plus the instruments needed to handle samples (automated robotics), to read the reporter molecules (scanners) and analyze the data (bioinformatic tools).

As used herein the term "patterned region" or "pattern" or "location" refers to a region on the substrate on which are grown different features. These patterns can be defined using photomasks.

As used herein the term "derivatization" refers to the process of chemically modifying a surface to make it suitable for biomolecular synthesis. Typically derivatization includes the following steps: making the substrate hydrophilic, adding an amino silane group, and attaching a linker molecule.

As used herein the term "capping" or "capping process" or "capping step" refers to the addition of a molecule that prevents the further reaction of the molecule to which it is attached. For example, to prevent the further formation of a peptide bond, the amino groups are typically capped with an acetic anhydride molecule.

As used herein the term "diffusion" refers to the spread of a chemical through random motion from regions of higher concentration to regions of lower concentration.

As used herein the term "dye molecule" refers to a dye which typically is a colored substance that can bind to a substrate. Dye molecules can be useful in detecting binding between a feature on an array and a molecule of interest.

As used herein, the terms "immunological binding" and "immunological binding properties" refer to the type of non-covalent interactions that occurs between an immunoglobulin molecule (or variant thereof such as an scFv) and an antigen for which the immunoglobulin is specific.

As used herein the term "biological sample" refers to a sample derived from biological tissue or fluid that can be assayed for an analyte(s) of interest. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect analyte(s) of interest in samples from any organism (e.g., mammal, bacteria, virus, algae, or yeast) or mammal, such as dogs, cats, sheep, cattle, and pigs. The sample may be pretreated as necessary by dilution in an appropriate buffer solution or concentrated, if desired.

As used herein, the term "assay" refers to a type of biochemical test that measures the presence or concentration of a substance of interest in solutions that can contain a complex mixture of substances.

The term "subject' as used herein may refer to a human or any other animal having a disorder for testing, diagnosis or treatment.

The term "antigen" as used herein refers to a molecule that triggers an immune response by the immune system of a subject, e.g., the production of an antibody by the immune system and/or activation of the cellular arm of the immune system (e.g., activation of phagocytes, natural killer cells, and antigen-specific cytotoxic T-lymphocytes, along with release of various cytokines in response to an antigen). Antigens can be exogenous, endogenous or auto antigens. Exogenous antigens are those that have entered the body from outside through inhalation, ingestion or injection. Endogenous antigens are those that have been generated within previously-normal cells as a result of normal cell metabolism, or because of viral or intracellular bacterial infection. Auto antigens are those that are normal protein or protein complex present in the host body but can stimulate an immune response.

As used herein the term "epitope" or "immunoactive regions" refers to distinct molecular surface features of an antigen capable of being bound by component of the adaptive immune system, e.g., an antibody or T cell receptor. Antigenic molecules can present several surface features that can act as points of interaction for specific antibodies. Any such distinct molecular feature can constitute an epitope. Therefore, antigens have the potential to be bound by several distinct antibodies, each of which is specific to a particular epitope.

As used herein the term "antibody" or "immunoglobulin molecule" refers to a molecule naturally secreted by a particular type of cells of the immune system: B cells. There are five different, naturally occurring isotypes of antibodies, namely: IgA, IgM, IgG, IgD, and IgE.

As used herein the term "immune-related molecule" refers to a biological molecule involved in the activation or regulation of an immune response. These include, for example, an antibody, T cell receptor, or MHC complex (e.g., human leukocyte antigen).

As used herein, the term "inflammatory response molecule" refers to molecules that signal or mediate an inflammatory response, e.g., cytokines such as interleukin and tumor necrosis factor. Inflammatory response molecules include, for example, pro-inflammatory molecules.

As used herein, the term "autoimmune disorder" refers to any of a large group of diseases characterized by abnormal functioning of the immune system that causes a subject's immune system to damage the subject's own tissues. Celiac disorder, lupus erythematosis, and rheumatoid arthritis are examples of autoimmune disorders. Autoimmune disorders may be induced by environmental factors.

The term "percent identity" or "percent sequence identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

It must be noted that, as used in the specification and the appended claims, the singular forms "a," "an," and "the" include plural referents unless the context clearly dictates otherwise.

Compositions

Formulations

Disclosed herein are formulations such as photoactive formulations (e.g., photoresist formulations), coupling formulations, and linker formulations. These formulations can be useful in the manufacture and/or use of, e.g., substrates and/or peptide arrays disclosed herein. Generally the components of each formulation disclosed herein are soluble in water at room temperature (app. 25° C.).

Photoactive Formulations

Disclosed herein are photoactive formulations. In one aspect, a photoactive formulation can include a chemical amplification resist formulation. In chemical amplification (CA) resists, the primary photochemical event produces a mobile catalyst that, typically during later postexposure baking (PEB), goes on to induce a cascade of material transforming secondary catalytic events within a 5-25 nm radius. Such chemical amplification thus makes possible an overall quantum yield (the number of material reactions divided by number of absorbed photons) of up to several hundred. A CA resist typically contains a small amount (app. 1-5% by weight) of radiation-sensitive catalyst precursor, e.g., a photoacid generator (PAG); a plurality of chemical groups that can react by elimination, addition, or rearrangement in the presence of catalyst; a polymer matrix able to disperse other components in a smooth clear film; and optional additives to improve performance or processability, e.g., surfactants, photosensitizers, and etch resistors.

In some aspects, a photoactive formulation is not chemically amplified, i.e., all acid generated is consumed in the reaction (e.g., all the tboc is deprotected and acid is consumed in the reaction). A tboc protected amino acid can be added along with a photoresist formulation to verify if chemical amplification occurs. In some aspects, photosensitizers are optional when 248 nm is used.

In some aspects, a photoactive formulation includes a water soluble photoacid generator and a water soluble photo sensitizer in a polymer matrix dispersed in water. In some aspects, the polymer in the composition of the photoresist is generally inert and non-crosslinking but the photo reactive components will readily generate sufficient quantities of photoacid upon exposure in a deep ultra violet radiation tool to bring about a desired reaction to produce a product at acceptable yield.

In some aspects, a photoactive formulation can include various components such as a water soluble photosensitizer, a water soluble photo active compound, a water soluble polymer, and a solvent. Specific examples of photoactive formulations are shown in Table 1.

Photosensitizers are generally added to a formulation to increase the sensitivity of the photoacid generator and bring the absorption spectrum of the formulation near deep UV (248 nm). In some aspects, a water soluble photosensitizer can be a thioxanthenone. In some aspects, a general thioxanthenone structure is shown below:

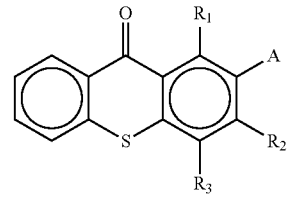

In some aspects, the A, $R_1$, $R_2$, and $R_3$ groups of the thioxanthenone structure shown above can be:

1.
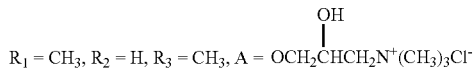

2.
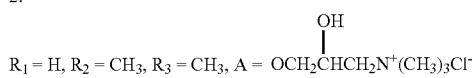

-continued

3.
$R_1 = CH_3, R_2 = H, R_3 = CH_3, A = OCH_2CH_2CH_2N^+(C_2H_5)_3Br^-$
4.
$R_1 = H, R_2 = CH_3, R_3 = CH_3, A = OCH_2CH_2CH_2N^+(C_2H_5)_3Br^-$
5.
$R_1 = CH_3, R_2 = H, R_3 = CH_3, A = OCH_2CH_2CH_2SO_3Na$
6.
$R_1 = H, R_2 = CH_3, R_3 = CH_3, A = OCH_2CH_2CH_2SO_3Na$
7.

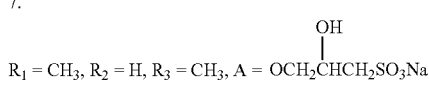

$R_1 = CH_3, R_2 = H, R_3 = CH_3, A = OCH_2CHCH_2SO_3Na$ (with OH)
8.

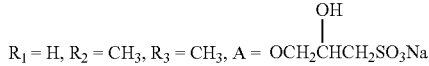

$R_1 = H, R_2 = CH_3, R_3 = CH_3, A = OCH_2CHCH_2SO_3Na$ (with OH)

In some aspects, a water soluble photosensitizer can be about 0.5-5% by weight of the total formulation concentration. In some aspects, a water soluble photosensitizer can be about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some aspects, a water soluble photoactive compound can be a photoacid generator (PAG) or a photobase generator (PBG). Photoacid generators (or PAGs) are cationic photoinitiators. A photoinitiator is a compound especially added to a formulation to convert absorbed light energy, UV or visible light, into chemical energy in the form of initiating species, e.g., free radicals or cations. Cationic photoinitiators are used extensively in optical lithography. The ability of some types of cationic photo initiators to serve as latent photochemical sources of very strong protonic or Lewis acids is generally the basis for their use in photo imaging applications. In some aspects, a photoacid generator is a water soluble iodonium salt, a water soluble polonium salt, or a water soluble sulfonium salt. In some aspects, a photoacid generator is (4-Methoxyphenyl)phenyliodonium or trifluoromethanesulfonate. In some aspects, a photoacid generator is (2,4-dihydroxyphenyl)dimethylsulfonium triflate or (4 methoxyphenyl)dimethylsulfonium triflate, shown below:

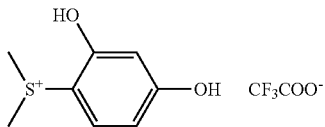

In some aspects, a photoacid generator is iodonium and sulfonium salts of triflates, phosphates and/or antimonates. In some aspects, a photoacid generator is about 0.5-5% by weight of the total formulation concentration. In some aspects, a photoacid generator is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some aspects, a water soluble polymer is a water soluble non-crosslinking inert polymer. In some aspects, a water soluble polymer is a polyvinyl pyrrolidone. The general structure of polyvinyl pyrrolidone is as follows, where n is any positive integer greater than 1:

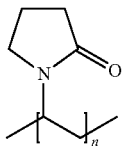

In some aspects, a water soluble polymer is a polymer of vinyl pyrrolidone. In some aspects, a water soluble polymer is polyvinyl pyrrolidone. Poly vinyl pyrrollidone is soluble in water and other polar solvents. When dry it is a light flaky powder, which generally readily absorbs up to 40% of its weight in atmospheric water. In solution, it has excellent wetting properties and readily forms films.

In some aspects, a water soluble polymer is about 0.5-5% by weight of the total formulation concentration. In some aspects, a water soluble polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some aspects, a solvent is water, ethyl lactate, or a combination thereof. In some aspects, ethyl lactate can be dissolved in water to more than 50% to form a solvent. In some aspects, a solvent can be about 10% propylene glycol methyl ether acetate (PGMEA) and about 90% DI water. In some aspects, a solvent can include up to about 20% PGMEA. In some aspects, the solvent is about 80-90% by weight of the total formulation concentration. In some aspects, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some aspects, a formulation can contain a tboc group that helps in chemical amplification of the initial acid generated upon post exposure baking. Thus, the formulation can include a tboc protected amino acid, e.g., in order to enhance the chemical amplification during post-exposure bake. In some aspects, this tboc protected amino acid would make up about 0.5-1% by weight of the formulation. In some aspects, a protected amino acid is about 0.5-5% by weight of the total formulation concentration. In some aspects, a protected amino acid is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In any of the combinations above, the formulation can be completely water strippable even after photo exposure and bake. Thus, in some aspects, only water is used to wash away the photoactive formulation after exposure and post bake.

Linker Formulations

Also disclosed herein is a linker formulation. A linker formulation can include components such as a solvent, a water soluble polymer, a water soluble linker molecule, and a water soluble coupling reagent. In some aspects, the polymer is 1% by weight polyvinyl alcohol and 2.5% by weight poly vinyl pyrrolidone, the linker molecule is 1.25% by weight polyethylene oxide, the coupling reagent is 1% by weight 1-ethyl-3-(3-dimethylaminopropyl) carbodiimide, and the solvent includes water. In some aspects, the polymer is 0.5-5% by weight polyvinyl alcohol and 0.5-5% by weight poly vinyl pyrrollidone, the linker molecule is 0.5-5% by weight polyethylene oxide, the coupling reagent is 0.5-5% by weight 1-ethyl-3-(3-dimethylaminopropyl) carbodiimide, and the solvent includes water.

In some aspects, the solvent is water, an organic solvent, or a combination thereof. In some aspects, the organic solvent is N Methyl pyrrolidone, Di methyl formamide, Di chloromethane, Di methyl sulfoxide, or a combination thereof. In some aspects, the solvent is about 80-90% by weight of the total formulation concentration. In some aspects, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some aspects, a water soluble polymer is a polyvinyl pyrrolidone and/or a polyvinyl alcohol. The general structure of polyvinyl alcohol is as follows, where n is any positive integer greater than 1:

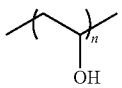

In some aspects, a water soluble polymer is about 0.5-5% by weight of the total formulation concentration. In some aspects, a water soluble polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some aspects, a coupling reagent is a water soluble carbodimide. In some aspects, a coupling reagent is a water soluble triazole. In some aspects, a coupling reagent is 1-ethyl-3-(3-dimethylaminopropyl) carbodiimide. In some aspects, a coupling reagent is about 0.5-5% by weight of the total formulation concentration. In some aspects, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

A linker molecule can be a molecule inserted between a surface disclosed herein and peptide that is being synthesized via a coupling molecule. A linker molecule does not necessarily convey functionality to the resulting peptide, such as molecular recognition functionality, but can instead elongate the distance between the surface and the peptide to enhance the exposure of the peptide's functionality region(s) on the surface. In some aspects, a linker can be about 4 to about 40 atoms long to provide exposure. The linker molecules can be, for example, aryl acetylene, ethylene glycol oligomers containing 2-10 monomer units (PEGs), diamines, diacids, amino acids, and combinations thereof. Examples of diamines include ethylene diamine and diamino propane. Alternatively, linkers can be the same molecule type as that being synthesized (e.g., nascent polymers or various coupling molecules), such as polypeptides and polymers of amino acid derivatives such as for example, amino hexanoic acids. In some aspects, a linker molecule is a molecule having a carboxylic group at a first end of the molecule and a protecting group at a second end of the molecule. In some aspects, the protecting group is a t-Boc protecting group or an F-Moc protecting group. In some aspects, a linker molecule is or includes an aryl acetylene, a polyethyleneglycol, a nascent polypeptide, a diamine, a diacid, a peptide, or combinations thereof. In some aspects, a linker molecule is about 0.5-5% by weight of the total formulation concentration. In some aspects, a linker molecule is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

The unbound portion of a linker molecule, or free end of the linker molecule, can have a reactive functional group which is blocked, protected, or otherwise made unavailable for reaction by a removable protective group, e.g., t-Boc or F-Moc as noted above. The protecting group can be bound to a monomer, a polymer, or a linker molecule to protect a reactive functionality on the monomer, polymer, or linker molecule. Protective groups that can be used include all acid and base labile protecting groups. For example, peptide amine groups can be protected by t-butoxycarbonyl (t-BOC or BOC) or benzyloxycarbonyl (CBZ), both of which are acid labile, or by 9-fluorenylmethoxycarbonyl (FMOC), which is base labile.

Additional protecting groups that can be used include acid labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha,alpha-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9 fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio) carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl. (See also, Greene, T. W., Protective Groups in Organic Synthesis, Wiley-Interscience, NY, (1981)).

Coupling Formulations

Also disclosed are coupling formulations. In some aspects, a coupling formulation can include components such as a solvent, a water soluble polymer, a water soluble coupling molecule, a water soluble neutralization reagent, and a water soluble coupling reagent. In some aspects, coupling formulations are shown in Table 2.

In some aspects, a solvent is water, an organic solvent, or combination thereof. In some aspects, the organic solvent is N Methyl pyrrolidone, di methyl formamide or combinations thereof.

In some aspects, a polymer is a water soluble vinyl pyrrolidone or a water soluble vinyl alcohol. In some aspects, a polymer is 2.5-5% by weight of the total formulation concentration. In some aspects, a polymer is about 0.5-5% by weight of the total formulation concentration. In some aspects, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some aspects, a neutralization reagent can include Hunig's base. The structure of Hunig's base is:

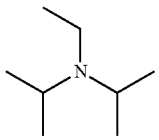

In some aspects, a neutralization reagent is 1-2% by weight of the total formulation concentration. In some aspects, a neutralization reagent is about 0.5-5% by weight of the total formulation concentration. In some aspects, a neutralization reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

The coupling molecules can include amino acids. In some instances all peptides on an array described herein are composed of naturally occurring amino acids. In others, peptides on an array described herein can be composed of a combination of naturally occurring amino acids and non-naturally occurring amino acids. In other cases, peptides on an array can be composed solely from non-naturally occurring amino acids. Non-naturally occurring amino acids include peptidomimetics as well as D-amino acids. The R group can be found on a natural amino acid or a group that is similar in size to a natural amino acid R group. Additionally, unnatural amino acids, such as beta-alanine, phenylglycine, homoarginine, aminobutyric acid, aminohexanoic acid, aminoisobutyric acid, butylglycine, citrulline, cyclohexylalanine, diaminopropionic acid, hydroxyproline, norleucine, norvaline, ornithine, penicillamine, pyroglutamic acid, sarcosine, and thienylalanine can also be incorporated. These and other natural and unnatural amino acids are available from, for example, EMD Biosciences, Inc., San Diego, Calif. In some aspects, a coupling molecule comprises a naturally occurring or artificial amino acid or polypeptide. Examples of coupling molecules include Boc-Glycine-OH and Boc-Histine-OH. In some aspects, the artificial amino acid is a D-amino acid. In some aspects, a coupling molecule is 1-2% by weight of the total formulation concentration. In some aspects, a coupling molecule is about 0.5-5% by weight of the total formulation concentration. In some aspects, a coupling molecule is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration. In some aspects, a coupling molecule comprises a protected side group, e.g., a side group protected via t-Boc or F-Moc chemistry. In most instances, increasing the concentration of a coupling molecule provides the best performance.

In some aspects, a coupling reagent is water soluble carbodimide or water soluble triazole. In some aspects, a coupling reagent is 2-4% by weight of the total formulation concentration. In some aspects, a coupling reagent is about 0.5-5% by weight of the total formulation concentration. In some aspects, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In any of the combinations above, the formulation can be completely water strippable.

Substrates

Also disclosed herein are substrates. In some aspects, a substrate can include a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about 10,000/cm$^2$. An example of a substrate is shown in FIG. 1.

In some aspects, the distance between the surface of each pillar and the upper surface of the later can be between about less than 1,000, 2,000, 3,000, 3,500, 4,500, 5,000, or greater than 5,000 angstroms (or any integer in between).

In some aspects, the surface of each pillar is parallel to the upper surface of the layer. In some aspects, the surface of each pillar is substantially parallel to the upper surface of the layer.

In some aspects, the plurality of pillars are present at a density of greater than 500, 1,000, 2,000, 3,000, 4,000, 5,000, 6,000, 7,000, 8,000, 9,000, 10,000, 11,000, or 12,000/cm$^2$ (or any integer in between). In some aspects, the plurality of pillars are present at a density of greater than 10,000/cm$^2$. In some aspects, the plurality of pillars are present at a density of about 10,000/cm$^2$ to about 2.5 million/cm$^2$ (or any integer in between). In some aspects, the plurality of pillars are present at a density of greater than 2.5 million/cm$^2$.

In some aspects, the surface area of each pillar surface is at least 1 µm$^2$. In some aspects, the surface area of each pillar surface can be at least 0.1, 0.5, 12, 3, 4, 5, 6, 7, 8, 9, 10, 15, 20, 25, 30, 35, 40, 45, or 50 µm$^2$ (or any integer in between). In some aspects, the surface area of each pillar surface has a total area of less than 10,000 µm$^2$. In some aspects, the surface area of each pillar surface has a total area of less than 500, 1,000, 2,000, 3,000, 4,000, 5,000, 6,000, 7,000, 8,000, 9,000, 10,000, 11,000, or 12,000 µm$^2$ (or any integer in between).

In some aspects, the distance between the surface of each pillar and the lower surface of the layer is 2,000-7,000 angstroms. In some aspects, the distance between the surface of each pillar and the lower surface of the layer is about less than 500, 1,000, 2,000, 3,000, 4,000, 5,000, 6,000, 7,000, 8,000, 9,000, 10,000, 11,000, 12,000, or greater than 12,000 angstroms (or any integer in between). In some aspects, the distance between the surface of each pillar and the lower surface of the layer is 7,000, 3,000, 4,000, 5,000, 6,000, or 7,000 angstroms (or any integer in between).

In some aspects, the layer is 1,000-2,000 angstroms thick. In some aspects, the layer is about less than 500, 1,000, 2,000, 3,000, 4,000, 5,000, 6,000, 7,000, 8,000, 9,000, 10,000, 11,000, 12,000, or greater than 12,000 angstroms thick (or any integer in between).

In some aspects, the center of each pillar is at least 2,000 angstroms from the center of any other pillar. In some aspects, the center of each pillar is at least about 500, 1,000, 2,000, 3,000, or 4,000 angstroms (or any integer in between) from the center of any other pillar. In some aspects, the center of each pillar is at least about 2 µm to 200 µm from the center of any other pillar.

In some aspects, the metal is chromium. In some aspects, the metal is chromium, titanium, aluminum, tungsten, gold, silver, tin, lead, thallium, indium, or a combination thereof. In some aspects, the layer is at least 98.5-99% metal. In some aspects, the layer is 100% metal. In some aspects, the layer is at least about greater than 90, 91, 92, 93, 94, 95, 96, 97, 98, 98.5, or 99% metal. In some aspects, the layer is a homogenous layer of metal.

In some aspects, at least one or each pillar comprises silicon. In some aspects, at least one or each pillar comprises silicon dioxide or silicon nitride. In some aspects, at least one or each pillar is at least 90, 91, 92, 93, 94, 95, 96, 97, 98, 98.5, or 99% silicon dioxide.

In some aspects, a substrate can include a linker molecule having a free amino terminus attached to the surface of each pillar. In some aspects, a substrate can include a linker molecule having a free amino terminus attached to the surface of at least one pillar. In some aspects, a substrate can include a linker molecule having a protecting group attached to the surface of each pillar. In some aspects, a substrate can include a linker molecule having a protecting group attached to the surface of at least one pillar. In some aspects, a substrate can include a coupling molecule attached to the surface of at least one pillar. In some aspects, a substrate can include a coupling molecule attached to the surface of each pillar. In some aspects, a substrate can include a water soluble polymer in contact with the surface of at least one of said pillars. In some aspects, a substrate can include a water soluble polymer in contact with the surface of each pillar. In some aspects, a substrate can include a gelatinous form of a water soluble polymer in contact with the surface of at least one of said pillars. In some aspects, a substrate can include a solid form of a water soluble polymer in contact with the surface of at least one of said pillars.

In some aspects, the surface of at least one of said pillars of the substrate is derivatized. In some aspects, a substrate can include a polymer chain attached to the surface of at least one of said pillars. In some aspects, the polymer chain comprises a peptide chain. In some aspects, the attachment to the surface of said at least one pillar is via a covalent bond.

In some aspects, the surface of each pillar is square or rectangular in shape. In some aspects, the substrate can be coupled to a silicon dioxide layer. The silicon dioxide layer can be about 0.5 µm to 3 µm thick. In some aspects, the substrate can be coupled to a wafer, e.g., a silicon wafer. The silicon dioxide layer can be about 700 µm to 750 µm thick.

In some aspects, a substrate can include a porous layer comprising functional groups for binding a first monomer building block.

Porous Layer Substrates

Porous layers which can be used are permeable, polymeric materials of porous structure which can have a functional group (which is native to the constituent polymer or which is introduced to the porous layer) for attachment of the first peptide building block. The functional group can comprise a free carboxylic acid group or a free amino group. For example, a porous layer can be comprised of porous silicon with functional groups for attachment of a polymer building block attached to the surface of the porous silicon. In another example, a porous layer may comprise a cross-linked polymeric material. In some embodiments, the porous layer may employ polystyrenes, saccharose, dextrans, polyacryloylmorpholine, polyacrylates, polymethylacrylates, polyacrylamides, polyacrylolpyrrolidone, polyvinylacetates, polyethyleneglycol, agaroses, sepharose, other conventional chromatography type materials and derivatives and mixtures thereof. In some embodiments, the porous layer building material is selected from: poly(vinyl alcohol), dextran, sodium alginate, poly(aspartic acid), poly(ethylene glycol), poly(ethylene oxide), poly(vinyl pyrrolidone), poly(acrylic acid), poly(acrylic acid)-sodium salt, poly(acrylamide), poly (N-isopropyl acrylamide), poly(hydroxyethyl acrylate), poly (acrylic acid), poly(sodium styrene sulfonate), poly(2-acrylamido-2-methyl-1-propanesulfonic acid), polysaccharides, and cellulose derivatives. Preferably the porous layer has a porosity of 10-80%. In one embodiment, the thickness of the porous layer ranges from 0.01 µm to about 1,000 µm. Pore sizes included in the porous layer may range from 2 nm to about 100 µm.

According to another aspect of the present invention there is provided a substrate comprising a porous polymeric material having a porosity from 10-80%, wherein reactive groups are chemically bound to the pore surfaces and are adapted in use to interact, e.g. by binding chemically, with a reactive species, e.g., deprotected monomeric building blocks or polymeric chains. In one embodiment the reactive group is a carboxylic acid group. The carboxylic acid group is free to bind, for example, an unprotected amine group of a peptide or polypeptide. In another embodiment, the reactive group is an amino group that is free to bind to, for example, an unprotected carboxylic acid group of a peptide or polypeptide.

In an embodiment, the porous layer is in contact with a support layer. The support layer comprises, for example, metal, plastic, silicon, silicon oxide, or silicon nitride. In another embodiment, the porous layer may be in contact with a patterned surface, such as on top of pillar substrates described above.

Arrays

Figure 2:
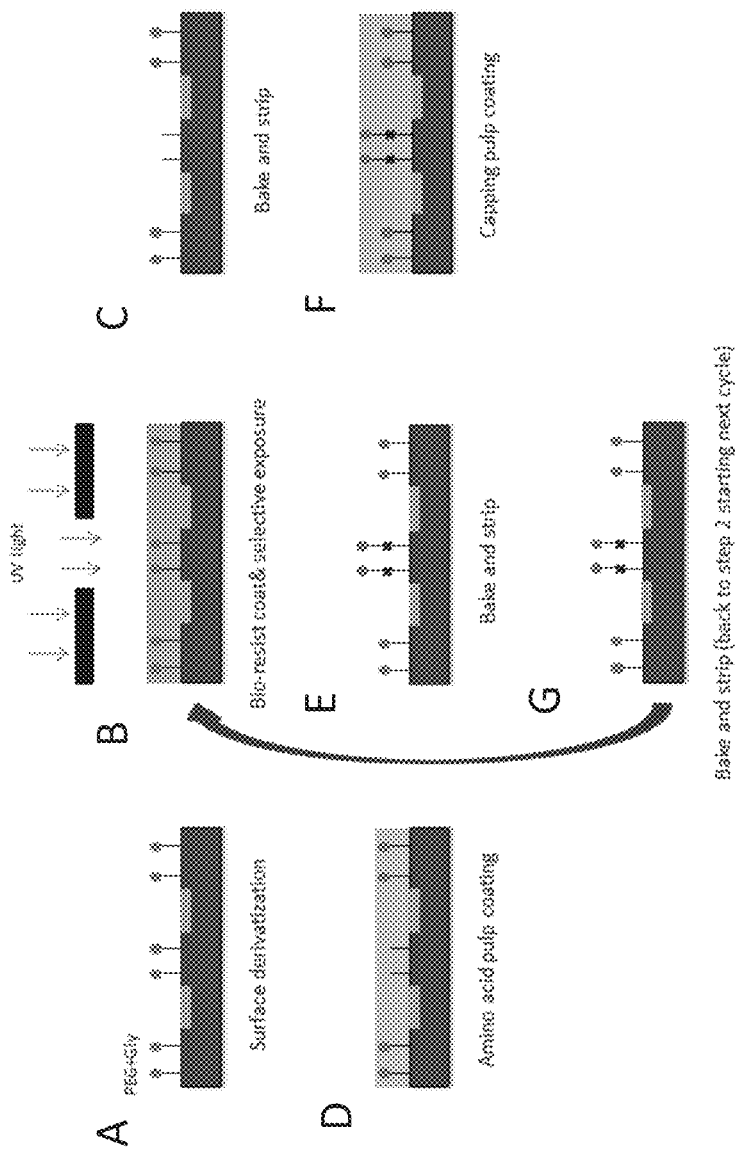
FIG. 2 shows a method of manufacturing an array.

Also disclosed herein are arrays. In some aspects, an array can be a two-dimensional array. In some aspects, a two-dimensional array can include features attached to a surface at positionally-defined locations, said features each comprising: a collection of peptide chains of determinable sequence and intended length, wherein within an individual feature, the fraction of peptide chains within said collection having the intended length is characterized by an average coupling efficiency for each coupling step of about 98%. An example of an array is shown in FIG. 2.

In some aspects, the average coupling efficiency for each coupling step is at least 98.5%. In some aspects, the average coupling efficiency for each coupling step is at least 99%. In some aspects, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%. In some embodiments, the coupling efficiency is substantially constant over each coupling cycle, and exceeds 98%. In some embodiments the average coupling efficiency exceeds 98% for each coupling step used to synthesize a 4-mer, or a 5-mer, or a 6-mer, or a 7-mer or longer polypeptide. In some embodiments coupling efficiency is substantially constant and exceeds 98% for each coupling step used to synthesize a 4-mer, or a 5-mer, or a 6-mer, or a 7-mer or longer polypeptide.

In some aspects, a surface includes a substrate disclosed herein. In some aspects, a surface is a material or group of materials having rigidity or semi-rigidity. In some aspects, a surface can be substantially flat, although in some aspects it can be desirable to physically separate synthesis regions for different molecules or features with, for example, wells, raised regions, pins, pillars, etched trenches, or the like. In certain aspects, a surface may be porous. Surface materials can include, for example, silicon, bio-compatible polymers such as, for example poly(methyl methacrylate) (PMMA) and polydimethylsiloxane (PDMS), glass, $SiO_2$ (such as, for example, a thermal oxide silicon wafer such as that used by the semiconductor industry), quartz, silicon nitride, functionalized glass, gold, platinum, and aluminum. Functionalized surfaces include for example, amino-functionalized glass, carboxy functionalized glass, and hydroxy functionalized glass. Additionally, a surface may optionally be coated with one or more layers to provide a second surface for molecular attachment or functionalization, increased or decreased reactivity, binding detection, or other specialized application. Surface materials and or layer(s) can be porous or non-porous. For example, a surface can be comprised of porous silicon. Additionally, the surface can be a silicon wafer or chip such as those used in the semiconductor device fabrication industry. In the case of a wafer or chip, a plurality of arrays can be synthesized on the wafer.

In some aspects, each peptide chain is from 5 to 60 amino acids in length. In some aspects, each peptide chain is at least 5 amino acids in length. In some aspects, each peptide chain is at least 5, 10, 15, 20, 25, 30, 35, 40, 45, 50, 55, or 60 amino acids in length. In some aspects, each peptide chain is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some aspects, each peptide chain comprises one or more L amino acids. In some aspects, each peptide chain comprises one or more D amino acids. In some aspects, each peptide chain comprises one or more naturally occurring amino acids. In some aspects, each peptide chain comprises one or more synthetic amino acids.

In some aspects, an array can include at least 1,000 different peptide chains attached to the surface. In some aspects, an array can include at least 10,000 different peptide chains attached to the surface. In some aspects, an array can include at least 100, 500, 1000, 2000, 3000, 4000, 5000, 6000, 7000, 8000, 9000, 10,000, or greater than 10,000 different peptide chains attached to the surface (or any integer in between).

In some aspects, each of the positionally-defined locations is at a different, known location that is physically separated from each of the other positionally-defined locations. In some aspects, each of the positionally-defined locations is a positionally-distinguishable location. In some aspects, each determinable sequence is a known sequence. In some aspects, each determinable sequence is a distinct sequence.

In some aspects, the features are covalently attached to the surface. In some aspects, said peptide chains are attached to the surface through a linker molecule or a coupling molecule.

In some aspects, the features comprise a plurality of distinct, nested, overlapping peptide chains comprising subsequences derived from a source protein having a known sequence. In some aspects, each peptide chain in the plurality is substantially the same length. In some aspects, each peptide chain in the plurality is the same length. In some aspects, each peptide chain in the plurality is at least 5 amino acids in length. In some aspects, each peptide chain in the plurality is at least 5, 10, 15, 20, 25, 30, 35, 40, 45, 50, 55, or 60 amino acids in length. In some aspects, each peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some aspects, at least one peptide chain in the plurality is at least 5 amino acids in length. In some aspects, at least one peptide chain in the plurality is at least 5, 10, 15, 20, 25, 30, 35, 40, 45, 50, 55, or 60 amino acids in length. In some aspects, at least one peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some aspects, each polypeptide in a feature is substantially the same length. In some aspects, each polypeptide in a feature is the same length. In some aspects, the features comprise a plurality of peptide chains each having a random, determinable sequence of amino acids.

Methods

Methods of Manufacturing Substrates

Also disclosed herein are methods for making substrates. In some aspects, a method of producing a substrate can include coupling a planar layer to a plurality of pillars, wherein the planar layer comprises a metal and has an upper surface and a lower surface, wherein the plurality of pillars are coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about 10,000/cm$^2$.

In some aspects, the surface of each pillar is parallel to the upper surface of the layer. In some aspects, the surface of each pillar is substantially parallel to the upper surface of the layer.

In some aspects, a method of preparing a substrate surface can include obtaining a surface comprising silicon dioxide and contacted with a photoactive formulation comprising a water soluble photosensitizer, a water soluble photo active compound, a water soluble polymer, and a solvent; and applying ultraviolet light to positionally-defined locations located on the top of the surface and in contact with the photoactive formulation, wherein the surface area of each positionally-defined location on the surface has a total area of less than about 10,000/μm$^2$. In some aspects, the method can include removing the photoactive formulation located external to the positionally-defined locations. In some aspects, the method can include reducing the thickness of the top of the surface located external to the positionally-defined locations. In some aspects, the method can include depositing a metal layer on the top of the surface with reduced thickness. In some aspects, the method can include removing the photoactive formulation in contact with the positionally-defined locations located on the top of the surface.

In one embodiment, FIGS. 1A-1E presents a process for producing a substrate.

Referring to FIG. 1A, the first step in the preparation of a substrate is priming a starting wafer in order to promote good adhesion between a photoactive formulation (e.g., a photoresist) and a surface. Wafer cleaning can also be performed, which can include steps such as oxidation, oxide strip, and an ionic clean. Typically deionized (DI) water rinse is used to remove contaminants on the wafer surface.

In wafer fabrication, silane deposition is generally needed to promote the chemical adhesion of an organic compound (photoresist) to a non-organic substrate (wafer). The silane acts as a sort of "bridge," with properties that will bond to both the photoresist and wafer surface. Typically, hexamethyldisilizane (HMDS) is used. HMDS is an organosilicon compound that is generally applied on heated substrates in gaseous phase in a spray module or in liquid phase through puddle and spin in a developer module followed by a bake step. In a puddle and spin method, HMDS is puddled onto the wafer for a specified time and then spun and baked at typical temperatures of 110-130° C. for 1-2 mins. In a spray module, vapors of HMDS are applied onto a heated wafer substrate at 200-220° C. for 30 s-50 s.

Referring to FIG. 1A, after wafer priming, the wafers can be coated with a deep ultra violet (DUV) photoresist in a photoresist coater module. DUV resists are typically polyhydroxystyrene-based polymers with a photoacid generator providing the solubility change. They can also comprise an optional photosensitizer. The matrix in the polymer consists of a protecting group for e.g., tboc attached to its end group.

The DUV resist is spin coated on the wafers in a photoresist coat module. This comprises a vacuum chuck held inside a cup. The wafers are mechanically placed on the chuck by, e.g., a robotic arm and then are spun at required speeds specified by the manufacturer to obtain the optimum thickness.

Referring to FIG. 1A, the wafers are pre-heated in a pre-heat module. The pre-heat module typically includes a hot plate that can be set to required temperatures for the corresponding DUV resist as specified by the manufacturer. The heating can also be done in a microwave for a batch of wafers.

Referring to FIG. 1A, the wafers are now exposed in a deep ultra violet radiation exposure tool through patterned photo masks.

Referring to FIG. 1A, the wafers are now heated in a post exposure bake module. This post exposure leads to chemical amplification. The resist manufacturers provide the typical post exposure bake temperature and time for their corresponding product. When a wafer coated with a DUV photoresist is exposed to 248 nm light source through a reticle, an initial photoacid or photobase is generated. The photoresist is baked to promote diffusion of the photoacid or photobase. The exposed portion of the resist becomes soluble to the developer thereby enabling patterning of 0.25 micron dimensions. A post exposure bake module comprises a hot plate set to the required temperatures as specified by the manufacturer. It can consist of three vacuum pins on which the wafers are placed by, e.g., a robotic arm. In other embodiments, the resist process does not use chemical amplification.

Referring to FIG. 1B, the wafers are now developed in a developer module. A developer module typically consists of a vacuum chuck that can hold wafers and pressurized nozzles that can dispense the developer solution on to the wafers. The dispense mode can be a puddle and spin mode or a spin and rinse mode. Puddle and spin mode means the wafers remain stationery on the chuck for about 30 sec to 1 minute when the developer solution is dispensed. This puddles the developer solution on top of the wafer. After a minute, it is spun away. In a spin and rinse mode, the developer solution is dispensed while the wafers are being spun.

Referring to FIG. 1C, the oxide is now etched away in those regions that are developed by means of a wet etch or a dry etch process. Etching is a process by which material is removed from the silicon substrate or from thin films on the substrate surface. When a mask layer is used to protect specific regions of the wafer surface, the goal of etching is to precisely remove the material that is not covered by the mask. Normally, etching is classified into two types: dry etching and wet etching. Wet etching uses liquid chemicals, primarily acids to etch material, whereas dry etching uses gases in an excited state to etch material. These methods are well known to skilled artisans. These processes can be controlled to achieve an etch depth of, e.g., 1000 A to 2000 A.

Referring to FIG. 1D, a metal is deposited on the wafers. This metal is typically chromium, titanium, or aluminum. In some embodiments the metals are deposited by a process called sputter deposition. Sputter deposition is a physical vapor deposition (PVD) method of depositing thin films by sputtering, that is ejecting, material from a "target," that is a source, which then deposits onto the wafers. The thickness of metal deposition is ensured to be at least 500 A on top of the substrate, if desired.

Referring to FIG. 1E, the photoresist in between the metal layer and the oxide can be lifted off by using the process diagrammed. In some aspects, the process includes lifting off the resist when the wafer has a metal layer without affecting the metal layer that previously has been deposited onto the silicon dioxide. This process results in lift off of the photoresist and metal deposited on the top surface of the substrate pillars, resulting in a silicon dioxide pillar rising above a metal-coated base that separates adjacent pillars. The wafers are submerged in an oxidizer solution overnight and then dipped in a Piranha solution for typically 1 hr. Piranha solution is a 1:1 mixture of sulfuric acid and hydrogen peroxide. This can be used to clean all the organic residues off the substrates. Since the mixture is a strong oxidizer, it will remove most of the organic matter, and it will also hydroxylate most surfaces (add OH groups), making them hydrophilic. This process can also include an additional step of plasma ashing.

Surface Derivatization

Substrates can be surface derivatized in a semiconductor module as explained in U.S. Pat. App. 20100240555, herein incorporated by reference, in its entirety, for all purposes. A typical substrate of the present invention has pillars of oxide ready to be surface derivatized. Surface derivatization is a method wherein an amino silane group is added to the substrate so that free amino groups are available for coupling the biomolecules. In some aspects, the first molecule to be attached to the surface derivatized substrate is a tboc protected Glycine. This coupling procedure is similar to a standard Merrifield solid phase peptide synthesis procedure which is generally known to one skilled in this art.

Methods of Manufacturing Arrays

Also disclosed herein are methods for manufacturing arrays. In some aspects, the arrays disclosed herein can be synthesized in situ on a surface, e.g., a substrate disclosed herein. In some instances, the arrays are made using photolithography. For example, masks can be used to control radiation or light exposure to specific locations on a surface provided with linker molecules having protecting groups. In the exposed locations, the protecting groups are removed, resulting in one or more newly exposed reactive moieties on the linker. The surface is then contacted with a solution containing a coupling molecule. The coupling molecule can have at least one site that is reactive with the newly exposed reactive moiety on the linker and at least a second reactive site protected by one or more protecting groups. The desired coupling molecule is then coupled to the unprotected linker molecules. The process can be repeated to synthesize a large number of features in specific or positionally-defined locations on a surface (see, for example, U.S. Pat. No. 5,143,854 to Pirrung et al., U.S. Patent Application Publication Nos. 2007/0154946 (filed on Dec. 29, 2005), 2007/0122841 (filed on Nov. 30, 2005), 2007/0122842 (filed on Mar. 30, 2006), 2008/0108149 (filed on Oct. 23, 2006), and 2010/0093554 (filed on Jun. 2, 2008), each of which is herein incorporated by reference).

In some aspects, a method of producing a two-dimensional array of features, can include obtaining a surface; and attaching the features to the surface, said features each comprising a collection of peptide chains of determinable sequence and intended length, wherein within an individual feature, the fraction of peptide chains within said collection having the intended length is characterized by an average coupling efficiency for each coupling step of at least about 98%. In some aspects, the features are attached to the surface using a coupling formulation, comprising a solvent, a water soluble polymer, a water soluble coupling molecule, a water soluble neutralization reagent, and a water soluble coupling reagent. In some aspects, the features are attached to the surface using a coupling formulation disclosed herein. In some aspects, the coupling formulation is stripped away using water.

In some aspects, a method of producing a two-dimensional array of features, can include obtaining a substrate comprising a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about 10,000/cm$^2$; and coupling through a series of coupling reactions the features to the plurality of pillars, said features each comprising a collection of peptide chains of determinable sequence and intended length, wherein within an individual feature, the fraction of peptide chains within said collection having the intended length is characterized by an average coupling efficiency for each coupling step of at least about 98%. In some embodiments, the coupling efficiency is substantially constant over each coupling cycle, and exceeds 98%. In some embodiments the average coupling efficiency exceeds 98% for each coupling step used to synthesize a 4-mer, or a 5-mer, or a 6-mer, or a 7-mer or longer polypeptide. In some embodiments the coupling efficiency is substantially constant and exceeds 98% for each coupling step used to synthesize a 4-mer, or a 5-mer, or a 6-mer, or a 7-mer or longer polypeptide. Coupling steps used to synthesize. In some aspects, the features are coupled to the pillars using a coupling formulation, comprising a solvent, a water soluble polymer, a water soluble coupling molecule, a water soluble neutralization reagent, and a water soluble coupling reagent. In some aspects, the features are coupled using a coupling formulation disclosed herein. In some aspects, the coupling formulation is stripped away using water. In some aspects, the surface of each pillar is parallel to the upper surface of the layer. In some aspects, the surface of each pillar is substantially parallel to the upper surface of the layer.

In some aspects, a method of preparing a substrate for attachment of features, can include obtaining a substrate comprising a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about 10,000/cm$^2$; and attaching one or more linker molecules to the plurality of pillars. In some aspects, the linker molecule is attached using a linker formulation, comprising a solvent, a water soluble polymer, a water soluble linker molecule, and a water soluble coupling reagent. In some aspects, the linker molecule is attached using a linker formulation disclosed herein. In some aspects, linker molecule comprises a protecting group. In some aspects, the surface of each pillar is parallel to the upper surface of the layer. In some aspects, the surface of each pillar is substantially parallel to the upper surface of the layer.

In some aspects, a method of preparing a surface for attachment of features, can include obtaining a surface and attaching a linker molecule to the surface using a linker formulation, comprising a solvent, a water soluble polymer, a water soluble linker molecule, and a water soluble coupling reagent. In some aspects, linker molecule comprises a protecting group.

In some aspects, a method of attaching a coupling reagent to a substrate, can include obtaining a substrate comprising a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein a linker molecule is attached to the surface of each pillar, and wherein the plurality of pillars are present at a density of greater than 10,000/cm$^2$; and attaching the coupling reagent to one or more linker molecules. In some aspects, the coupling reagent is attached to the one or more linker molecules using a coupling formulation, comprising: a solvent, a water soluble polymer, a water soluble coupling molecule, a water soluble neutralization reagent, and a water soluble coupling reagent. In some aspects, the coupling reagent is attached to the one or more linker molecules using a coupling formulation disclosed herein. In some aspects, at least one the linker molecule is a deprotected linker molecule. In some aspects, the coupling reagent is an amino acid. In some aspects, the coupling reagent comprises a protecting molecule. In some aspects, the coupling formulation is stripped away using water. In some aspects, the surface of each pillar is parallel to the upper surface of the layer. In some aspects, the surface of each pillar is substantially parallel to the upper surface of the layer.

In some aspects, a method of attaching a coupling reagent to a surface can include obtaining a surface having a linker molecule attached to the surface and attaching the coupling reagent to the linker molecule using a coupling formulation, comprising a solvent, a water soluble polymer, a water soluble coupling molecule, a water soluble neutralization reagent, and a water soluble coupling reagent. In some aspects, the linker molecule is a deprotected linker molecule. In some aspects, the coupling reagent is an amino acid. In some aspects, the coupling reagent comprises a protecting molecule. In some aspects, the coupling formulation is stripped away using water.

In one embodiment, FIGS. 2A through 2G describe a process of manufacturing an array.

Referring to FIGS. 2A and 2B, a derivatized surface (e.g., a surface derivatized wafer) with a linker molecule attached is spun coat with a photoactive formulation (photoresist) as described herein. The resist thickness can be 100 nm to 200 nm to enable better photoacid diffusion. Hence the spin speed and the speed of spinning can be modified to achieve the desired thickness of the resist.

Referring to FIG. 2B, the resist coat is now baked in a preheat module. The temperatures can be 65° C. to 85° C. for 60 sec to 90 sec. This step generally produces a uniform coat with the photoactive formulation as it involves water as a solvent.

Referring to FIG. 2B, the wafer is now exposed in a deep ultra violet scanner tool. The deep UV light is imaged through a photo mask that has a designed or a random pattern on it. In some aspects, disclosed herein is a method of selectively irradiating the known features on a substrate or surface to yield photoacid to deprotect the tboc present on the amino terminal of the linker/coupling molecule. This is possible with designed patterns on the photo masks that represent the equivalent of one single monomer of a known peptide or protein or polypeptide or antigen or antigenic determinant. The expose energy can be from 1 mJ/cm$^2$ to 100 mJ/cm$^2$ in order to produce enough photoacid. A photoacid generated can be triflic acid which is a super acid with $K_a = 8.0 \times 10^{14}$ mol/kg (pK$_a$~−15). Triflic acid owes many of its useful properties to its high thermal and chemical stability. Owing to its small molecular size, its diffusion is also less burdensome compared to many acids.

Referring to FIG. 2C, the wafer is post baked upon exposure in a post exposure bake module. Post exposure bake acts as a chemical amplification step. The baking step amplifies the initially generated photoacid and also enhances the rate of diffusion to the substrate. The substrate that is already surface derivatized with a linker molecule attached generally has a protecting group, for example t-boc, on it. As the photoacid reaches the substrate, it cleaves the protecting group and hence leaves the amino group of the linker molecule open to be coupled with the carboxylic acid group of a linker/coupling molecule. The post bake temperature can vary between 75° C. to 115° C., depending on the thickness of the photoresist, for at least 60 sec and not usually exceeding 120 sec.

Referring to FIG. 2C, the resist can now be stripped away. In some aspects, provided herein is a method of stripping the photoresist completely with DI water. This process is accomplished in a developer module. The wafer is spun on a vacuum chuck for, e.g., 60 seconds to 90 seconds and deionized water is dispensed through a nozzle for about 30 seconds.

Referring to FIG. 2D, a coupling formulation is applied on the wafer substrate. The coupling formulation can be prepared as described herein or as follows: a solvent, a polymer, a coupling molecule, a neutralizing base, and one or more coupling reagents. The solvent is generally water or includes water. A water soluble polymer is first dissolved in known quantities typically 2.5-5% by weight of the total solution concentration. Now the coupling molecule is added at 1-2% by weight of the total solution concentration. The neutralizing base is added at the same concentration as the coupling molecule and the coupling reagents at twice the concentration of the coupling molecule. The addition of neutralizing base along with the coupling formulation reduces a separate step in the entire sequence of biomolecular synthesis, as the photoacid left unreacted on the substrate can be neutralized before coupling. This not only reduces the time to complete a cycle of coupling but also improves the coupling efficiency. The coupling reagents can include a water soluble carbodiimide and a water soluble triazole that, e.g., prevents racemization of the coupling molecule.

The coupling formulation is applied on the wafer in a coupling spin module. A coupling spin module can typically have 20 nozzles or more to feed the coupling formulation. These nozzles can be made to dispense the coupling formulation by means of pressurizing the cylinders that hold these solutions or by a pump that dispenses the required amount. In some aspects, the pump is employed to dispense 5-8 cc of the coupling formulation onto the wafer substrate. The wafer is spun on a vacuum chuck for 15-30 s and the coupling formulation is dispensed. The spin speed can be set to 2000 to 2500 rpm.

Referring to FIG. 2E, the wafers are now baked in a coupling bake module. A coupling bake module is a hot plate set up specifically to receive wafers just after the coupling formulation is applied. In some aspects, provided herein is a method of baking the spin coated coupling formulation in a hot plate to accelerate the coupling or reaction efficiency. Hot plate baking generally reduces the coupling time for amino acids to less than two minutes with more than 95% coupling or reaction efficiency.

Referring to FIG. 2E, the by-products of the coupling reaction are now stripped away with DI water in a developer module. The wafer is spun on a vacuum chuck for 60 s to 90 s and DI water is dispensed through a nozzle for about 30 secs.

Referring to FIG. 2F, a cap film solution coat is applied on the wafer to prevent the unreacted amino groups on the substrate from reacting with the next coupling molecule. The cap film coat solution can be prepared as follows: a solvent, a polymer, and a coupling molecule. The solvent that can be used can be an organic solvent like N methyl pyrrolidone, di methyl formamide, or combinations thereof. The capping molecule is typically acetic anhydride and the polymer can be polyvinyl pyrrolidone, polyvinyl alcohol, polymethyl methacrylate, poly(methyl iso propenyl) ketone, or poly (2 methyl pentene 1 sufone).

This process is done in a capping spin module. A capping spin module can include one nozzle that can be made to dispense the cap film coat solution onto the wafer. This solution can be dispensed through pressurizing the cylinder that stores the cap film coat solution or through a pump that precisely dispenses the required amount. In some aspects, a pump is used to dispense around 5-8 cc of the cap coat solution onto the wafer substrate. The wafer is spun on a vacuum chuck for 15-30 s and the coupling formulation is dispensed. The spin speed is can be set to 2000 to 2500 rpm.

Referring to FIG. 2G, the wafers with the capping solution are baked in a cap bake module. A capping bake module is a hot plate set up specifically to receive wafers just after the capping film coat is applied. In some aspects, provided herein is a method of baking the spin coated capping coat solution in a hot plate to accelerate the capping reaction significantly. Hot plate baking generally reduces the capping time for amino acids to less than two minutes.

Referring to FIG. 2G, the byproducts of the capping reaction are stripped in a stripper module. A stripper module can include several nozzles, typically up to 10, set up to dispense organic solvents such as acetone, iso propyl alcohol, N methyl pyrrolidone, Di methyl formamide, DI water, etc. In some aspects, the nozzles can be designated for acetone followed by iso propyl alcohol to be dispensed onto the spinning wafer. The spin speed is set to be 2000 to 2500 rpm for around 20 s.

This entire cycle of steps from FIG. 2B through 2G can be repeated as desired with different coupling molecules each time to obtain a desired sequence.

Methods of Use

Also disclosed herein are methods of using substrates, formulations, and/or arrays. Uses of the arrays disclosed herein can include research applications, therapeutic purposes, medical diagnostics, and/or stratifying one or more patients or subjects.

Any of the arrays described herein can be used as a research tool or in a research application. In one aspect, arrays can be used for high throughput screening assays. For example, enzyme substrates (i.e., peptides on a peptide array described herein) can be tested by subjecting the array to an enzyme and identifying the presence or absence of enzyme substrate(s) on the array, e.g., by detecting at least one change among the features of the array.

Arrays can also be used in screening assays for ligand binding, to determine substrate specificity, or for the identification of peptides that inhibit or activate proteins. Labeling techniques, protease assays, as well as binding assays useful for carrying out these methodologies are generally well-known to one of skill in the art.

In some aspects, an array can be used to represent a known protein sequence as a sequence of overlapping peptides. For example, the amino acid sequence of a known protein is divided into overlapping sequence segments of any length and of any suitable overlapping frame, and peptides corresponding to the respective sequence segments are in-situ synthesized as disclosed herein. The individual peptide segments so synthesized can be arranged starting from the amino terminus of the known protein.

In some aspects, an array is used in a method wherein the antigenic representation of the array includes at least one region where the whole antigen sequence of a known protein is spanned via epitope sliding; the immunoactive regions of the antigen are determined by contacting one or more clinical samples on the array or a plurality of different arrays, and the set of peptide sequences required to represent the known protein antigen are reduced.

In some aspects, a sample is applied to an array having a plurality of random peptides. The random peptides can be screened and BLASTed to determine homologous domains with, e.g., a 90% or more identity to a given antigenic sequence. In some aspect, the whole antigenic sequence can then be synthesized and used to identify potential markers and/or causes of a disease of interest.

In some aspects, an array is used for high throughput screening of one or more genetic factors. Proteins associated with a gene can be a potential antigen and antibodies against these gene related proteins can be used to estimate the relation between gene and a disease.

In another example, an array can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, proteins (e.g., enzymes such as kinases), sugars, salts, fats, lipids, or ions.

Arrays can also be used for therapeutic purposes, e.g., identifying one or more bioactive agents. A method for identifying a bioactive agent can comprise applying a plurality of test compounds to an array and identifying at least one test compound as a bioactive agent. The test compounds can be small molecules, aptamers, oligonucleotides, chemicals, natural extracts, peptides, proteins, fragment of antibodies, antibody like molecules or antibodies. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In another aspect, an array can be used to identify drug candidates for therapeutic use. For example, when one or more epitopes for specific antibodies are determined by an assay (e.g., a binding assay such as an ELISA), the epitopes can be used to develop a drug (e.g., a monoclonal neutralizing antibody) to target antibodies in disease.

In one aspect, also provided are arrays for use in medical diagnostics. An array can be used to determine a response to administration of drugs or vaccines. For example, an individual's response to a vaccine can be determined by detecting the antibody level of the individual by using an array with peptides representing epitopes recognized by the antibodies produced by the induced immune response. Another diagnostic use is to test an individual for the presence of biomarkers, wherein samples are taken from a subject and the sample is tested for the presence of one or more biomarkers.

Arrays can also be used to stratify patient populations based upon the presence or absence of a biomarker that indicates the likelihood a subject will respond to a therapeutic treatment. The arrays can be used to identify known biomarkers to determine the appropriate treatment group. For example, a sample from a subject with a condition can be applied to an array. Binding to the array may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some aspects, a method of detecting the presence or absence of a protein of interest in a sample can include obtaining an array disclosed herein and contacted with a sample suspected of comprising the protein of interest; and determining whether the protein of interest is present in the sample by detecting the presence or absence of binding to one or more features of the array.

In some aspects, a method of identifying a vaccine candidate can include obtaining an array disclosed herein contacted with a sample derived from a subject previously administered the vaccine candidate, wherein the sample comprises a plurality of antibodies; and determining the binding specificity of the plurality of antibodies to one or more features of the array. In some aspects, the features comprise a plurality of distinct, nested, overlapping peptide chains comprising subsequences derived from a source protein having a known sequence.

In one embodiment, a method of diagnosing and treating an autoimmune disorder is provided. In one embodiment, use of the peptide chip to detecting multiplex antibodies in a serum sample is provided. In some aspects, this method is performed in a single assay. In some aspects, this method is performed on a single peptide chip. In one embodiment, this method provides the ability to detect multiple chemokines from an autoimmune disorder. In one embodiment, this method provides the ability to identify the subtype and severity of an autoimmune disorder.

In one embodiment, methods of diagnosing using the peptide chip have a reproducibility of $R^2$ greater than 0.95. In some embodiments, the methods of diagnosing an autoimmune disorder using the peptide chip have a specificity of greater than 0.99 and/or a sensitivity of greater than 0.99.

In one embodiment, the autoimmune disorder is celiac disease. In another embodiment, the autoimmune disorder is lupus erythematosis. In another embodiment, the autoimmune disorder is rheumatoid arthritis.

Figure 3:
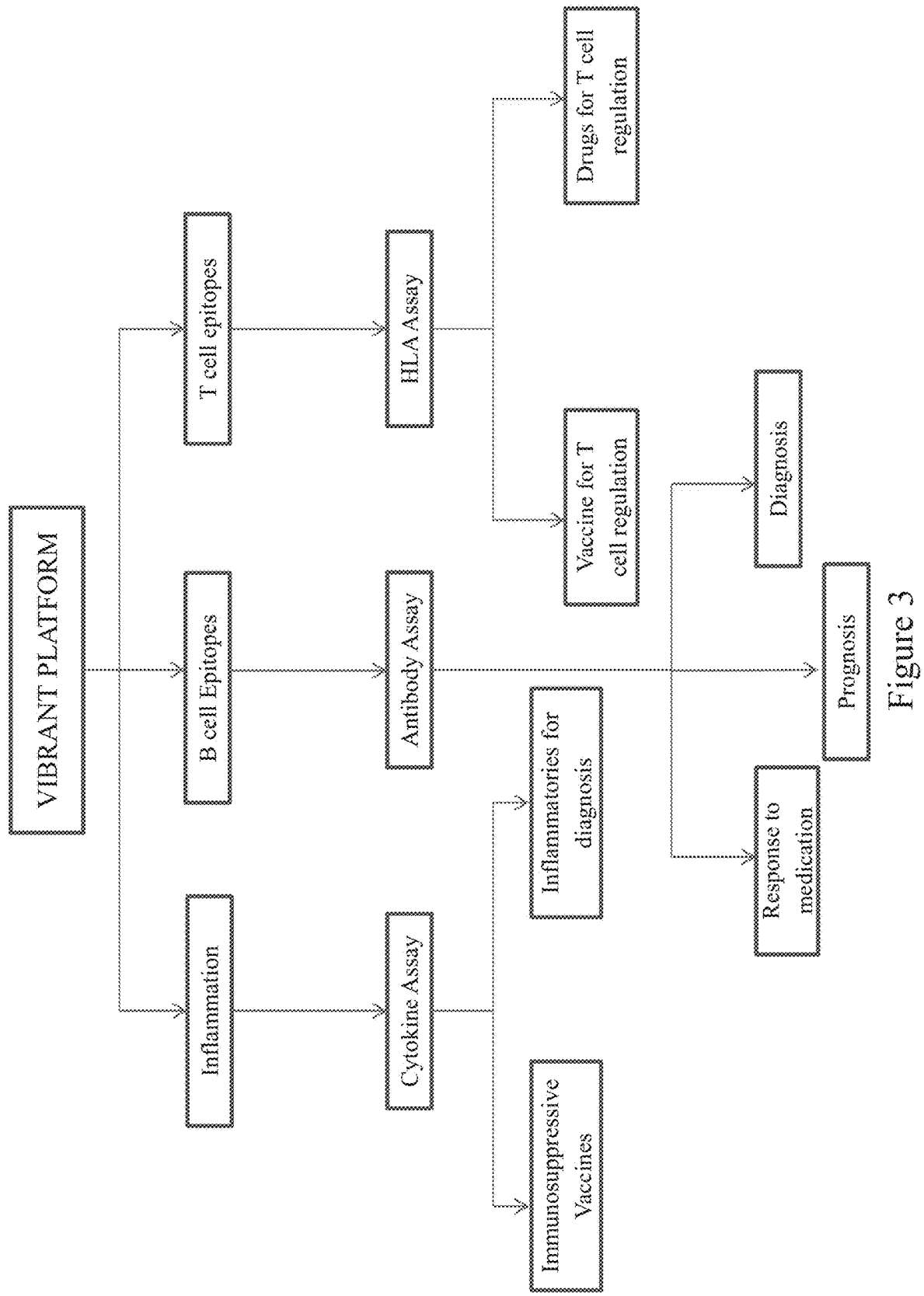
FIG. 3 diagrams the flow chart of analysis for diagnosing and treating an autoimmune disorder, according to an embodiment of the invention.

The peptide array disclosed herein may be used to identify epitopes related to autoimmune diseases. In one embodiment, the epitopes are B cell epitopes, T cell epitopes, or epitopes related to inflammatory response (e.g., TNF). Epitopes related to inflammatory response may be identified by the present invention using a cytokine assay. In one embodiment, the peptide sequences identified by this cytokine assay may be used in immunosuppressive vaccines. In other embodiments, the peptide sequences may be used as part of a peptide array to identify the presence of inflammatory molecules in a subject suspected of having an inflammatory disorder, e.g., an autoimmune disorder. In one embodiment, the peptide array may be used to identify B cell epitopes. In this embodiment, epitopes binding to antibodies from a sample associated with an autoimmune disorder are identified. These peptides are then used on another peptide array useful for diagnosis of an autoimmune disorder. In one embodiment, diagnosis of an autoimmune disorder includes identification of autoimmune disorder subtype. In some embodiments, the identified B cell epitopes are used to measure a patient's response to treatment of an autoimmune disorder. In one embodiment, T cell epitopes may be identified by the present invention using an MHC complex assay (e.g., a human leukocyte antigen assay). Epitopes identified as interacting with the MHC complex in a subject identified as having an autoimmune disorder may be used for treatment of the autoimmune disorder. Such peptides may be useful in a vaccine or other drugs for T cell regulation. A flow chart depicting the identification of epitope sequences and their use, according to several embodiments of the invention, is shown in FIG. 3.

In some aspects the invention includes bioinformatic analysis of data to, e.g., identify informative sub-sequences, and subsequent synthesis and testing of synthetic peptide sequences useful for diagnosing a condition. These bioinformatic methods are carried out, in part, using a computer to accomplish one or more of the following steps: 1) generating subsequences from longer sequences; 2) tabulating and ranking the occurrence of subsequences in positive hits from samples bound to arrays of tiled naturally-occurring peptide sequences; 3) analyzing hits to arrays comprising synthetic sequences that include informative subsequences.

Unless specifically stated otherwise as apparent from the following discussion, it is appreciated that throughout the description, discussions utilizing terms such as "processing" or "computing" or "calculating" or "determining" or "displaying" or "analyzing" or "comparing" or "identifying" or the like, refer to the action and processes of a computer system, or similar electronic computing device, that manipulates and transforms data represented as physical (electronic) quantities within the computer system's registers and memories into other data similarly represented as physical (electronic) quantities within the computer system's registers and memories into other data similarly represented as physical quantities within the computer system memories or registers or other such information storage, transmission or display devices.

The present invention also relates to system apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

Various general purpose systems may be used with programs in accordance with the teachings herein, or it may prove convenient to construct more specialized apparatus to perform the required method procedures. The required structure for a variety of these systems will appear from the description below. In addition, the present invention is not described with reference to any particular programming language. It will be appreciated that a variety of programming languages may be used to implement the teachings of the invention as described herein.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: Substrate Production

This example describes construction of a substrate. This process is visually outlined in FIG. 1. Silicon wafers with 2.4 µm thermally grown oxide were obtained from University Wafers. These wafers were first primed with a primer in a spray module. Hexamethyl disilazane (HMDS) was obtained from Sigma Aldrich Inc. The wafers were then spun coat in a photoresist coat module with a commercially available deep Ultra violet photoresist, P5107 obtained from Rohm and Haas or AZ DX7260p 700 from AZ Electronic Materials, to obtain a thickness of 6000 Å. The wafers were then baked in a hot plate at 120° C. for 60 seconds.

Photomasks that have the patterned regions to create the features were used to image the array on to the substrate surface. The wafers were then exposed in a 248 nm deep ultra violet radiation scanner tool, Nikon 5203, with expose energy of 18 mJ/cm2. The wafers were then post exposure baked at 110° C. for 120 seconds in a hot plate and developed with commercially available NMD-3 developer, obtained from Tokyo Ohka Kogyo Co., Ltd., for 60 seconds.

After this the oxide was etched by using either a wet etch process or dry plasma etch process. Standard semiconductor etch techniques were used. Oxide etch depths were from 1000 Å to 2000 Å.

After etching, chromium was deposited to a thickness of 500 Å to 1500 Å by a physical deposition method. Standard etching and metal deposition techniques were employed.

After the chromium was deposited, the resist was lifted off with the following process: The wafer was left in Nanostrip obtained from Cyantek Inc. overnight and then dipped in Piranha solution for 90 mins. Piranha solution is a 50:50 mixture of sulfuric acid and hydrogen peroxide. Sulfuric acid and hydrogen peroxide were obtained from Sigma Aldrich Corp. Plasma ashing was performed to oxidize the remaining impurities. This process produced a substrate having pillars of silicon dioxide separated by metal.

Alternatively, the deposited chromium was also polished to a depth of 500 Å to 1500 A, depending on the deposition. The polishing was performed to obtain pillars of silicon dioxide separated by metal. The separation of each pillar from center to center was 70,000 Å. The surface area of top of each pillar was 3,500 Å×3,500 Å.

Derivatization: The wafers were then surface derivatized using the following method: Aminopropyl triethoxy silane (APTES) was obtained from Sigma Aldrich. Ethanol 200 proof was obtained from VWR. The wafers were first washed with ethanol for 5 minutes and then in 1% by weight APTES/Ethanol for 20-30 minutes to grow the silane layer. Then the wafers were cured in a 110° C. nitrogen bake oven to grow a mono silane layer with a —$NH_2$ group to attach a linker molecule.

Example 2: Photoresist Formulation Production and Use

Water Soluble Photoresists were Prepared as Follows:

The water soluble compounds were obtained from Hampford Research Inc. These included a water soluble thioxanthenone derivative and a water soluble photoacid generator (PAG). Polyvinylpyrrolidone (PVP) was obtained from Polysciences Inc.

2% by weight (0.5%-5% by weight was tested and gave similar results; data not shown) of PVP was dissolved in water. Next the photoacid generator (4% by weight) and the photo initiators (4% by weight) were added at a ratio of 1:2 with respect to PVP. All of the components were then left spinning in a magnetic stirrer overnight to obtain the final composition. The inclusion of photoinitiators is optional.

Specific photoactive formulations produced using the above procedures (as a general guide) are shown in Table 1. Each formulation from Table 1 was made by selecting a single cell from each column within a particular formulation row (1-4). For instance, one formulation (from formulation row 1 from Table 1, top row) included the following components: Polyethylene glycol monomethyl ether 2 wt %; Polyvinyl pyrrollidone 2 wt %; 4 Methoxyphenyl)phenyliodonium trifluoromethanesulfonate 5 wt %; Water soluble Isopropyl thioxanthenone (ITX) 5 wt % (Lin et al., "Synthesis of Water Soluble Photoinitiators of Thioxanthone Derivatives III" Huadong Ligong Daxue Xuebao, vol. 26, No. 2, 2000, pp. 212-214, 220); and the remainder of the formulation being solvent (the solvent being 100% water). In another instance, a different formulation (from formulation row 2 from Table 1, top row) included the following components: Polyethylene glycol monomethyl ether 2 wt %; Polyvinyl pyrrollidone 2 wt %; (4 methoxyphenyl)dimethylsulfonium triflate 5 wt %; Water soluble ITX 5 wt %; and the remainder of the formulation being solvent (the solvent being 90% by weight water and 10% by weight Propylene glycol methyl ether acetate (PGMEA)).

The formulations were prepared as described above. Each photoresist formulation was then spin coated on a substrate (see above) at varying speeds to obtain the desired thickness.

TABLE 1

| | Photoactive Formulations | | | |
|---|---|---|---|---|
| Formulation | Polymer | Photoacid generators | Photo initiators | Solvent (wt %) |
| 1 | Polyethylene glycol monomethyl ether 2 wt % Polyvinyl pyrrollidone 2 wt % Poly (2-dimethylaminoethyl methacrylate) 2.5 wt % Poly (2-hydroxypropyl methacrylate) 2.5 wt % Poly 4 vinyl pyridine 5 wt % | 4 Methoxyphenyl)phenyliodonium trifluoromethanesulfonate 5 wt % | Water soluble ITX 5 wt % | Water 100% |
| 2 | Polyethylene glycol monomethyl ether 2 wt % Polyvinyl pyrrollidone 2 wt % Poly (2-dimethylaminoethyl methacrylate) 2.5 wt % Poly (2-hydroxypropyl methacrylate) 2.5 wt % Poly 4 vinyl pyridine 5 wt % | (4 methoxyphenyl)dimethylsulfonium triflate 5 wt % | Water soluble ITX 5 wt % | Water 90% PGMEA 10% |

TABLE 1-continued

Photoactive Formulations

| Formulation | Polymer | Photoacid generators | Photo initiators | Solvent (wt %) |
|---|---|---|---|---|
| 3 | Polyethylene glycol monomethyl ether 2 wt % Polyvinyl pyrrollidone 2 wt % Poly (2-dimethylaminoethyl methacrylate) 2.5 wt % Poly (2-hydroxypropyl methacrylate) 2.5 wt % Poly 4 vinyl pyridine 5 wt % | (2,4-dihydroxyphenyl)dimethylsulfonium triflate 2.5 wt % (4 methoxyphenyl)dimethylsulfonium triflate 2.5 wt % | Water soluble ITX 5 wt % | Water 90% ethyl lactate 10% |
| 4 | Polyethylene glycol monomethyl ether 2 wt % Polyvinyl pyrrollidone 2 wt % Poly (2-dimethylaminoethyl methacrylate) 2.5 wt % Poly (2-hydroxypropyl methacrylate) 2.5 wt % Poly 4 vinyl pyridine 5 wt % | (2,4-dihydroxyphenyl)dimethylsulfonium triflate 2.5 wt % (4 methoxyphenyl)dimethylsulfonium triflate 2.5 wt % | Water soluble ITX 5 wt % | Water 50% ethyl lactate 50% |

Note:
The % in the solvent column refers to the contents of the solvent itself. E.g., 100% water means that the solvent is 100% water.

Example 3: Coupling Formulation and Capping Solution Production and Use

Water-Based Coupling Solutions for the 20 Natural Amino Acids were Prepared as Follows:

Water soluble inert polymers such as poly vinyl alcohol (PVA), polyvinyl pyrrolidone (PVP), or polyethyleneglycol were obtained from Polysciences Inc.

EDC (1-ethyl-3-(3-dimethylaminopropyl) carbodiimide), and HonB (n-hydroxy-5-norbornene-2,3-dicarboximide) were obtained from Sigma Aldrich Corp. DIEA (Diisopropylethylamine) was obtained from Sigma Aldrich Corp.

All t-boc/Fmoc protected amino acids were obtained from AAPPTEC/Anaspec. The inert water soluble polymers 3% by weight PVP and 7% by weight PVA were dissolved in the ratio of 1:2.5 in deionized (DI) water which makes up about 10% by weight of the solution along with 2% by weight amino acid concentration. 4% by weight for each EDC and HonB were added as reagents twice the concentration of amino acids. DIEA (4% by weight) was added at the same concentration as EDC and HoNb. This water coupling solution was spin coated on a derivatized substrate to form a uniform solid layer all available to couple to the substrate. The wafer was then baked on a hot plate for 2 minutes at 90° C. to remove the remaining solvent (DI water) and coupled at the same time. Next the coupling coat was washed away with DI water in a strip module.

Specific coupling formulations produced using the above procedures (as a general guide) are shown in Table 2. Each formulation from Table 2 was made by selecting a single cell from each column within a particular formulation row (1-20). For instance, one formulation (from formulation row 1 from Table 2, top row) included the following components: Polyvinyl alcohol: 10% by weight; Boc-Ala-OH, Boc-Ala-NH$_2$, Boc-Ala-Osu (Osu=Oxy succinimide) (Concentration—0.2M and 0.3M); 1-ethyl-3-(3-dimethylaminopropyl) carbodiimide (Concentration-0.3M); 50% N-methylpyrrolidone+50% Diisopropylethylamine (total concentration 0.3M); and the remainder of the formulation being solvent (the solvent being 100% water). In another instance, a different formulation (from formulation row 2 from Table 2, top row) included the following components: Polyvinyl alcohol-10% by weight; Boc-Arg-OH, Boc-Arg-(Mts)-OH (Mts=Mesitylene sulfonyl), Boc-Arg(Z)—OH (Concentration—0.2M and 0.3M); 1-ethyl-3-(3-dimethylaminopropyl) carbodiimide (Concentration-0.3M); 50% N-methylpyrrolidone+50% Diisopropylethylamine (total concentration 0.3M); and the remainder of the formulation being solvent (the solvent being 100% water). Formulations for each of the 20 standard amino acids are shown in Table 2. Each coupling formulation comprises at least one polymer, amino acid, coupling reagent, neutralizing agent, and solvent selected from the respective columns for each formulation in Table 2.

The formulations were prepared as described above.

Capping Solution was Prepared as Follows:

Acetic anhydride was obtained from Sigma Aldrich Corp. PVP was dissolved in N-methylpyrrolidone which makes up 2% by weight (1-2% by weight was tested and gave similar results; data not shown) of the total solution. Next acetic anhydride was added to make up 25% by weight (20-30% by weight was tested and gave similar results; data not shown) of the solution. This capping solution was then spin coated on the wafers in a capping module by spinning the wafers at 2000 rpm for 30 seconds. The wafers were then baked in a cap bake module for up to 2 minutes at 75° C. to complete the capping process. The remaining solution was washed away with DI water in a strip module.

The above processes are visually outlined in FIG. 2.

TABLE 2

Coupling Formulations

| Formulation | Polymer | Amino acid | Coupling reagent | Neutralizing agent | Solvent (wt %) |
|---|---|---|---|---|---|
| 1 | Polyvinyl alcohol- 10 wt % Polyvinyl pyrrolidone-10 wt % | Boc- Ala-OH, Boc-Ala-NH2, Boc- Als-Osu Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrolidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrolidone |
| | Poly ethylene glycol 5 wt % Poly 2 vinyl pyridine N oxide 5 wt % Poly ethylene glycol monomethyl ether 10 wt % | | | | 80% water 20% N Methyl pyrrolidone 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 2 | Polyvinyl alcohol- 10 wt % Polyvinyl pyrrolidone-10 wt % | Boc- Arg-OH, Boc-Arg (Mts)-OH, Boc- Arg(Z)-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrolidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrolidone |
| | Poly ethylene glycol 5 wt % Poly 2 vinyl pyridine N oxide 5 wt % Poly ethylene glycol monomethyl ether 10 wt % | | | | 80% water 20% N Methyl pyrrolidone 10% dimethyl formamide |
| | Polyethylene glycol monomethylether 5 wt % Poly vinyl alcohol 2.5 wt % Poly vinyl pyrrolidone 2.5 wt % Polyethylene glycol dimethyl ether 5 wt % Poly vinyl alcohol 2.5 wt % Poly vinyl pyrrolidone 2.5 wt % | | | | 80% water 20% N Methyl pyrrolidone |
| 3 | Polyvinyl alcohol- 10 wt % Polyvinyl pyrrolidone-10 wt % | Boc- Asn-OH, Boc-Asn(trt)-OH, Boc-Asn(Xan)-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrolidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrolidone |
| | Poly ethylene glycol 5 wt % Poly 2 vinyl pyridine N oxide 5 wt % Poly ethylene glycol monomethyl ether 10 wt % | | | | 80% water 20% N Methyl pyrrolidone 10% dimethyl formamide |

TABLE 2-continued

| | Coupling Formulations | | | | |
|---|---|---|---|---|---|
| Formulation | Polymer | Amino acid | Coupling reagent | Neutralizing agent | Solvent (wt %) |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 4 | Polyvinyl alcohol-10 wt % Polyvinyl pyrrolidone-10 wt % | Boc-Asp(Obzl)-OH, Boc-Asp(Otbu)-OH, Boc-Asp-Otbu Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrollidone |
| | Poly ethylene glycol 5 wt % Poly 2 vinyl pyridine N oxide 5 wt % Poly ethylene glycol monomethyl ether 10 wt % | | | | 80% water 20% N Methyl pyrrollidone 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 5 | Polyvinyl alcohol-10 wt % Polyvinyl pyrrolidone-10 wt % | Boc-Cys(Acm)-OH, Boc-Cys(Bzl)-OH, Boc-Cys(Acm)-Onp Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 20% N Methyl pyrrollidone |
| | Poly ethylene glycol 5 wt % Poly 2 vinyl pyridine N oxide 5 wt % Poly ethylene glycol monomethyl ether 10 wt % | | | | 80% water 20% N Methyl pyrrollidone 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |

TABLE 2-continued

Coupling Formulations

| Formulation | Polymer | Amino acid | Coupling reagent | Neutralizing agent | Solvent (wt %) |
|---|---|---|---|---|---|
| 6 | Polyvinyl alcohol-10 wt % Polyvinyl pyrrolidone-10 wt % | Boc- Gln-OH, Boc-Gln(Trt)-OH, Boc-Gln(Xan)-OH, Boc-Gln-Onp Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water |
|  |  |  |  |  | 50% water 50% N Methyl pyrrolidone |
|  | Polyvinyl alcohol 2.5 wt % Polyvinyl pyrrolidone 2.5 wt % |  | n hydroxy 5 norbornene 2,3 di carboximide Concentration-0.2M |  | 90% water 10% N Methyl pyrrolidone |
|  | Poly ethylene glycol 5 wt % Poly 2 vinyl pyridine N oxide 5 wt % Poly ethylene glycol monomethyl ether 10 wt % |  |  |  | 80% water 20% N Methyl pyrrolidone 10% dimethyl formamide |
|  | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % |  |  |  | 80% water 20% N Methyl pyrrollidone |
| 7 | Polyvinyl alcohol-10 wt % Polyvinyl pyrrolidone-10 wt % | Boc- Glu-OH, Boc-Glu-NH2, Boc- Glu-Otbu, Boc-Glu(Otbu)-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water |
|  |  |  |  |  | 50% water 50% N Methyl pyrrolidone |
|  | Polyvinyl alcohol 2.5 wt % Polyvinyl pyrrolidone 2.5 wt % |  | n hydroxy 5 norbornene 2,3 di carboximide Concentration-0.2M |  | 90% water 10% N Methyl pyrrolidone |
|  | Poly ethylene glycol 5 wt % Poly 2 vinyl pyridine N oxide 5 wt % Poly ethylene glycol monomethyl ether 10 wt % |  |  |  | 80% water 20% N Methyl pyrrolidone 10% dimethyl formamide |
|  | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % |  |  |  | 80% water 20% N Methyl pyrrolidone |
| 8 | Polyvinyl alcohol-10 wt % Polyvinyl pyrrolidone-10 wt % | Boc- Gly-OH, Boc-Gly-N(Ome)Me, Boc- Gly-Osu Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water |
|  |  |  |  |  | 50% water 50% N Methyl pyrrolidone |
|  | Polyvinyl alcohol 2.5 wt % Polyvinyl pyrrolidone 2.5 wt % |  | n hydroxy 5 norbornene 2,3 di carboximide Concentration-0.2M |  | 90% water 10% N Methyl pyrrolidone |
|  | Poly ethylene glycol 5 wt % Poly 2 vinyl pyridine N oxide 5 wt % Poly ethylene glycol monomethyl ether 10 wt % |  |  |  | 80% water 20% N Methyl pyrrolidone 10% dimethyl formamide |

TABLE 2-continued

| | | Coupling Formulations | | | |
|---|---|---|---|---|---|
| Formulation | Polymer | Amino acid | Coupling reagent | Neutralizing agent | Solvent (wt %) |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 9 | Polyvinyl alcohol- 10 wt % Polyvinyl pyrrolidone-10 wt % | Boc- His-OH, Boc-His-Bom-OH, Boc-His(Tos)-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrollidone |
| | Poly ethylene glycol 5 wt % Poly 2 vinyl pyridine N oxide 5 wt % Poly ethylene glycol monomethyl ether 10 wt % | | | | 80% water 20% N Methyl pyrrollidone 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 10 | Polyvinyl alcohol- 10 wt % Polyvinyl pyrrolidone-10 wt % | Boc- Ile-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrollidone |
| | Poly ethylene glycol 5 wt % Poly 2 vinyl pyridine N oxide 5 wt % Poly ethylene glycol monomethyl ether 10 wt % | | | | 80% water 20% N Methyl pyrrollidone 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |

TABLE 2-continued

Coupling Formulations

| Formulation | Polymer | Amino acid | Coupling reagent | Neutralizing agent | Solvent (wt %) |
|---|---|---|---|---|---|
| 11 | Polyvinyl alcohol-10 wt % Polyvinyl pyrrolidone-10 wt % | Boc- Leu-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
|  | Polyvinyl alcohol 2.5 wt % Polyvinyl pyrrolidone 2.5 wt % |  | n hydroxy 5 norbornene 2,3 di carboximide Concentration-0.2M |  | 90% water 10% N Methyl pyrrolidone |
|  | Poly ethylene glycol 5 wt % Poly 2 vinyl pyridine N oxide 5 wt % Poly ethylene glycol monomethyl ether 10 wt % |  |  |  | 80% water 20% N Methyl pyrrolidone 10% dimethyl formamide |
|  | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % |  |  |  | 80% water 20% N Methyl pyrrollidone |
| 12 | Polyvinyl alcohol-10 wt % Polyvinyl pyrrolidone-10 wt % | Boc- Lys-OH, Boc-Lys(Z)-OH, Boc- Lys-Osu Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrolidone |
|  | Polyvinyl alcohol 2.5 wt % Polyvinyl pyrrolidone 2.5 wt % |  | n hydroxy 5 norbornene 2,3 di carboximide Concentration-0.2M |  | 90% water 10% N Methyl pyrrolidone |
|  | Poly ethylene glycol 5 wt % Poly 2 vinyl pyridine N oxide 5 wt % Poly ethylene glycol monomethyl ether 10 wt % |  |  |  | 80% water 20% N Methyl pyrrolidone 10% dimethyl formamide |
|  | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % |  |  |  | 80% water 20% N Methyl pyrrollidone |
| 13 | Polyvinyl alcohol-10 wt % Polyvinyl pyrrolidone-10 wt % | Boc- Met-OH, Boc-Met(O)-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrolidone |
|  | Polyvinyl alcohol 2.5 wt % Polyvinyl pyrrolidone 2.5 wt % |  | n hydroxy 5 norbornene 2,3 di carboximide Concentration-0.2M |  | 90% water 10% N Methyl pyrrolidone |
|  | Poly ethylene glycol 5 wt % Poly 2 vinyl pyridine N oxide 5 wt % Poly ethylene glycol monomethyl ether 10 wt % |  |  |  | 80% water 20% N Methyl pyrrolidone 10% dimethyl formamide |

TABLE 2-continued

| | | Coupling Formulations | | | |
|---|---|---|---|---|---|
| Formulation | Polymer | Amino acid | Coupling reagent | Neutralizing agent | Solvent (wt %) |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 14 | Polyvinyl alcohol- 10 wt % Polyvinyl pyrrolidone-10 wt % | Boc- Phe-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrollidone |
| | Poly ethylene glycol 5 wt % Poly 2 vinyl pyridine N oxide 5 wt % | | | | 80% water 20% N Methyl pyrrollidone |
| | Poly ethylene glycol monomethyl ether 10 wt % | | | | 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 15 | Polyvinyl alcohol- 10 wt % Polyvinyl pyrrolidone-10 wt % | Boc- Pro-OH, Boc-Pro-Ome Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrollidone |
| | Poly ethylene glycol 5 wt % Poly 2 vinyl pyridine N oxide 5 wt % | | | | 80% water 20% N Methyl pyrrollidone |
| | Poly ethylene glycol monomethyl ether 10 wt % | | | | 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |

TABLE 2-continued

Coupling Formulations

| Formulation | Polymer | Amino acid | Coupling reagent | Neutralizing agent | Solvent (wt %) |
|---|---|---|---|---|---|
| 16 | Polyvinyl alcohol-10 wt % Polyvinyl pyrrolidone-10 wt % | Boc- Ser-OH, Boc-Ser-OMe, Boc- Ser-Obzl, Boc-Ser(tbu)-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water |
| | Polyvinyl alcohol 2.5 wt % Polyvinyl pyrrolidone 2.5 wt % | | n hydroxy 5 norbornene 2,3 di carboximide Concentration-0.2M | | 50% water 50% N Methyl pyrrollidone |
| | Poly ethylene glycol 5 wt % Poly 2 vinyl pyridine N oxide 5 wt % Poly ethylene glycol monomethyl ether 10 wt % | | | | 90% water 10% N Methyl pyrrollidone |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone 10% dimethyl formamide 80% water 20% N Methyl pyrrollidone |
| 17 | Polyvinyl alcohol-10 wt % Polyvinyl pyrrolidone-10 wt % | Boc- Thr-OH, Boc-Thr-OMe, Boc- Thr-Osu Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrollidone |
| | Poly ethylene glycol 5 wt % Poly 2 vinyl pyridine N oxide 5 wt % Poly ethylene glycol monomethyl ether 10 wt % | | | | 80% water 20% N Methyl pyrrollidone 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 18 | Polyvinyl alcohol-10 wt % Polyvinyl pyrrolidone-10 wt % | Boc- Trp-OH, Boc-Trp(For)-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrollidone |
| | Poly ethylene glycol 5 wt % Poly 2 vinyl pyridine N oxide 5 wt % Poly ethylene glycol monomethyl ether 10 wt % | | | | 80% water 20% N Methyl pyrrollidone 10% dimethyl formamide |

TABLE 2-continued

| | | Coupling Formulations | | | |
|---|---|---|---|---|---|
| Formulation | Polymer | Amino acid | Coupling reagent | Neutralizing agent | Solvent (wt %) |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 19 | Polyvinyl alcohol-10 wt % Polyvinyl pyrrolidone-10 wt % | Boc- Tyr-OH, Boc-Tyr(Me)-OH, Boc- Tyr-Otbu, Boc-Tyr(Bzl)-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrollidone |
| | Poly ethylene glycol 5 wt % Poly 2 vinyl pyridine N oxide 5 wt % Poly ethylene glycol monomethyl ether 10 wt % | | | | 80% water 20% N Methyl pyrrollidone 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |
| 20 | Polyvinyl alcohol-10 wt % Polyvinyl pyrrolidone-10 wt % | Boc- Val-OH Concentration- 0.2M and 0.3M | 1-ethyl-3-(3-dimethylaminopropyl) carbodiimide) Concentration-0.3M | 50 wt % N methyl Pyrrolidone + 50 wt % Di isopropyl ethyl amine Total concentration 0.3M | 100% Water 50% water 50% N Methyl pyrrollidone |
| | Polyvinyl alcohol 2.5 wt % Polyvinyl pyrrolidone 2.5 wt % | | n hydroxy 5 norbornene 2,3 di carboximide Concentration-0.2M | | 90% water 10% N Methyl pyrrollidone |
| | Poly ethylene glycol 5 wt % Poly 2 vinyl pyridine N oxide 5 wt % Poly ethylene glycol monomethyl ether 10 wt % | | | | 80% water 20% N Methyl pyrrollidone 10% dimethyl formamide |
| | Polyethylene glycol monomethylether 5 wt % Poly vinyl alcohol 2.5 wt % Poly vinyl pyrrolidone 2.5 wt % Polyethylene glycol dimethylether 5 wt % Poly vinyl alcohol 2.5 wt % Poly vinyl pyrrolidone 2.5 wt % | | | | 80% water 20% N Methyl pyrrollidone |

Note:
The % in the solvent column refers to the contents of the solvent itself. E.g., 100% water means that the solvent is 100% water.

Example 4: Yield Data for 20-Mer Homopolymeric Peptides

The materials and methods used in this example are as described above in Examples 1-3. Specifically, amino acids Ala, Asp and His were prepared as follows. The inert water soluble polymers (3% by weight PVP and 7% by weight PVA) were dissolved in the ratio of 1:2.5 in deionized (DI) water which makes up about 10% by weight of the solution along with 2% by weight amino acid concentration. 4% by weight for each EDC and HonB were added as reagents twice the concentration of amino acids. DIEA (4% by weight) was added at the same concentration as EDC and HoNb. This water coupling solution was spin coated on a derivatized substrate to form a uniform solid layer, all available to couple to the substrate. The wafer was then baked on a hot plate for 2 minutes at 90° C. to remove the remaining solvent (DI water) and coupled at the same time. Next the coupling coat was washed away with DI water in a strip module.

Capping Solution was Prepared as Follows:

Acetic anhydride was obtained from Sigma Aldrich Corp. PVP was dissolved in N methyl pyrrolidone which makes up 2% by weight (1-2% by weight was tested and gave similar results; data not shown) of the total solution. Next acetic anhydride was added to make up 25% by weight (20-30% by weight was tested and gave similar results; data not shown) of the solution. This capping solution was then spin coated on the wafers in a capping module by spinning the wafers at 2000 rpm for 30 sec. The wafers were then baked in a cap bake module for up to 2 minutes at 75° C. to complete the capping process. The remaining solution was washed away with DI water in a strip module.

The same steps were followed for synthesizing 20-mer peptides with the following sequences:

1.
(SEQ ID NO: 2)
Ala-Ala-Ala-Ala-Ala-Ala-Ala-Ala-Ala-Ala-Ala-Ala-Ala-Ala-Ala-Ala-Ala-Ala-Ala-Ala, 2.
(SEQ ID NO: 3)
Asp-Asp-Asp-Asp-Asp-Asp-Asp-Asp-Asp-Asp-Asp-Asp-Asp-Asp-Asp-Asp-Asp-Asp-Asp-Asp, 3.
(SEQ ID NO: 4)
His-His-His-His-His-His-His-His-His-His-His-His-His-His-His-His-His-His-His-His.

This example shows the step yield data for each of the above 20-mer amino acid sequences. To measure step yield via fluorescence, a fluorescent dye molecule was coupled to the sequence of amino acids in order to determine the coupling efficiency. The amount of fluorescein dye coupled gives a direct measure of the amount of sequence grown.

The formula used to calculate step yield was: Step yield = $(F_n/F_1)^{1/n-1}$, where $F_1$ and $F_n$ denotes the fluorescein coupling intensity read out from a fluorescent scanner device at the first step and the nth step. The coupling yield was calculated using the formula $E = 10 \char`\^ ((\log F)/C)$ where F equals fraction of full length and C = number of couplings = length−1.

Figure 4A:
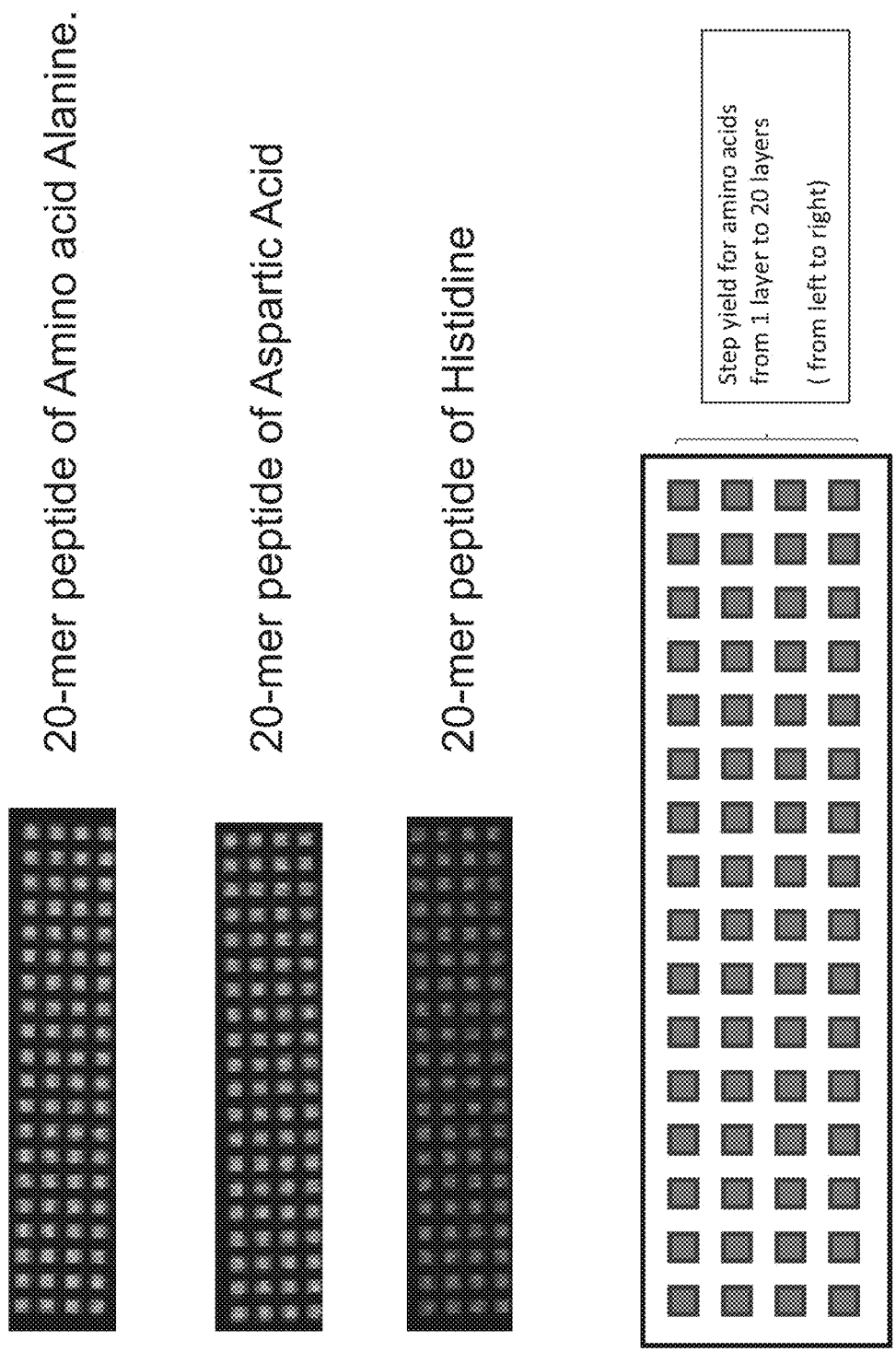
FIG. 4A shows the readout of the fluorescence signal from each of the 20-mer experiments.
Figure 4B:
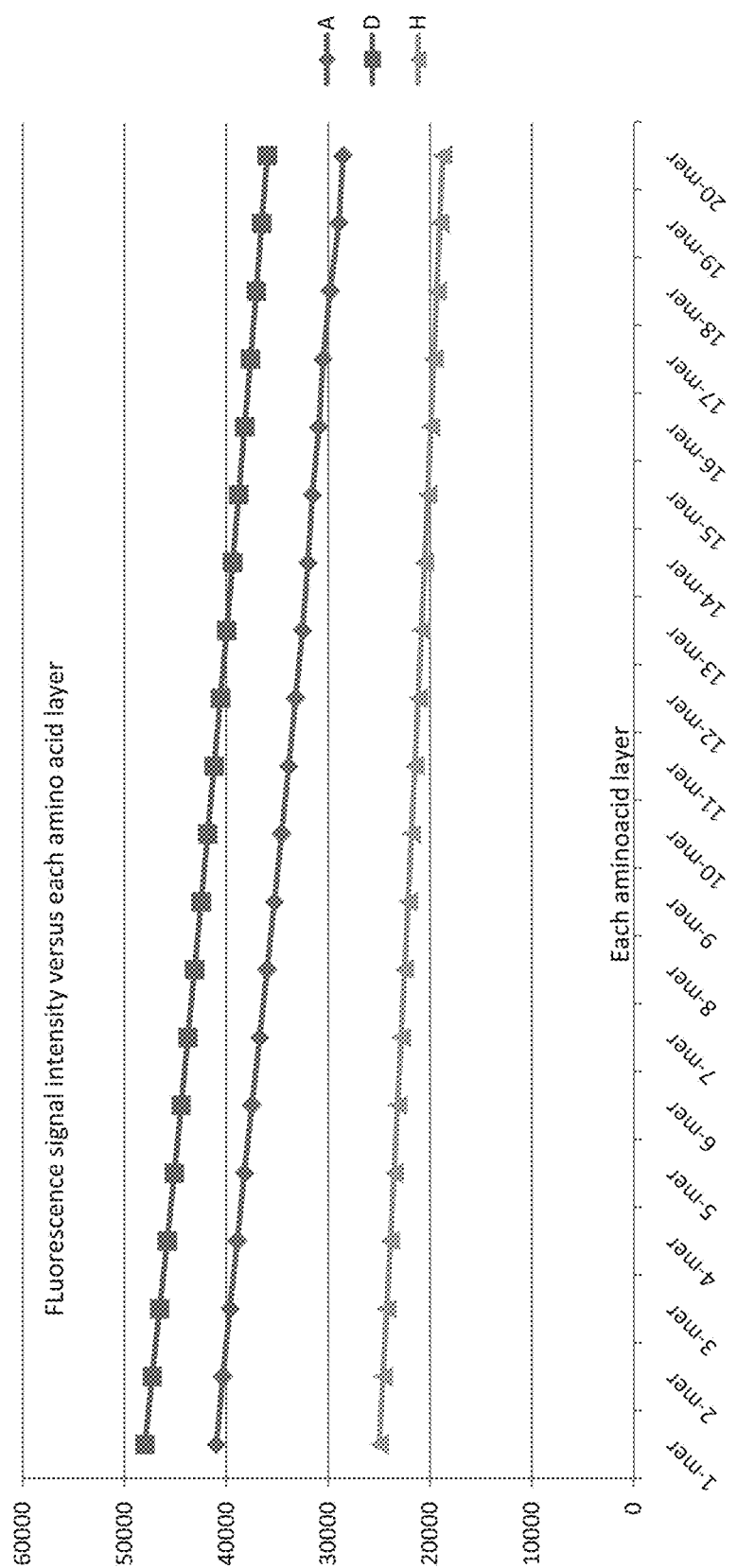
FIG. 4B shows fluorescence signal intensity vs. each amino acid layer.
Figure 5:
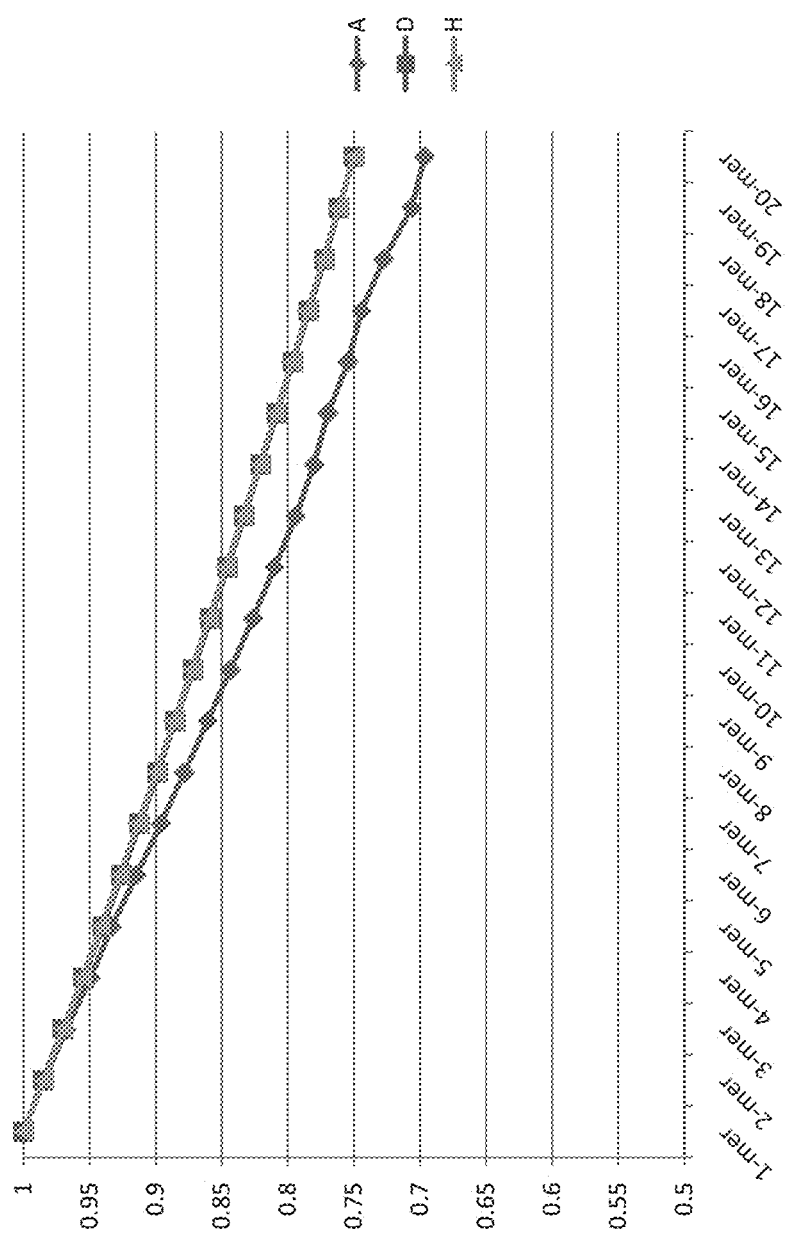
FIG. 5 shows the overall step yield analysis via a graph of step yield vs. each amino acid layer.

Table 3 shows the fluorescence signal intensity at each layer. FIG. 4A shows the readout of the fluorescence signal from each of the 20-mer experiments. FIG. 4B shows a graph of fluorescence signal intensity vs. each amino acid layer. FIG. 5 shows a graph of overall step yield vs. each amino acid layer. Table 4 shows the yield efficiency for each coupling step. The coupling efficiency of each amino acid was calculated to be greater than 98% in each instance across the entire length of each of the 20-mer peptides.

TABLE 3

Fluorescence signal intensity at each layer for PolyA, PolyD, and PolyH

| Amino Acid | 1-mer | 2-mer | 3-mer | 4-mer | 5-mer | 6-mer | 7-mer | 8mer | 9-mer | 10-mer |
|---|---|---|---|---|---|---|---|---|---|---|
| A | 41000 | 40363.4 | 39679 | 38924 | 38261 | 37496.8 | 36745.9 | 36012.2 | 35291.1 | 34583.6 |
| D | 48000 | 47298.1 | 46577.6 | 45823.1 | 45123.5 | 44445.8 | 43787.9 | 43132.2 | 42484.7 | 41846.3 |
| H | 25006.5 | 24623.4 | 24253.4 | 23899.7 | 23541.2 | 23187.6 | 22839.9 | 22496.4 | 22158.7 | 21825.4 |

| | 11-mer | 12-mer | 13-mer | 14-mer | 15-mer | 16-mer | 17-mer | 18-mer | 19-mer | 20-mer |
|---|---|---|---|---|---|---|---|---|---|---|
| A | 33891.2 | 33212.3 | 32547.5 | 31995.6 | 31556.7 | 30930.9 | 30517.9 | 29823.6 | 28965.4 | 28554.4 |
| D | 41213.4 | 40594.5 | 39986.7 | 39386.3 | 38798.2 | 38215.4 | 37642.1 | 37067.6 | 36542.3 | 35995.6 |
| H | 21497.8 | 21175.4 | 20857.6 | 20544.3 | 20234.5 | 19932.2 | 19632.2 | 19338.1 | 19047.9 | 18762.3 |

TABLE 4

Yield efficiency at each layer for PolyA, PolyD, and PolyH

| | 1-mer | 2-mer | 3-mer | 4-mer | 5-mer | 6-mer | 7-mer | 8-mer | 9-mer | 10-mer |
|---|---|---|---|---|---|---|---|---|---|---|
| Couplings | | 1 | 2 | 3 | 4 | 5 | 6 | 7 | 8 | 9 |
| A amino acid | 1 | 0.984 | 0.968 | 0.949 | 0.933 | 0.915 | 0.896 | 0.878 | 0.861 | 0.844 |
| Coupling Efficiency | | 0.984 | 0.984 | 0.983 | 0.983 | 0.982 | 0.982 | 0.982 | 0.981 | 0.981 |
| D amino acid | 1 | 0.985 | 0.970 | 0.955 | 0.940 | 0.926 | 0.912 | 0.899 | 0.885 | 0.872 |
| Coupling Efficiency | | 0.985 | 0.985 | 0.985 | 0.985 | 0.985 | 0.985 | 0.985 | 0.985 | 0.985 |

TABLE 4-continued

Yield efficiency at each layer for PolyA, PolyD, and PolyH

| H amino acid | 1 | 0.985 | 0.970 | 0.956 | 0.941 | 0.927 | 0.913 | 0.900 | 0.886 | 0.873 |
|---|---|---|---|---|---|---|---|---|---|---|
| Coupling Efficiency | | 0.985 | 0.985 | 0.9855 | 0.9855 | 0.9855 | 0.9855 | 0.9855 | 0.985 | 0.985 |

| | 11-mer | 12-mer | 13-mer | 14-mer | 15-mer | 16-mer | 17-mer | 18-mer | 19-mer | 20-mer |
|---|---|---|---|---|---|---|---|---|---|---|
| Couplings | 10 | 11 | 12 | 13 | 14 | 15 | 16 | 17 | 18 | 19 |
| A amino acid | 0.827 | 0.81 | 0.794 | 0.780 | 0.770 | 0.754 | 0.744 | 0.727 | 0.706 | 0.696 |
| Coupling Efficiency | 0.981 | 0.981 | 0.981 | 0.981 | 0.981 | 0.981 | 0.982 | 0.981 | 0.981 | 0.981 |
| D amino acid | 0.859 | 0.846 | 0.833 | 0.821 | 0.808 | 0.796 | 0.784 | 0.772 | 0.761 | 0.750 |
| Coupling Efficiency | 0.985 | 0.985 | 0.985 | 0.985 | 0.985 | 0.985 | 0.985 | 0.985 | 0.985 | 0.985 |
| H amino acid | 0.860 | 0.847 | 0.834 | 0.822 | 0.809 | 0.797 | 0.785 | 0.773 | 0.762 | 0.750 |
| Coupling Efficiency | 0.985 | 0.985 | 0.985 | 0.985 | 0.985 | 0.985 | 0.985 | 0.985 | 0.985 | 0.985 |

Example 5: Yield Data for Synthesis of 1 to 12-Mer Peptides

Materials and Methods:

Water soluble inert polymers (such as poly vinyl alcohol (PVA), polyvinyl pyrrolidone (PVP), or poly ethylene glycol) were obtained from Polysciences Inc. EDC (1-ethyl-3-(3-dimethylaminopropyl) carbodiimide), and HonB (n-hydroxy-5-norbornene-2,3-di carboximide) were obtained from Sigma Aldrich Corp. DIEA (Diisopropylethylamine) was obtained from Sigma Aldrich Corp. All t-boc/Fmoc protected amino acids were obtained from AAPPTEC/Anaspec.

The inert water soluble polymers (3% by weight PVP and 7% by weight PVA) were dissolved in the ratio of 1:2.5 in deionized (DI) water which makes up about 10% by weight of the solution along with 2% by weight amino acid concentration. Amino acids used in this example were Boc-Lys-OH, Boc-Leu-OH, Boc-Met-OH, Boc-Thr-OH, Boc-Ser-OH, Boc-Asp-OH, Boc-Gly-OH, Boc-Ile-OH, Boc-Ala-OH, Boc-Arg-OH, Boc-Val-OH.

4% by weight of each EDC and HonB were added as reagents twice the concentration of amino acids. 4% by weight DIEA was added at the same concentration as EDC and HoNb.

Capping Solution was Prepared as Follows:

Acetic anhydride was obtained from Sigma Aldrich Corp. PVP was dissolved in N-methylpyrrolidone which makes up 2% by weight (1-2% by weight were also tested, data not shown) of the total solution. Next acetic anhydride was added to make up 25% by weight (20-30% by weight were also tested, data not shown) of the solution.

Fluorescein Coupling Solution is Prepared as Follows:

5,6 FAM Carboxyfluorescein was obtained from Anaspec. 0.1M Boc-Gly-OH (from AAPPTeC), 0.05M 5,6 FAM and 0.1M HoNb (Sigma Aldrich) and 0.1M EDC (Sigma Aldrich) was dissolved in water along with 5% by weight Polyvinylpyrrollidone (PolySciences).

The derivatized wafer (see Example 1) was coated with the above resist at 2000 rpm and baked at 85° C. for 90 secs. The wafer was exposed in a Nikon S-203 scanner and then post baked at 75° C. for 120 secs. The resist was stripped with deionized water. The first coupling solution with amino acid Boc-Lys-OH was spin coated on a derivatized substrate to form a solid layer, all available to couple to the substrate. The wafer was then baked on a hot plate for 2 minutes at 90° C. to remove the remaining solvent (DI water) and coupled at the same time. Next the coupling coat was washed away with DI water in a strip module.

This capping solution was then spin coated on the wafers in a capping module by spinning the wafers at 2000 rpm for 30 seconds. The wafers were then baked in a cap bake module for up to 2 minutes at 75° C. to complete the capping process. The remaining solution was washed away with DI water in a strip module.

The same procedure was followed for the other amino acids in the sequence Lys-Leu-Glu-Arg-Ser-Thr-Val-Met-Ile-Lys-Gly-Asp (SEQ ID NO: 5).

All peptide lengths between 1 and 12 were synthesized for the above peptide. After the desired peptide sequence was synthesized, the fluorescein coupling solution was spin coated on the wafer at 2,000 rpm to form a coupling dye coat. Then the wafers were baked at 65° C. for 2 mins and then the dye solution was washed away with water. This completed the coupling of fluorescein dye to allow measurement of the signals. The signal was then read off a fluorescence microscope.

Figure 6:
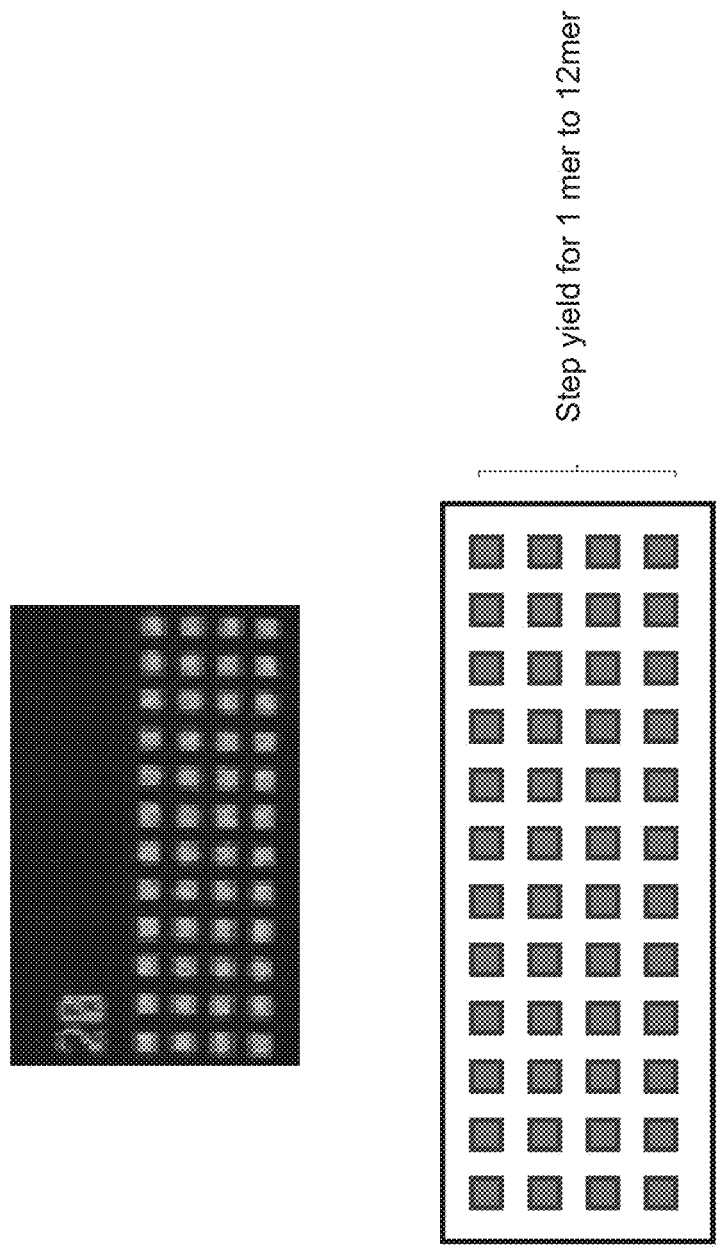
FIG. 6 shows the readout of the fluorescence signal from the 1-12-mer experiment.

Results:

The image in FIG. 6 shows the readout of the fluorescence signal from the 1 to 12-mer experiment and has 4 rows and 12 columns. Each of the 4 rows represent the same sequence. The columns contain the sequence synthesized such that one amino acid is added in each column. From left to right, each column thus represents the following sequences:

1.
Lys,

2.
Lys-Leu,

3.
Lys-Leu-Glu, 4. (SEQ ID NO: 6)
Lys-Leu-Glu-Arg, 5. (SEQ ID NO: 7)
Lys-Leu-Glu-Arg-Ser,

-continued

6.
Lys-Leu-Glu-Arg-Ser-Thr, (SEQ ID NO: 8)

7.
Lys-Leu-Glu-Arg-Ser-Thr-Val, (SEQ ID NO: 9)

The coupling yield was calculated using the formula $E = 10^{\wedge}((\log F)/C)$ where F equals fraction of full length and C=number of couplings=length−1. The formula used to calculate step yield was: Step yield=$(F_n/F_1)^{1/n-1}$, where $F_1$ and $F_n$ denotes the fluorescein coupling intensity read out from a fluorescent scanner device at the first step and the nth step.

Table 5 shows the fluorescence signal intensity, the yield efficiency for each coupling step, and the overall yield.

TABLE 5

|  | 1 mer | 2 mer | 3 mer | 4 mer | 5 mer | 6 mer |
| --- | --- | --- | --- | --- | --- | --- |
| Peptide Sequence | K | KL | KLE | KLER (SEQ ID NO: 6) | KLERS (SEQ ID NO: 7) | KLERST (SEQ ID NO: 8) |
| Fluorescence signal intensity | 54000 | 53298 | 52461.2 | 51522.1 | 50654 | 50032 |
| Yield for each coupling | 1 | 0.987 | 0.986 | 0.984 | 0.984 | 0.985 |
| Overall yield | 1 | 0.987 | 0.972 | 0.954 | 0.938 | 0.927 |
|  | 7 mer | 8 mer | 9 mer | 10 mer | 11 mer | 12 mer |
| Peptide Sequence | KLERSTV (SEQ ID NO: 9) | KLERSTVM (SEQ ID NO: 10) | KLERSTVMI (SEQ ID NO: 11) | KLERSTVMIK (SEQ ID NO: 12) | KLERSTVMIKG (SEQ ID NO: 13) | KLERSTVMIKGD (SEQ ID NO: 5) |
| Fluorescence signal intensity | 49234 | 48339 | 47456 | 46999 | 46097 | 45223.3 |
| Yield for each coupling | 0.985 | 0.9845 | 0.984 | 0.985 | 0.984 | 0.984 |
| Overall yield | 0.912 | 0.895 | 0.879 | 0.870 | 0.854 | 0.837 |

-continued

8.
Lys-Leu-Glu-Arg-Ser-Thr-Val-Met, (SEQ ID NO: 10)

9.
Lys-Leu-Glu-Arg-Ser-Thr-Val-Met-Ile, (SEQ ID NO: 11)

10.
Lys-Leu-Glu-Arg-Ser-Thr-Val-Met-Ile-Lys, (SEQ ID NO: 12)

11.
Lys-Leu-Glu-Arg-Ser-Thr-Val-Met-Ile-Lys-Gly, (SEQ ID NO: 13)

12.
Lys-Leu-Glu-Arg-Ser-Thr-Val-Met-Ile-Lys-Gly-Asp. (SEQ ID NO: 5)

The coupling efficiency of each amino acid was calculated to be greater than 98% in each instance across the entire 12-mer peptide and the overall yield of the 12 amino acid peptide was calculated as 83.74%. See Table 5.

The process above was repeated with a 12-mer homopolymeric peptide AAAAAAAAAAAA (SEQ ID NO: 14). The coupling formulation used for this peptide synthesis is from Table 2 and comprised Boc-Ala-OH. Coupling yield was determined from fluorescence intensity at each synthesis step, as described above. Table 6 shows the fluorescence signal intensity, the yield efficiency for each coupling step, and the overall yield at each step of synthesis of the polyA peptide.

TABLE 6

|  | 1 mer | 2 mer | 3 mer | 4 mer | 5 mer | 6 mer |
|---|---|---|---|---|---|---|
| Peptide Sequence | A | AA | AAA | AAAA (SEQ ID NO: 15) | AAAAA (SEQ ID NO: 16) | AAAAAA (SEQ ID NO: 17) |
| Fluorescence signal intensity | 61000 | 60363.4 | 59558.98 | 58826 | 58231 | 57436.8 |
| Yield for each coupling | 1 | 0.990 | 0.988 | 0.988 | 0.988 | 0.988 |
| Overall yield | 1 | 0.990 | 0.976 | 0.964 | 0.955 | 0.942 |

|  | 7 mer | 8 mer | 9 mer | 10 mer | 11 mer | 12 mer |
|---|---|---|---|---|---|---|
| Peptide Sequence | AAAAAAA (SEQ ID NO: 18) | AAAAAAAA (SEQ ID NO: 19) | AAAAAAAAA (SEQ ID NO: 20) | AAAAAAAAAA (SEQ ID NO: 21) | AAAAAAAAAAA (SEQ ID NO: 22) | AAAAAAAAAAAA (SEQ ID NO: 14) |
| Fluorescence signal intensity | 56705.9 | 56001.23 | 55289.1 | 54576.6 | 53888.2 | 53212.3 |
| Yield for each coupling | 0.988 | 0.988 | 0.988 | 0.988 | 0.988 | 0.988 |
| Overall yield | 0.930 | 0.918 | 0.906 | 0.895 | 0.883 | 0.872 |

Examples 4 and 5 illustrate a key advantage of the present invention; coupling efficiency >98% is stably maintained for each step of peptide synthesis. Because the coupling efficiency is high and stable, each feature has a relatively greater fraction of intended full length peptide and relatively lower fraction of less than full length contaminants. For example, more than 80% of the peptide molecules comprising a 12-mer peptide feature would be full length, and 70% of molecules in a 20-mer peptide feature would be full length. As we demonstrate in Example 6, this is a remarkable advance of the prior art methods.

Example 6: Comparison with Prior Art Array Synthesis

Materials and Methods:

We followed a standard prior art peptide array synthesis based on the Merrifield solid phase peptide synthesis [(R. B. Merrifield (1963). "Solid Phase Peptide Synthesis. I. The Synthesis of a Tetrapeptide". *J. Am. Chem. Soc.* 85 (14): 2149-2154) Pellois, J P et al., "Individually addressable parallel peptide synthesis on microchips". *Nat Biotechnology* 2002 September: 20(9):922-6). We determined the coupling efficiency for each step. All Boc-protected amino acids and Hobt (hydroxybenzotriazole) were obtained from AAPPTEC. Wafers with silicon oxide were purchased from University Wafers. Diisopropyl carbodiimide was obtained from Creosalus. 99% by weight sulfuric acid in water and 33% by weight hydrogen peroxide in water are obtained from Sigma Aldrich. Piranha solution was prepared by mixing a solution with a final concentration of 50% sulfuric acid and 50% hydrogen peroxide. Aminopropyl triethoxysilane and ethanol are obtained from Sigma Aldrich. Dimethyl formamide (DMF), Dichloromethane (DCM), acetic anhydride, N-methyl-2-pyrrolidinone (NMP), and acetone and isopropyl alcohol solution (IPA) were obtained from VWR. Polymethylmethacrylate (PMMA) was obtained from Polysciences Inc., Bis(4-tert-butyl phenyl) Iodonium Hexafluoroantimonate (Photoacid generator (PAG) was obtained from Hampford Research. Isopropylthioxanthenone (ITX) was obtained from Sigma Aldrich. PGMEA (propylene glycol methyl ether acetate) was obtained from Alfa Aesar. Diisopropyl ethylamine (DIEA) was obtained from Alfa Aesar.

Wafers were cleaned with piranha solution. These wafers are dipped with 0.5% aminopropyltriethoxy silane in ethanol for 15 minutes and then washed with ethanol. Now the wafers are cured at 110° C. for 30 minutes in a nitrogen bake oven. Amino acid and activator solution was prepared as follows: 0.1M Boc-Gly-OH, 0.1M DIC and 0.1M Hobt were dissolved in N-methyl-2-pyrrolidinone. The wafers were then immersed in this solution for 30 minutes in a vessel to form the first layer. The wafers were then washed with DCM/DMF (1:1,v/v), DMF, DCM, and DMF in sequence respectively by shaking in a vessel for 5 minutes each at 100 rpm. 50% by weight acetic anhydride solution in DMF was then added to the wafers for capping. The wafers were then washed with DMF and IPA.

Heteropolymeric Sequence:

We prepared a photoresist solution of 2.5% by weight PMMA, 5% by weight PAG and 5% by weight ITX dissolved in PGMEA (88.5% by weight). This resist formulation was spin coated at 2000 rpm for 60 seconds and then post baked at 85° C. for 90 seconds. The wafers were then cooled at 23° C. for 5 minutes. These wafers were then exposed at 40 mJ/cm$^2$ with one reticle over the whole wafer in deep UV scanner. Next, the wafers were baked at 65° C. for 1 min. on a hot plate. The wafers were then soaked with Acetone and DI water for 2 minutes each. They were then air dried with nitrogen. The wafer was washed with 5% DIEA in DMF for 10 minutes.

All Boc-amino acids were obtained from AAPPTEC and was mixed with 0.1M DIC and 0.1M Hobt and dissolved in NMP. The wafers were then immersed with this solution for 30 mins followed by wash with DCM/DMF as in step 1. Then the wafers were capped with 50% Acetic anhydride/ DMF solution for 30 mins. The non homopolymeric sequence was synthesized as KLERSTVMIKGD (SEQ ID NO: 5).

Coupling Yield Test:

5,6 FAM Carboxyfluorescein was obtained from Anaspec. 0.1M Boc-Gly-OH (from AAPPTeC), 0.1M Hobt (Sigma Aldrich) and 0.1M DIC (Creosalus) was dissolved in NMP. The wafers were dipped in this solution covered in dark for 1 hour to detect the coupling yield.

The coupling yield was calculated using the formula E=10^((log F)/C) where F equals fraction of full length and C=number of couplings=length−1. The formula used to calculate step yield was: Step yield=$(F_n/F_1)^{1/n-1}$, where $F_1$ and $F_n$ denotes the fluorescein coupling intensity read out from a fluorescent scanner device at the first step and the nth step.

Figure 7A:
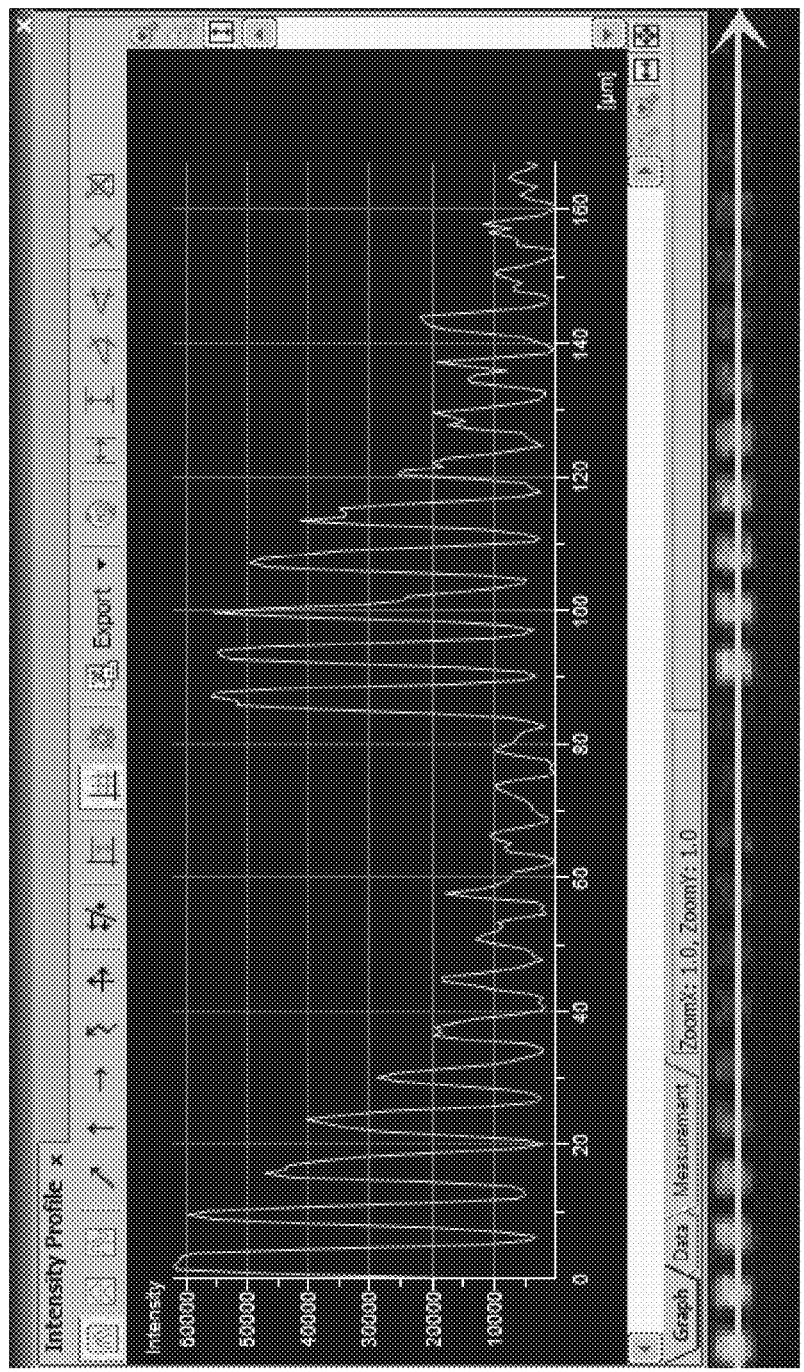
FIG. 7A shows the readout of the fluorescence signal from a 1-12 mer synthesis of polymeric peptide using standard synthesis-on-a-chip methods.
Figure 8A:
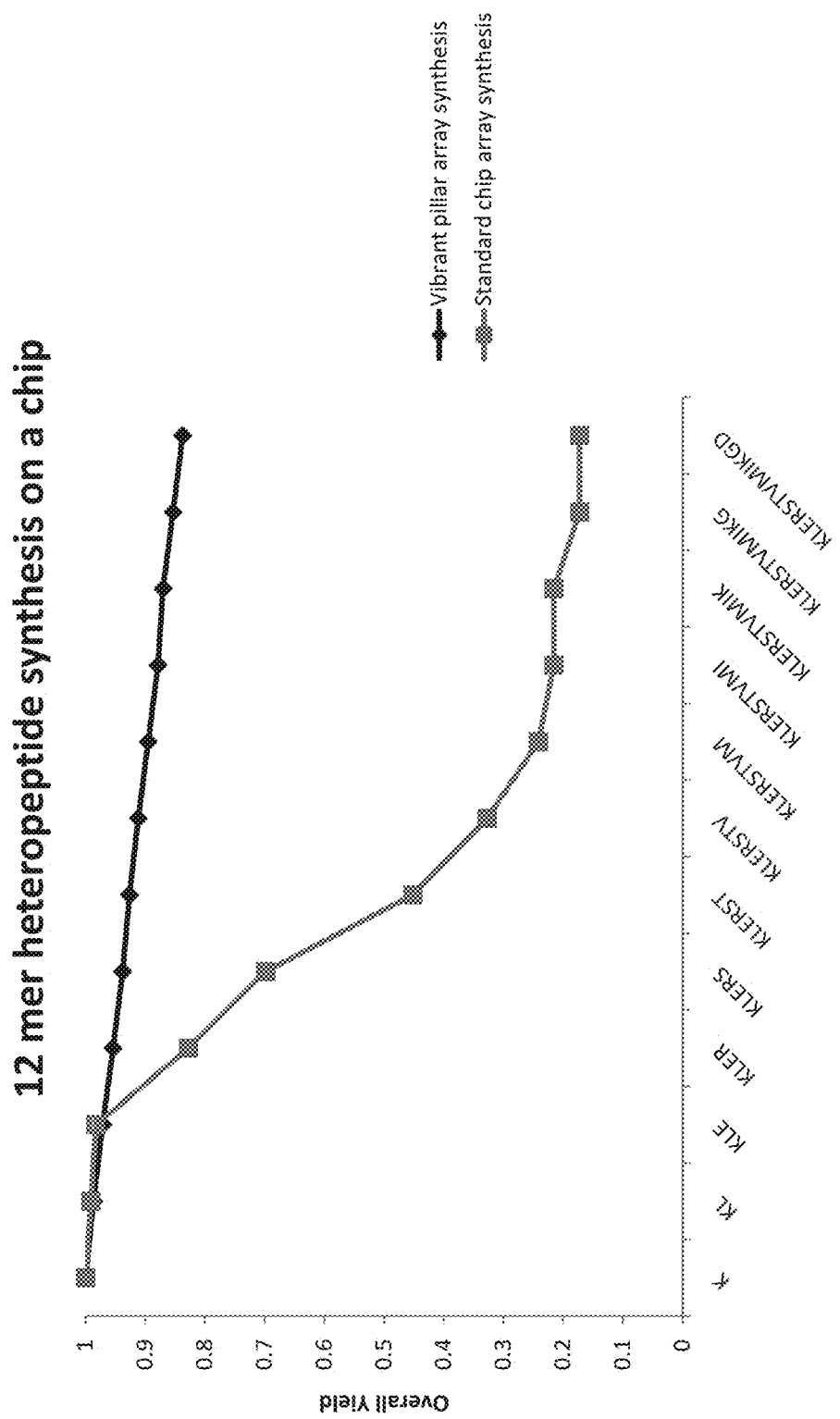
FIG. 8A shows a comparison of synthesis yield for a 1-12 mer synthesis of heteropolymeric peptides (SEQ ID NOS: 6-13, and 5, respectively, in order of appearance) using the method described herein vs. the standard chip array synthesis.
Figure 8B:
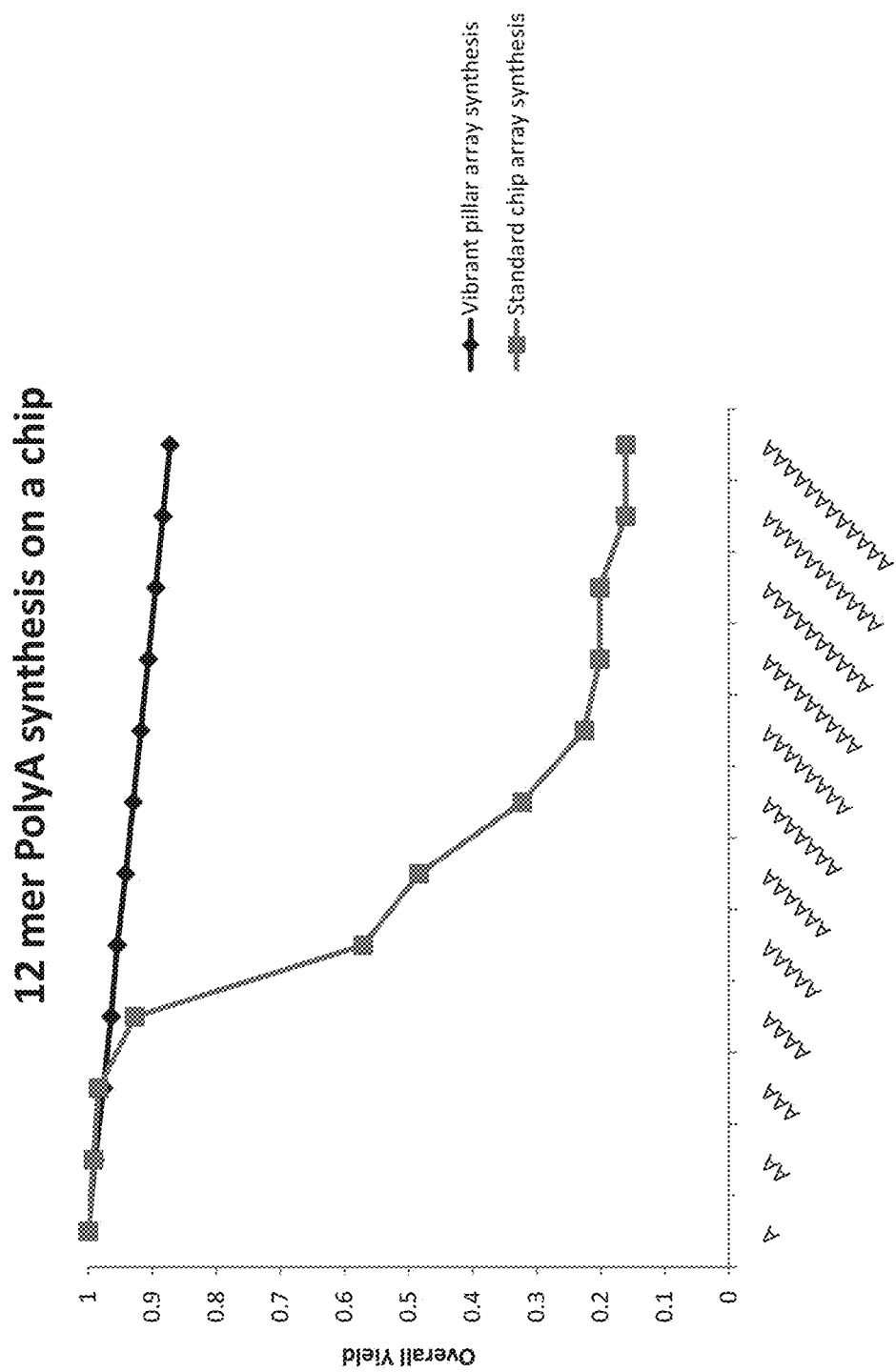
FIG. 8B shows a comparison of synthesis yield for a 1-12 mer synthesis of polyA peptides (SEQ ID NOS: 15-22, and 14, respectively, in order of appearance) using the method described herein vs. the standard chip array synthesis.
Figure 8C:
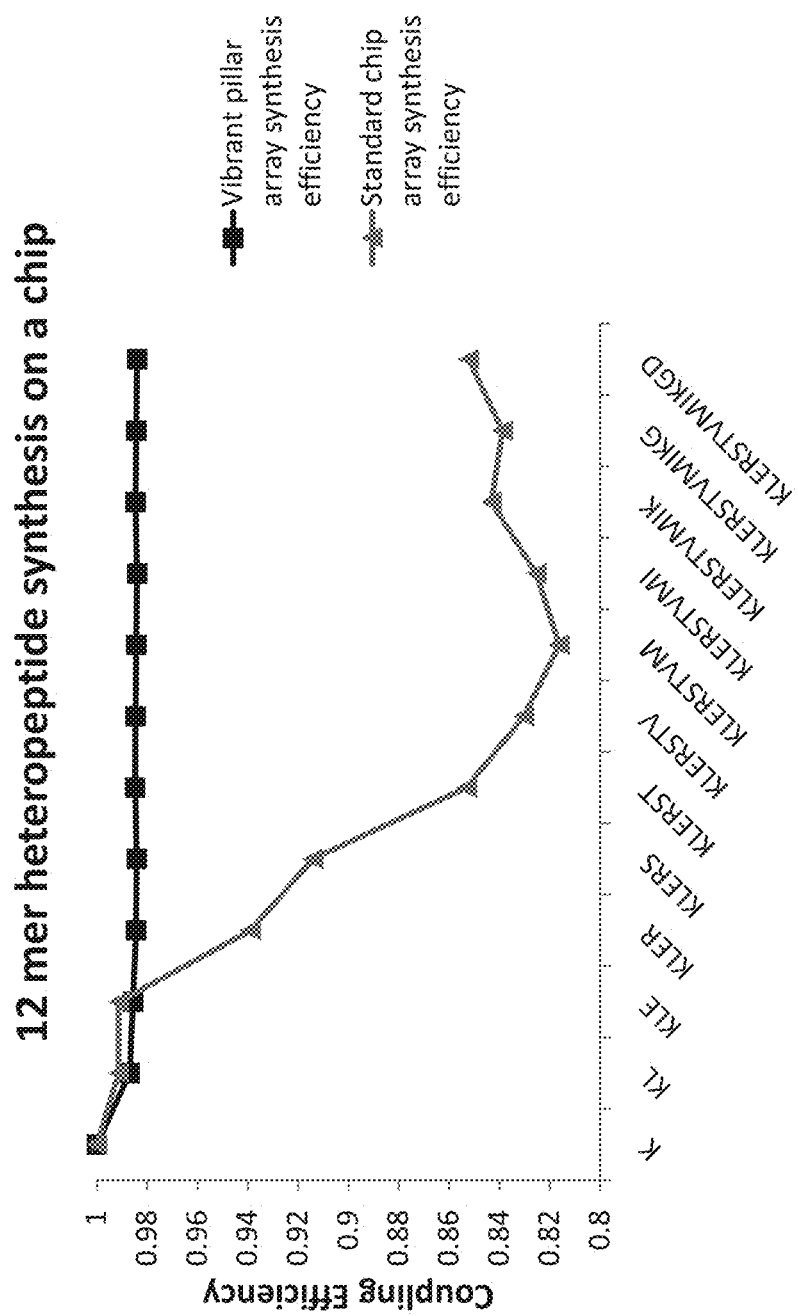
FIG. 8C shows a comparison of coupling efficiency for a 1-12 mer synthesis of heteropolymeric peptides (SEQ ID NOS: 6-13, and 5, respectively, in order of appearance) using the method described herein vs. the standard chip array synthesis.

FIG. 7A shows an image of the chip with intensity from left to right provides a measure of efficiency of total synthesis from 1 to 12 peptides of the 'KLERSTVMIKGD' (SEQ ID NO: 5) peptide in duplicate (2 series) (bottom) and intensity profile graph for each spot (top). Table 7 shows the numerical value of fluorescence signal intensity from FIG. 7A, the yield efficiency for each coupling step, and the overall yield. FIG. 8A shows a plot of the stepwise synthesis overall yield of the peptide 'KLERSTVMIKGD' (SEQ ID NO: 5) on a chip using the Vibrant chip and method described above (results in Table 5) vs. the standard synthesis of a chip (results in Table 7). FIG. 8C shows plot of stepwise synthesis coupling efficiency of the peptide 'KLERSTVMIKGD' (SEQ ID NO: 5) on a chip using the Vibrant chip and method described above (results in Table 5) vs. the standard synthesis of a chip (results in Table 7). As can be seen from the results, the efficiency of synthesis is significantly improved for peptides greater than 3 amino acids in length using our method.

TABLE 7

|  | 1 mer | 2 mer | 3 mer | 4 mer | 5 mer | 6 mer |
|---|---|---|---|---|---|---|
| Peptide Sequence | K | KL | KLE | KLER (SEQ ID NO: 6) | KLERS (SEQ ID NO: 7) | KLERST (SEQ ID NO: 8) |
| Fluorescence signal intensity | 58000 | 57500 | 57000 | 48000 | 40500 | 26200 |
| Yield for each coupling | 1 | 0.991 | 0.991 | 0.939 | 0.914 | 0.853 |
| Overall yield | 1 | 0.991 | 0.982 | 0.828 | 0.698 | 0.452 |

|  | 7 mer | 8 mer | 9 mer | 10 mer | 11 mer | 12 mer |
|---|---|---|---|---|---|---|
| Peptide Sequence | KLERSTV (SEQ ID NO: 9) | KLERSTVM (SEQ ID NO: 10) | KLERSTVMI (SEQ ID NO: 11) | KLERSTVMIK (SEQ ID NO: 12) | KLERSTVMIKG (SEQ ID NO: 13) | KLERSTVMIKGD (SEQ ID NO: 5) |
| Fluorescence signal intensity | 19000 | 14000 | 12500 | 12500 | 10000 | 10000 |
| Yield for each coupling | 0.830 | 0.816 | 0.825 | 0.843 | 0.839 | 0.852 |
| Overall yield | 0.328 | 0.241 | 0.216 | 0.216 | 0.172 | 0.172 |

Homopolymeric Sequence:

We prepared a photoresist solution of 2.5% by weight PMMA, 5% by weight PAG and 5% weight ITX dissolved in PGMEA (88.5% by weight). This resist was spin coated at 2000 rpm for 60 seconds and then post baked at 85° C. for 90 seconds. The wafers were then cooled at 23° C. for 5 minutes. These wafers were then exposed at 40 mJ/cm² with one reticle over the whole wafer in deep UV scanner. Next, the wafers were baked at 65° C. for 1 minute on a hot plate. The wafers were then soaked with acetone and DI water for 2 minutes each. They were then air dried with nitrogen. The wafer was then washed with 5% DIEA in DMF for 10 minutes.

0.1M Boc-Ala-OH obtained from AAPPTEC was mixed with 0.1M DIC and 0.1M Hobt and dissolved in NMP. The wafers were then immersed with this solution for 30 minutes followed by wash with DCM/DMF as in step 1. Then the wafers were capped with 50% Acetic anhydride/DMF solution for 30 minutes.

These steps were followed for all the 12 layers of Alanine.

Coupling Yield Test:

5,6 FAM Carboxyfluorescein was obtained from Anaspec. 0.1M Boc-Gly-OH (from AAPPTeC), 0.1M Hobt (Sigma Aldrich) and 0.1M DIC (Creosalus) was dissolved in NMP. The wafers were dipped in this solution covered in dark for 1 hour to detect the coupling yield.

The coupling yield was calculated using the formula E=10^((log F)/C) where F equals fraction of full length and C=number of couplings=length−1. The formula used to calculate step yield was: Step yield=$(F_n/F_1)^{1/n-1}$, where $F_1$ and $F_n$ denotes the fluorescein coupling intensity read out from a fluorescent scanner device at the first step and the nth step.

Figure 7B:
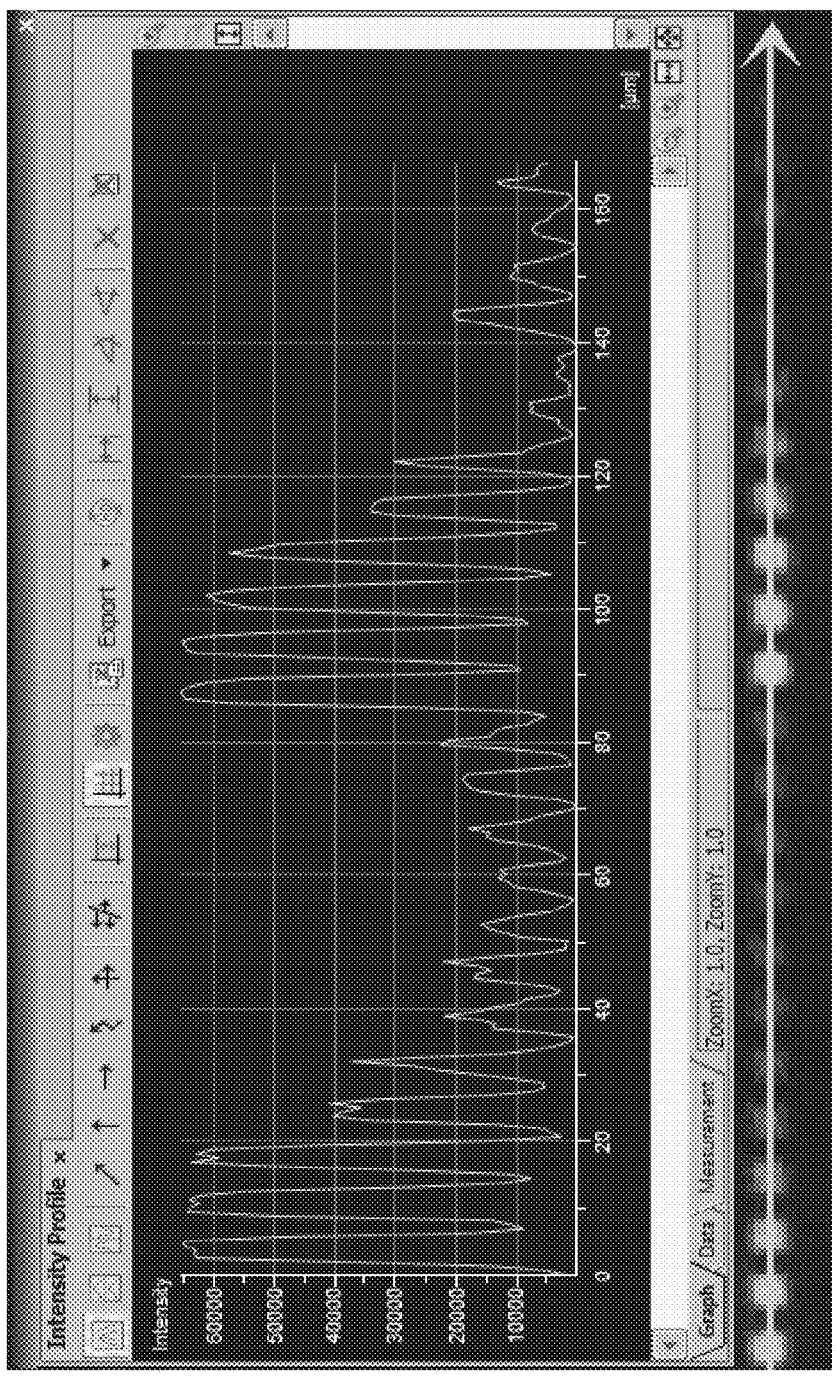
FIG. 7B shows the readout of the fluorescence signal from a 1-12 mer synthesis of polyA peptide using standard synthesis-on-a-chip methods.
Figure 8D:
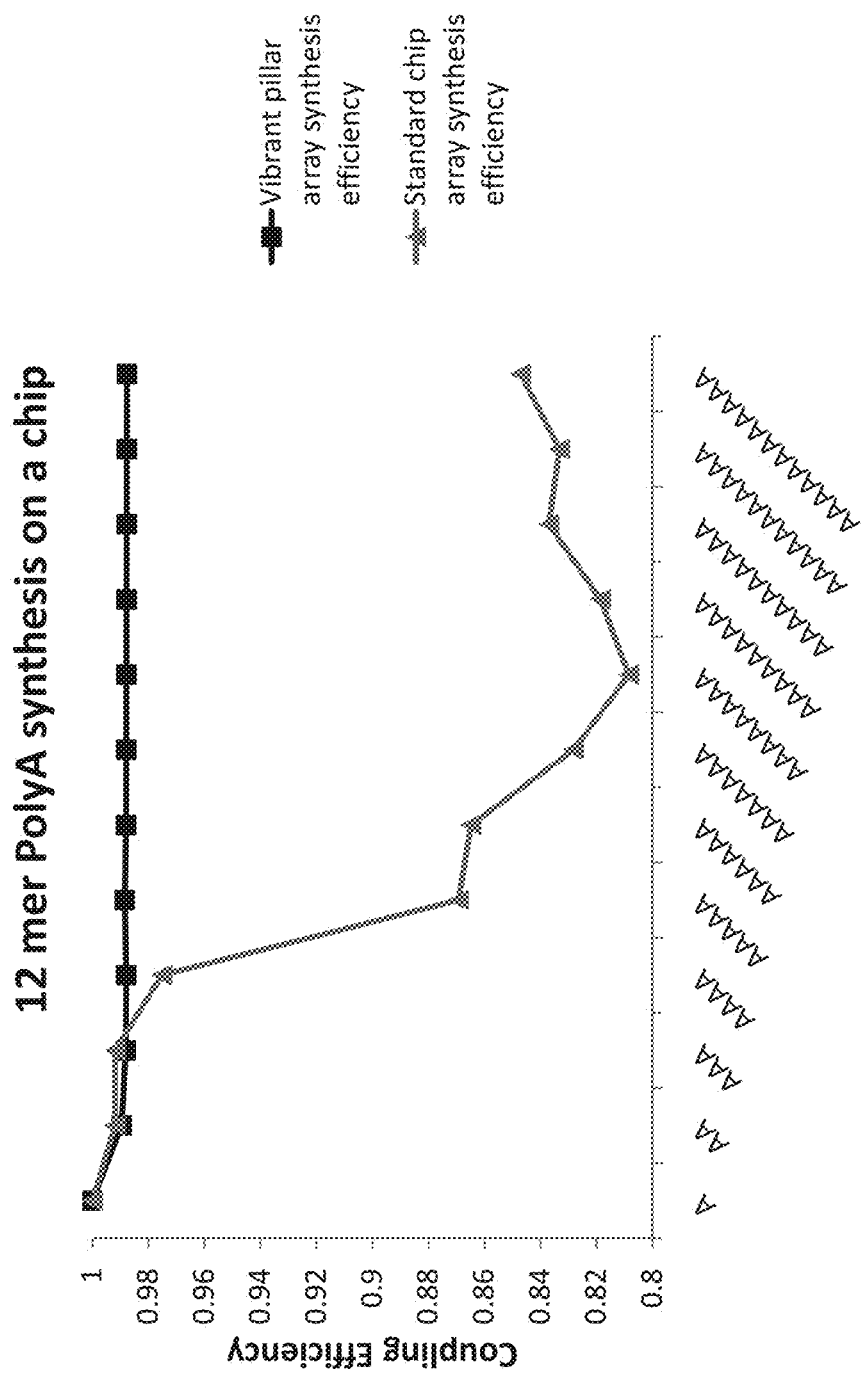
FIG. 8D shows a comparison of coupling efficiency for a 1-12 mer synthesis of polyA peptides (SEQ ID NOS: 15-22, and 14, respectively, in order of appearance) using the method described herein vs. the standard chip array synthesis.

FIG. 7B shows an image of the chip with intensity from left to right provides a measure of efficiency of total synthesis from 1 to 12 peptides of the polyA peptide in duplicate (2 series) and intensity profile graph for each spot. Table 8 shows the numerical value of fluorescence signal intensity from FIG. 7B, the yield efficiency for each coupling step, and the overall yield. FIG. 8B shows a plot of the polyA synthesis on a chip using the Vibrant chip and method described above (results in Table 6) vs. the standard synthesis of a chip (results in Table 8). FIG. 8D shows plot of stepwise synthesis coupling efficiency of the polyA synthesis on a chip using the Vibrant chip and method described above (results in Table 6) vs. the standard synthesis of a chip (results in Table 8). As can be seen from the results, the efficiency of synthesis is significantly improved for peptides greater than 3 amino acids in length using our method.

of performing quality control after completing the manufacturing of an entire batch process of wafers.

All 20 water based coupling solutions were prepared as follows: The inert water soluble polymers (3% by weight PVP and 7% by weight PVA) were dissolved in the ratio of 1:2.5 in deionized (DI) water which makes up about 10% by weight of the solution along with 2% by weight amino acid concentration. 4% by weight of each EDC and HonB were added as reagents twice the concentration of amino acids. 4% by weight DIEA was added at the same concentration as EDC and HoNb. This water coupling solution was spin coated on a derivatized substrate to form a uniform solid layer all available to couple to the substrate. The wafer was then baked on a hot plate for 2 minutes at 90° C. to remove the remaining solvent (DI water) and coupled at the same time. Next the coupling coat was washed away with DI water in a strip module.

5,6 fAM Carboxy fluorescein was obtained from Anaspec. 0.1M Boc-Gly-OH (from AAPPTeC), 0.05M 5,6FAm and 0.1M HoNb (Sigma Aldrich) and 0.1M EDC (Sigma

TABLE 8

|  | 1 mer | 2 mer | 3 mer | 4 mer | 5 mer | 6 mer |
| --- | --- | --- | --- | --- | --- | --- |
| Peptide Sequence | A | AA | AAA | AAAA (SEQ ID NO: 15) | AAAAA (SEQ ID NO: 16) | AAAAAA (SEQ ID NO: 17) |
| Fluorescence signal intensity | 62000 | 61500 | 61000 | 57500 | 35400 | 30000 |
| Yield for each coupling | 1 | 0.992 | 0.992 | 0.975 | 0.869 | 0.864 |
| Overall yield | 1 | 0.992 | 0.984 | 0.927 | 0.571 | 0.484 |

|  | 7 mer | 8 mer | 9 mer | 10 mer | 11 mer | 12 mer |
| --- | --- | --- | --- | --- | --- | --- |
| Peptide Sequence | AAAAAAA (SEQ ID NO: 18) | AAAAAAAA (SEQ ID NO: 19) | AAAAAAAAA (SEQ ID NO: 20) | AAAAAAAAAA (SEQ ID NO: 21) | AAAAAAAAAAA (SEQ ID NO: 22) | AAAAAAAAAAAA (SEQ ID NO: 14) |
| Fluorescence signal intensity | 20000 | 14000 | 12500 | 12500 | 10000 | 10000 |
| Yield for each coupling | 0.828 | 0.808 | 0.819 | 0.837 | 0.833 | 0.847 |
| Overall yield | 0.323 | 0.226 | 0.202 | 0.202 | 0.161 | 0.161 |

Example 7: Coupling of Amino Acids to a Substrate

This example provides the typical signature of how the coupling steps perform on a microarray platform using all 20 amino acids in water-based coupling solutions on two substrates (i.e., wafers) and signal intensity as a read-out. This test was run as a quality control on each batch of wafer (substrate) to match the performance. For each experiment, the measured signal intensity gives a direct relation of the coupling yield.

Derivatized substrate was obtained as described in Example 1. All couplings of amino acids mentioned in this example were coupled as described below. The same steps were repeated on all wafers done in a batch. This is a method Aldrich) was dissolved in water along with 5% by weight Poly vinyl pyrrollidone (PolySciences). This solution is called the fluorescein coupling solution. This solution was spin coated on the wafer at 2000 rpm to form a coupling dye coat. Then the wafers were baked at 65° C. for 2 mins and then the dye solution was washed away with water. This completes the coupling of fluorescein dye to measure the signals. The signal was then read off a fluorescence microscope.

Capping Solution was Prepared as Follows:

Acetic anhydride was obtained from Sigma Aldrich Corp. PVP was dissolved in N methyl pyrrolidone which makes up about 1-2% of the total solution, thus the contents of the solution were as follows: PVP— 1-2% by weight. Acetic Anhydride 20-30% by weight and the remainder was N methyl pyrrolidone. Then acetic anhydride was added to make up about 20-30% by weight of the solution. This capping solution was spin coated on the wafers in a capping module by spinning the wafers at 2000 rpm for 30 sec. The wafers were then baked in a cap bake module for up to 2 minutes at 75° C. to complete the capping process. The remaining solution was washed away with DI water in a strip module.

The above procedure was followed for coupling each amino acid. Thus to grow a 12-mer amino acid peptide chain using all the twenty amino acids uses 240 steps. Fluorescein was coupled as explained above to read the data out from the fluorescein scanner (Nikon AIR Confocal Scanner).

Figure 9:
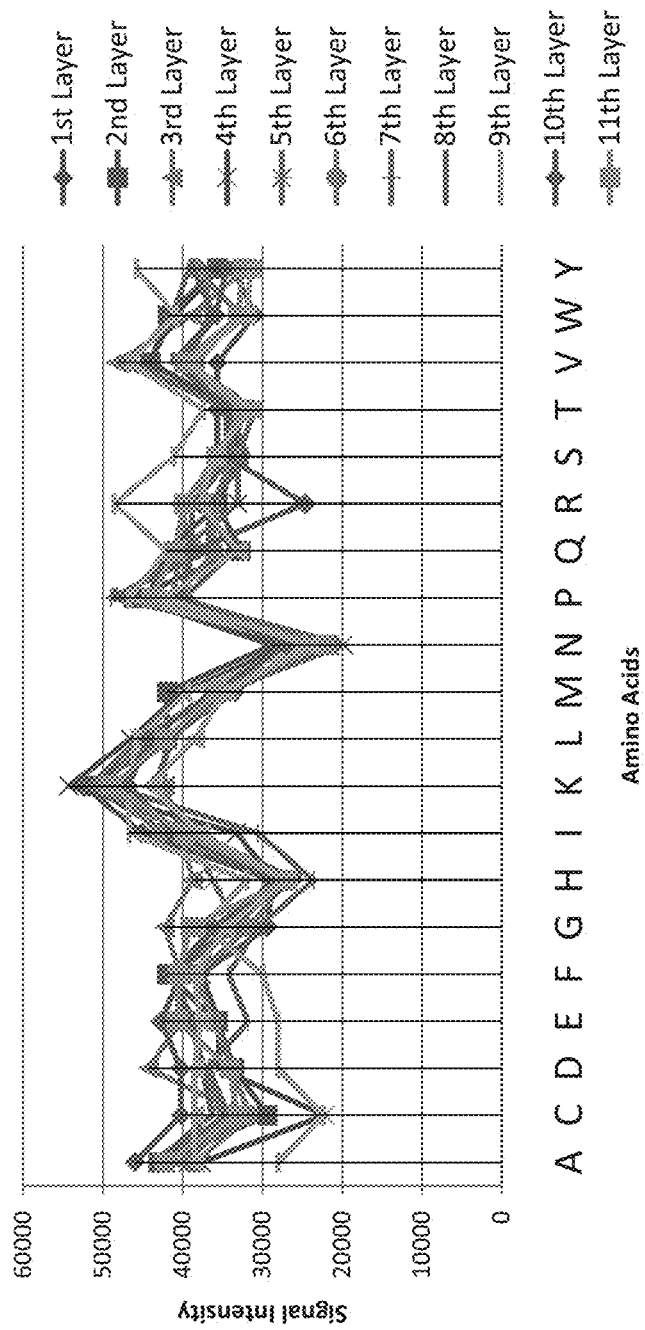
FIG. 9 shows the signal intensity for all twenty amino acids across 12 layers.

In this example, amino acids Ala-Cys-Asp-Glu-Phe-Gly-His-Ile-Lys-Leu-Met-Asn-Pro-Gln-Arg-Ser-Thr-Val-Trp-Tyr (SEQ ID NO: 60) were used to synthesize and fill the microarray using the procedures described above. FIG. 9 shows the fluorescence signal intensity of each amino acid at each layer. Amino acids His, Asn, and Trp showed a lower value due to fluorescein quenching. The graph in FIG. 9 shows an upward curve after these amino acids hence showing high coupling yield on every synthesis step.

FIG. 10 shows the normalized signal intensity for all twenty amino acids grown at each layer (total of 12 layers) on each of the wafers tested. Normalized data=(Raw fluorescence signal intensity/(sum value of each layer/Average of fluorescence signal intensity sum across all layers)). Thus, coupling yield (as measured via signal intensity) remains high across each amino acid and each layer, with the exception of His, Asn, and Trp due to fluorescein quenching.

Example 8: Testing of Water-Based Photoactive Formulations

Materials and Methods

Polymers—polyethylene glycol monomethyl ether, Polyvinyl pyrrollidone, Poly(2-dimethylaminoethyl methacrylate), Poly(2-hydroxypropyl methacrylate), Poly 4 vinyl pyridine were obtained from Polysciences.

Photoacid generators 4 Methoxyphenyl)phenyliodonium trifluoromethanesulfonate, (4 methoxyphenyl)dimethylsulfonium triflate, (2,4-dihydroxyphenyl)dimethylsulfonium triflate were obtained from Hamilton Research Inc.

Isopropyl thioxanthenone and ethyl lactate was obtained from Sigma Aldrich.

Photoactive Formulations:

Water resist-1 was prepared by mixing the polymer polyethylene glycol monomethyl ether (2% by weight) and polyvinyl pyrrollidone (2% by weight) in water and letting it dissolve overnight. 4 Methoxyphenyl)phenyliodonium trifluoromethanesulfonate (5% by weight) was added along with isopropyl thioxanthenone (5% by weight) and dissolved overnight. Water resist-2 was prepared by mixing the polymer Poly(2-dimethylaminoethyl methacrylate) (2.5% by weight) in a solvent of water (90% by weight) and ethyl lactate (10% by weight) and letting it dissolve overnight. (4 methoxyphenyl)dimethylsulfonium triflate (5% by weight) was added along with isopropyl thioxanthenone and dissolved overnight.

For all other resists—water and non-water were prepared the same way as described above. Letting the polymer dissolve overnight in the corresponding solvent and then adding the photoacid generator and/or photoinitiator in the specified amounts.

Substrates were obtained as described in Example 1. Then wafers were surface derivatized. Once the resists were prepared, the resists were spin coated onto the substrate at speeds varying from 1000 rpm to 2000 rpm to obtain the desired thickness. For example, water resist 1 was spun at 2000 rpm to obtain a 0.2 µm thickness. The wafers were then exposed in a Nikon S 203 scanner for varying exposure energy from 6 mJ/cm$^2$ to 26 mJ/cm$^2$. Next the wafers were post baked at 85° C. in a hot plate for 2 mins and then the resist was stripped with water.

EDC—1-ethyl-3-(3-dimethylaminopropyl) carbodiimide), and HonB—n hydroxy 5 norbornene 2,3 di carboximide were obtained from Sigma Aldrich corp. DIEA—Di isopropyl ethylamine was obtained from Sigma Aldrich Corp.

Boc-Gly-OH was obtained from AAPPTEC/Anaspec. The inert water soluble polymer PVP and PVA were dissolved in the ratio of 1:2.5 in deionized (DI) water which makes up about 10% by weight of the solution along with 1-2% by weight amino acid concentration. EDC and HonB were added as reagents at 2× the percentage by weight of Boc-Gly-OH. Di isopropyl ethylamine was added at the same percentage by weight concentration as EDC and HoNb. This water coupling solution was spin coated on a substrate to form a uniform solid layer available to couple to the substrate below. The wafer was then baked on a hot plate for 2 minutes at 90° C. to remove the remaining solvent (DI water) and coupled at the same time. Next the coupling coat was washed away with DI water in a strip module.

Capping Solution was Prepared as Follows:

Acetic anhydride was obtained from Sigma Aldrich Corp. PVP was dissolved in N methyl pyrrolidone which makes up about 1-2% by weight of the total solution. Next acetic anhydride was added to make up about 20-30% by weight of the solution. This capping solution was spin coated on the wafers in a capping module by spinning the wafers at 2000 rpm for 30 seconds. The wafers were next baked in a cap bake module for up to 2 minutes at 75° C. to complete the capping process. The remaining solution was washed away with DI water in a strip module.

5,6 fAM Carboxy fluorescein was obtained from Anaspec. 0.1M Boc-Gly-OH (from AAPPTeC), 0.05M 5,6FAm and 0.1M HoNb (Sigma Aldrich) and 0.1M EDC (Sigma Aldrich) was dissolved in water along with 5-10% by weight Poly vinyl pyrrollidone (PolySciences). This solution is called fluorescein coupling solution. This solution was spin coated on the wafer at 2000 rpm to form a coupling dye coat. Next the wafers were baked at 65° C. for 2 mins and then the dye solution was washed away with water. This completes the coupling of fluorescein dye to measure the signals. The signal was then read off a fluorescence microscope. For all the experiments, the measured signal intensity gives a direct relation of the coupling yield. The deprotection yield can be calculated by the amount of fluorescein coupled to the glycine on the substrate.

Comparison of Different Resists to Water Resist-1 and Water Resist-2

Water resist-1 and water resist-2 are not chemically amplified resists. These resists do not have a t-boc in the backbone and hence no chemical amplification takes place. The post exposure bake is performed to diffuse the initial acid formed to reach the substrate. Hence the thinner the photoresist, the easier it is for diffusion of photoacid.

Exposure energy was tested in the range of 10-100 mJ/cm$^2$. The fluorescent signal intensity shown in FIG. 11 is a relative scale from 0 to 65,000.

The performance of various resist combinations was thus tested ((1 wt % pmma 2 wt % PAG 2 wt % ITX, 0.5 wt % poly 2 hydroxypropyl methacrylate 1 wt % PAG 1 wt % ITX, 1 wt % pmma 2 wt % PAG 2 wt % ITX, 0.5 wt % polystyrene 1 wt % PAG, 0.5 wt % polystyrene 1 wt % PAG 1 wt % ITX, 0.5 wt % pmma 0.5 wt % polystyrene 1 wt % PAG, 0.25 wt % poly ethyl acrylate 0.5 wt % PAG 0.5 wt % ITX, 0.25 wt % polystyrene 0.5 wt % PAG 0.5 wt % ITX) Polymethyl methacrylate obtained from Polysciences Inc. (pmma), Photoacid generator (PAG), Isopropyl thio xanthenone obtained from Sigma Aldrich (ITX)).

Figure 11:
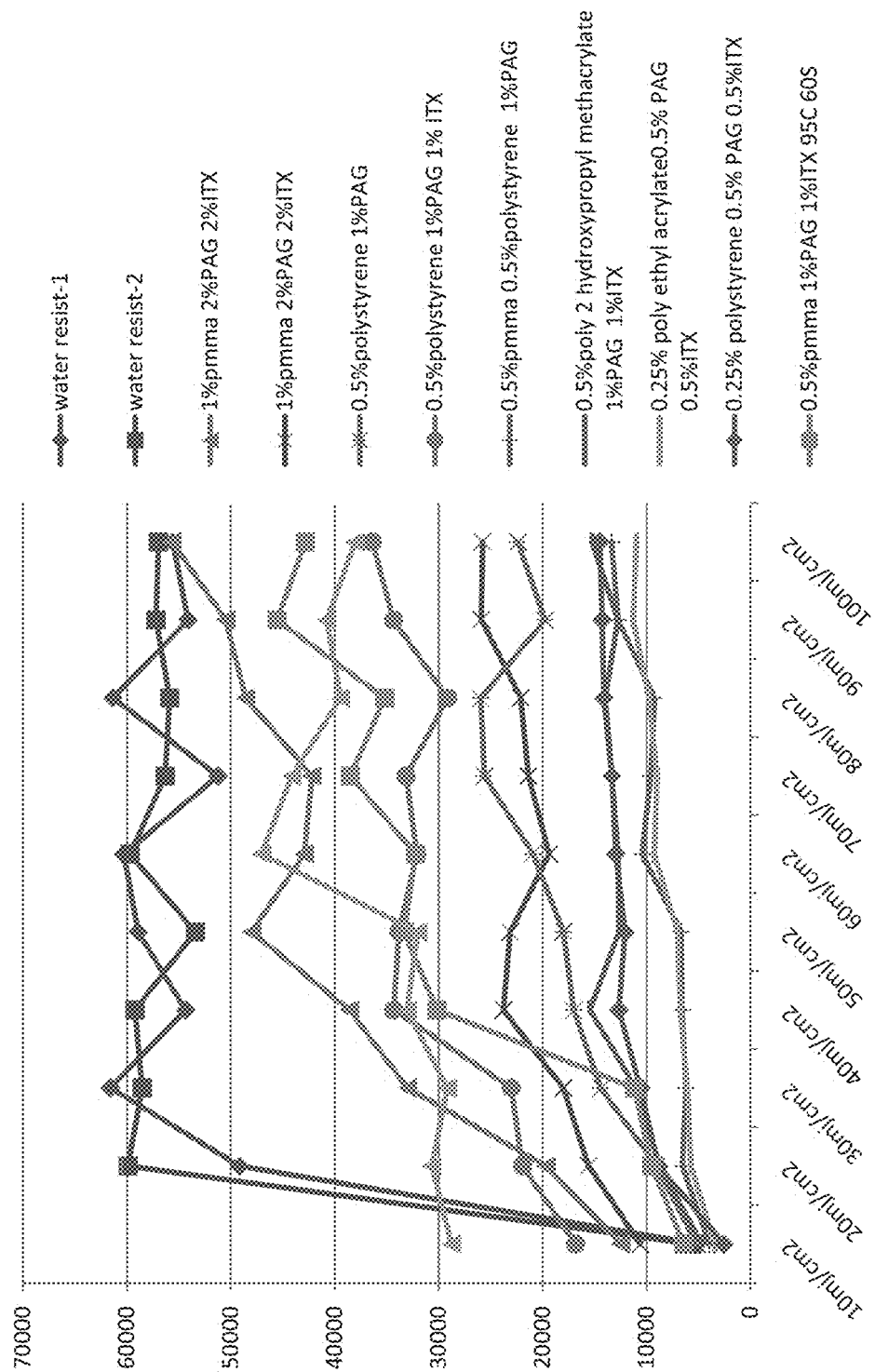
FIG. 11 shows the expose energy at which acid reaches the substrate for resist combinations. Expose energy is expressed in mJ/cm$^2$. Fluorescent signal intensity is a relative scale from 0 to 65,000.

FIG. 11 shows the expose energy at which acid reaches the substrate for each of the resist combinations tested. As can be seen, water resist-1 and 2 each reached higher fluorescent signal intensity at lower expose energy as compared the other tested resists. This difference between the water and non-water-based resists likely occurred due to the use of polymers in combination with the photoacid generators and thioxanthenone in the various non-water resist combinations. These polymers cannot generally be dissolved in water and thus a different organic solvent such as Pgmea or ethyl alcohol is usually used. Also, the stripping of these resists generally involves use of organic solvents like acetone which would still not completely strip them off the wafer substrate and will leave a residue. This impacts the coupling yield.

To attempt to improve the performance of some of the comparative non-water resists, they were post baked at higher temperature of 95 C and 105 C. This did not show any further improvement as shown in FIG. 11.

As can be seen in FIG. 11, water resist-1 and water resist-2 needs only approximately 10-20 mJ/cm$^2$ of expose energy for the initial acid to be produced, which diffuses down to reach the substrate upon post exposure bake. The lesser the expose energy required, the faster the speed of exposure since the expose energy is directly proportional to the expose time. This can improve throughput.

Thickness Effect on Water Resist Performance
Photoactive Formulations:

Water resist-1 was prepared by mixing the polymer polyethylene glycol monomethyl ether (2% by weight) and polyvinyl pyrrollidone (2% by weight) in water and letting it dissolve overnight. 4 Methoxyphenyl)phenyliodonium trifluoromethanesulfonate (5% by weight) was added along with isopropyl thioxanthenone (5% by weight) and dissolved overnight. Water resist-2 was prepared by mixing the polymer Poly(2-dimethylaminoethyl methacrylate) (2.5% by weight) in a solvent of water (90% by weight) and ethyl lactate (10% by weight) and letting it dissolve overnight. (4 methoxyphenyl)dimethylsulfonium triflate (5% by weight) was added along with isopropyl thioxanthenone and dissolved overnight. Water resist-3 was prepared by dissolving polymer polyethylene glycol monomethyl ether (2% by weight) and polyvinyl pyrrollidone (2% by weight) in a solvent mixture comprising 50% water and 50% ethyl lactate. 2,4-dihydroxyphenyl)dimethylsulfonium triflate (2.5% by weight) and (4 methoxyphenyl)dimethylsulfonium triflate (2.5% by weight) were added to this and were dissolved overnight. Water soluble ITX was added at 5% by weight. Water resist-4 was prepared by dissolving polymer poly(2-dimethylaminoethyl methacrylate) (2.5% by weight) in a solvent mixture comprising 50% water and 50% ethyl lactate. 2,4-dihydroxyphenyl)dimethylsulfonium triflate 2.5% and (4 methoxyphenyl)dimethylsulfonium triflate (2.5% by weight) were added to this and were dissolved overnight. Water soluble ITX was added at 5% by weight. Water resist-5 was prepared by dissolving polymer poly(2-hydroxypropyl methacrylate) (2.5% by weight) in a solvent mixture comprising 50% water and 50% ethyl lactate. 2,4-dihydroxyphenyl dimethylsulfonium triflate (2.5% by weight) and (4 methoxyphenyl)dimethylsulfonium triflate (2.5% by weight) were added to this and were dissolved overnight. Water soluble ITX was added at 5% by weight. Water resist-6 was prepared by dissolving polymer poly 4 vinyl pyridine (5% by weight) in a solvent mixture comprising 50% water and 50% ethyl lactate. 2,4-dihydroxyphenyl dimethylsulfonium triflate (2.5% by weight) and (4 methoxyphenyl)dimethylsulfonium triflate (2.5% by weight) were added to this and were dissolved overnight. Water soluble ITX was added at 5% by weight.

Figure 12:
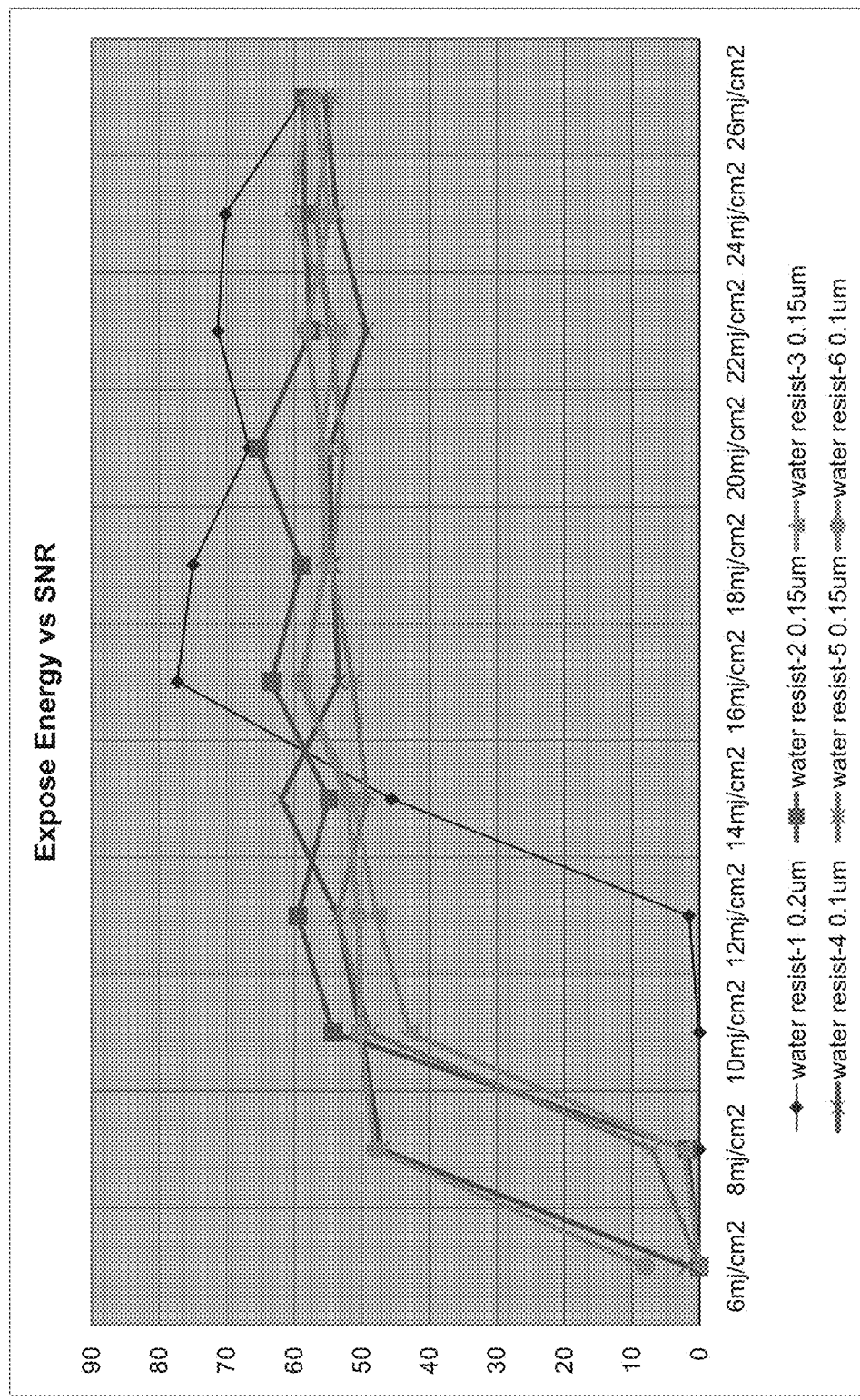
FIG. 12 shows the expose energy vs. (signal minus noise)/noise (SNR) for each of the indicated resists and thicknesses.
Figure 13:
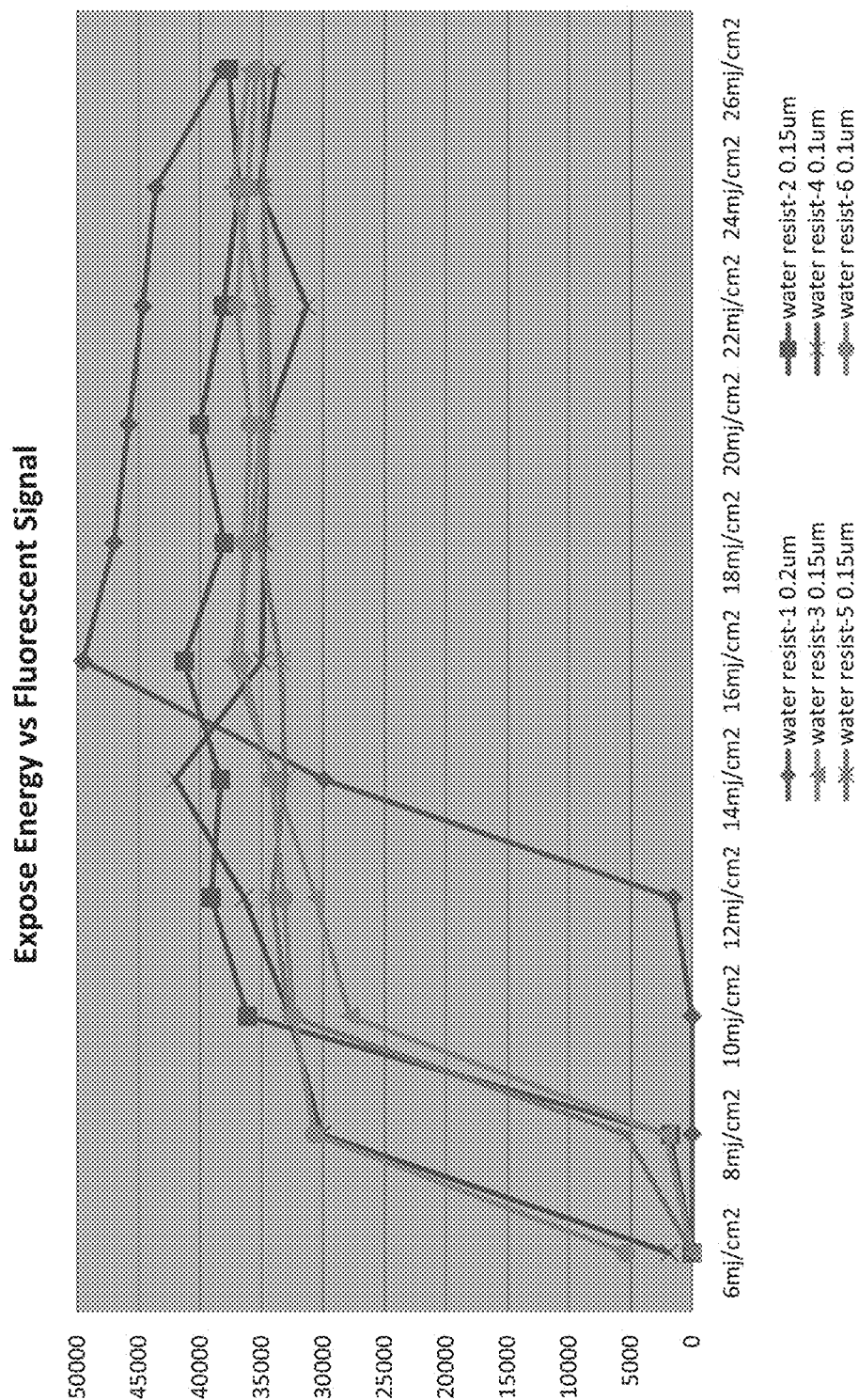
FIG. 13 shows the expose energy vs. fluorescent signal for each of the indicated resists and thicknesses.

FIG. 12 shows the expose energy vs. signal/noise (SNR) of resulting chips for water resist-1 0.2 µm, water resist-2 0.15 µm, water resist-3 0.15 µm, water resist-4 0.1 µm, water resist-5 0.15 µm, water resist-6 0.1 µm which were each spin coated at 1000 rpm-2000 rpm on a spin coat module to the indicated thickness. FIG. 13 shows the expose energy vs. fluorescent signal of resulting chips for each of the indicated resists and thicknesses. As can be seen in FIGS. 12-13, decreased thickness generally results in a lower energy requirement to effect acid diffusion. For example, water resist 2 with thickness 0.15 um diffuses acid at a lower energy compared to water resist 1 at 0.2 um. This pattern was observed across water resist-3 to water resist-6.

The presence of pillars on a substrate allows for a thinner coat of the photoresist, even as thin as 50 nm. This can lead to improved performance of water based photoresist.

Example 9: Production of Substrate with Carboxylic Acid Attachment Groups

This example describes how we constructed a porous layer with free carboxylic acid groups for polypeptide synthesis/attachment. Dextran Bio Xtra (MW40000) is obtained from Sigma Aldrich. Bis-Polyethylene glycol carboxy methyl ether was obtained from Sigma Aldrich. Poly vinyl pyrollidone 1000000 was obtained from Poly Sciences Inc. The above three polymers were dissolved in a solvent composition of 50% Ethyl lactate/50% water by weight in a ratio of 2:2:1 by weight along with 2% by weight photoacid generator dimethyl-2,4-dihydroxyphenylsulfonium triflate obtained from Oakwood Chemicals Inc. This solution was spin coated onto a wafer deposited with Nickel 1000A on a Silicon substrate. The spin speed was controlled at 3000 rpm to obtain a uniform coat of thickness 100 nm. The wafer was then exposed in a deep UV scanner Nikon S 203 at 250 mJ/cm$^2$ and then baked at 65° C. for 90 sec in a hot plate. The wafer was then stripped off the coat with acetone and isopropyl alcohol followed by a deionized water rinse. The substrate has a matrix of free COOH groups ready to be activated and coupled with a protein or an amino acid for peptide synthesis. The 2-dimensional concentration of COOH groups along the layer may be increased on a porous substrate as compared to a planar substrate.

Dextran was coupled onto a surface derivatized wafer. 1-ethyl-3-(3-dimethylaminopropyl) carbodiimide obtained from Pierce Scientific and N-Hydroxysuccinimide (NHS) obtained from Pierce Scientific were dissolved in deionized water in molar concentration of 0.2M and 0.1M respectively along with 10% by weight of Dextran. This coupling solution was spin coated to the wafer at a speed of 3000 rpm and baked at 65° C. for 90 sec to complete coupling of dextran-COOH substrate.

Bis-Polyethylene glycol carboxy methyl ether was coupled onto a surface derivatized wafer. 1-ethyl-3-(3-dimethylaminopropyl) carbodiimide obtained from Pierce Scientific and N-Hydroxysuccinimide (NHS) obtained from Pierce Scientific were dissolved in deionized water in molar concentration of 0.2M and 0.1M respectively along with 10% by weight of polyethylene glycol (PEG). This coupling solution was spin coated to the wafer at a speed of 3000 rpm and baked at 65° C. for 90 sec to complete coupling of PEG-COOH substrate.

Example 10: Overlapping Peptide Array Design

Figure 14:
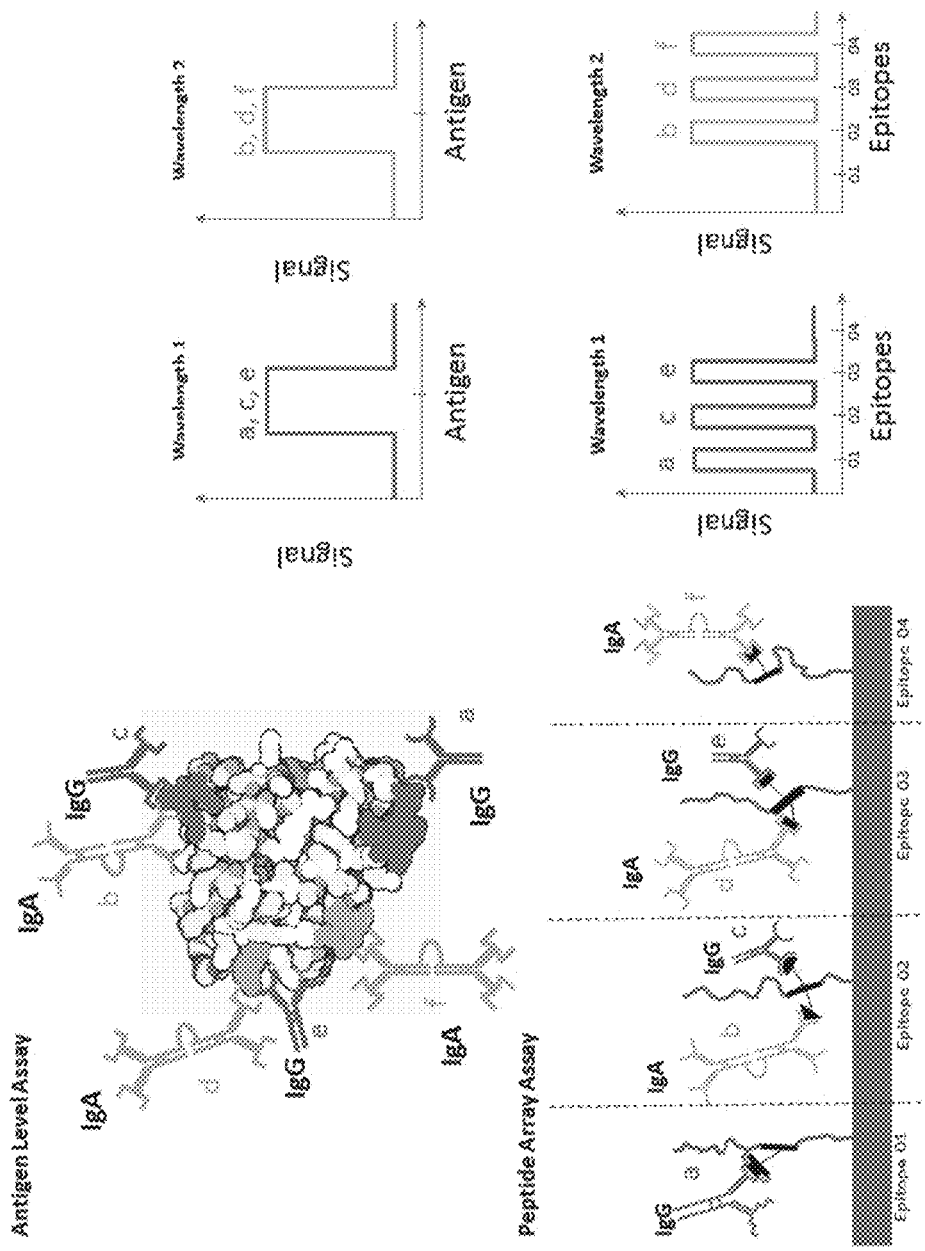
FIG. 14 diagrams the comparison between an antigen-based assay and a peptide array-based assay.
Figure 15:
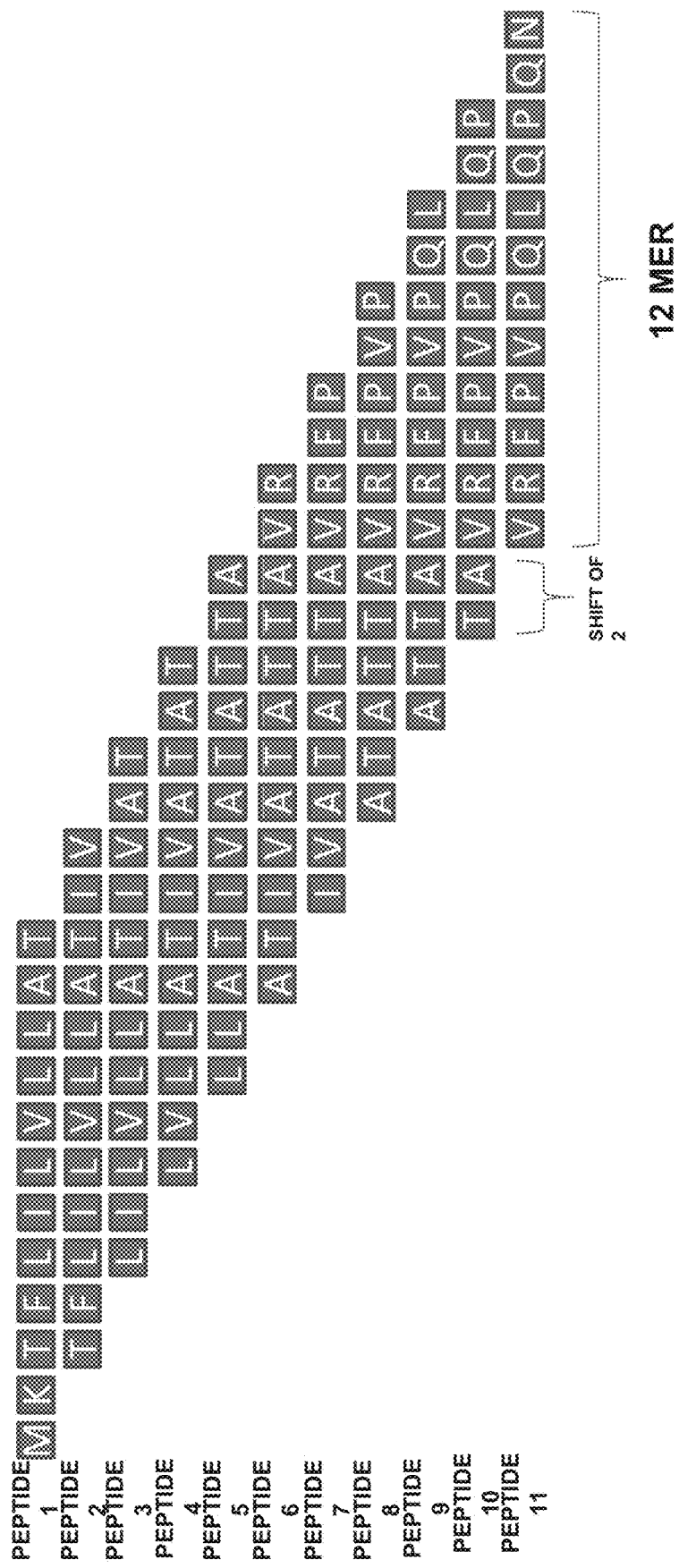
FIG. 15 outlines a method of splitting a protein of known sequence into overlapping peptide subsequences (SEQ ID NOS: 38-49, respectively, in order of appearance).

In this example, a known protein (e.g., an antigen) is represented on the array as a set of overlapping peptides. A sample obtained from a subject (in this example, serum) is assayed on the chip to identify the peptides bound by antibodies present in the sample. The pattern of antibody binding can be analyzed to define the epitopes recognized by the subject's antibodies, and optionally identify the classes of the bound antibodies. See FIG. 14. In this representative example, the protein alpha gliadin was split into overlapping peptide sequences each having a length of 12 amino acids as shown in FIG. 15. The overlapping frame size shown in FIG. 15 was chosen as 2. As this example is representative, only the first 29 amino acids of the entire alpha gliadin protein are shown. This example is representative of array features which comprise a plurality of distinct, nested, overlapping peptide chains comprising subsequences derived from a source protein having a known sequence.

The overlapping peptide sequences described above were then used in the construction of a library for a peptide array.

Example 11: Identification of a Periphilin-1 Subsequence

This example describes a method for determining the immunoactive regions of an whole known antigen and using the immunoactive region(s) to create a set of peptides very specific to the antigen-subsequences pathologically related to a given disease; thereby reducing the number of peptide sequences needed to represent the whole known antigen an a given array.

Immunological binding assays were performed on an array produced using the materials and methods described in the Examples above. The array included the overlapping peptide sequences shown in FIG. 17. The samples that were used to run the assays included clinically proven celiac positive samples.

Figure 17:
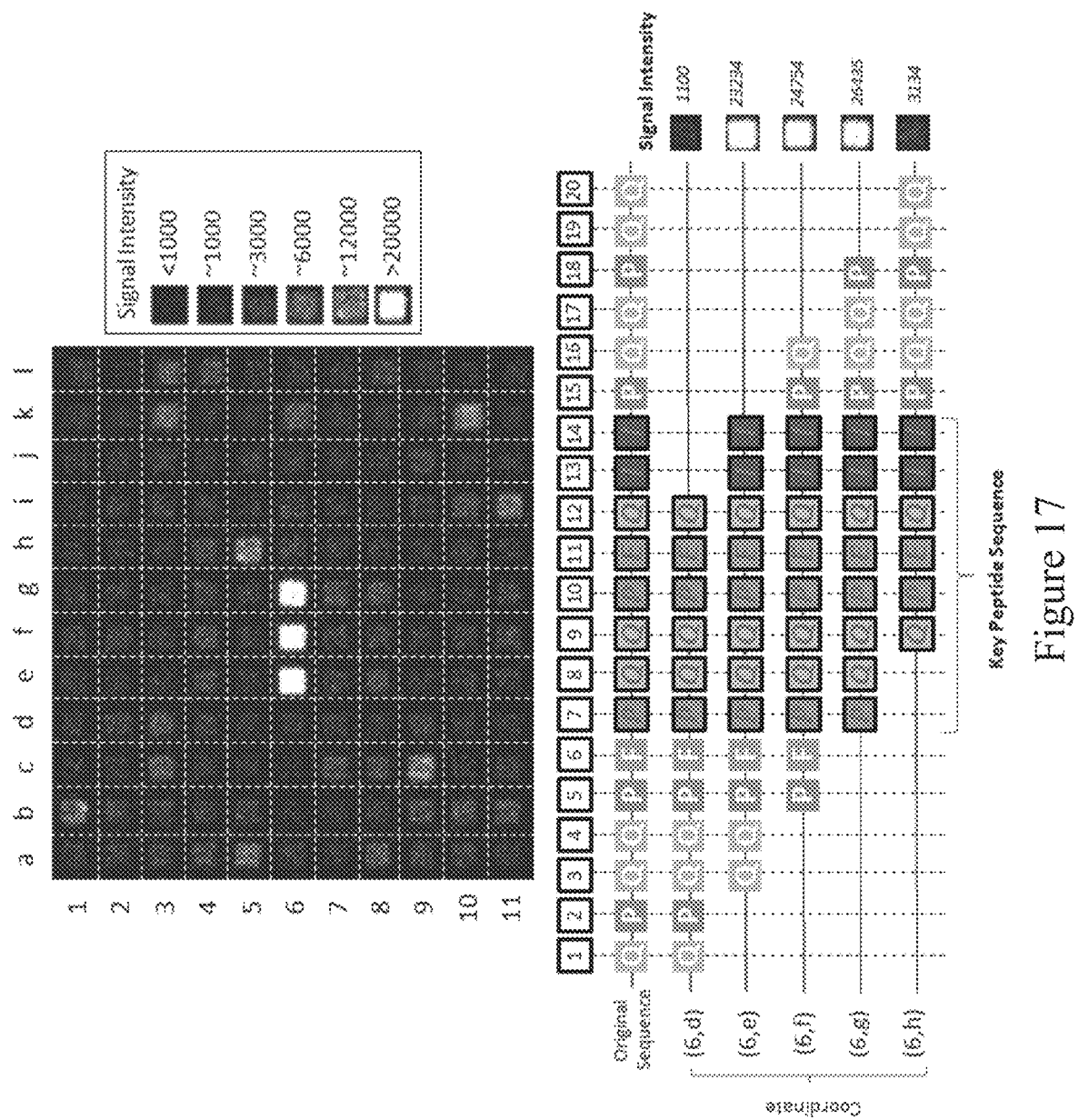
FIG. 17 describes a method of determining the immunoactive regions of a whole antigen (Periphilin-1) using a peptide array having subsequences (SEQ ID NOS: 54-59, respectively, in order of appearance) derived from the whole antigen.

The immunoactive regions of Periphilin-1 were determined. With reference to FIG. 17, the microarray substrate including the Periphilin-1 sequence split into 12 amino acid length peptide sequences is shown. The scanned immunoassay binding data shows the subsequence(s) that have substantial levels of labeled antibodies bound and the subsequence(s) that do not have substantial levels of antibodies bound. "Substantial levels" refers to binding associated with signals that are significantly above background. Determination of background noise, background subtraction, and identification of signals that exceed background noise routine and well within the level of ordinary skill in the microarray binding arts. In this example, the mean background signal intensity was estimated to be 400 and signals were determined to be significant when they exceeded background by a factor of 50. As the entire length of the Periphilin-1 protein sequence was spanned as overlapping peptides (subsequences), the key subsequence for antibody binding was identified as: PQQPEQII (SEQ ID NO: 23), i.e., the contiguous subsequence common to the sequences found at array addresses 6,e through 6,g. See FIG. 17.

Example 12: Method of Identifying Epitope and Antigenic Sequences Related to Celiac Disorder Determining Celiac Related Immunodominant Peptide Sequences In this example, we determined a set of peptide sequences that interact with immune regulatory molecules (e.g., epitopes) and are related to celiac disorder. This set of peptides was determined after two rounds of screening with celiac samples. The first round of screening was done by generating a peptide array comprising peptide subsequences tiled from celiac related proteins. We tiled related prolamins including all gliadins, secalins, hordeins and savinas according to the schematic shown in FIG. 15 and described in Example 10 with each overlapping peptide sequence having a length of up to 12 amino acids. The tiled sequences were also synthesized so that glutamine is replaced by glutamic acid for each possible iteration to mimic sequences present if the glutamine residue is deamidated to form a glutamic acid residue. For example, the sequence "AAIQTFQNTYQV" (SEQ ID NO: 24) was also present as a sequence where glutamine is replaced by glutamic acid in each possible iteration, i.e., "AAIETFQNTYQV" (SEQ ID NO 25), "AAIQTFENTYQV" (SEQ ID NO 26), "AAIQTFQNTYEV" (SEQ ID NO 27), "AAIETFENTYQV" (SEQ ID NO: 28), "AAIQTFENTYEV" (SEQ ID NO: 29), "AAIETFQNTYEV" (SEQ ID NO: 30), and "AAIETFENTYEV" (SEQ ID NO: 31). An example of the deamidation (e.g., the substitution of glutamine with glutamic acid) of alpha gliadin peptide fragments is shown in FIG. 16.

Celiac samples were obtained from ARUP Laboratories. This sample set included 20 Celiac positive and 40 Celiac negative samples.

As shown in FIG. 3, our peptide arrays identified three types of peptides that bind to immune-related molecules associated with celiac disorder: T peptides, B peptides, and C peptides. T peptides are the peptides that induce energy by the immature antigen presenting cells or by stimulating the regulatory T cells. B peptides are used to diagnose and identify the severity of the disease. C peptides are inflammation binding peptides and are useful in determining the disease state and severity. C peptides also increase the sensitivity of the disease diagnosis. The method used to identify each is described in more detail below.

Human Leukocyte Antigen (HLA) Assay (T Peptides)

T peptides were identified from the following HLA assay for each sample.

A peptide array comprising peptide fragment sequences of related prolamins including all gliadins, secalins, hordeins and savinas, as described above, were synthesized on the surface of the array made according to methods of Example(s) 1-7. A reduction reaction was performed to remove the disulfide bonds that exist between cysteine residues. This reduction reaction was not performed when epitopes involving cyclic peptides based on cysteine bonds are needed. Dithiothreitol was prepared in a concentration of 0.1 g per 20 mL PBS-Tween 20 (i.e., PBST). The peptide microarray (herein referred to as the peptide chip) was immersed in the DTT solution and placed in a nitrogen atmosphere at a pressure of 40 Pa at room temperature for 1 hour. The peptide chip was washed by spinning it immersed in PBST for 5 minutes. This procedure is repeated three times. The peptide chip was then washed by spinning it while immersed in methanol for 5 minutes. The chip was then further washed while immersed in PBST buffer by spinning for 5 minutes at 100 rpm.

The peptide fragments synthesized on the peptide chip that are very reactive were blocked by immersing the chip in 5% bovine serum albumin in phosphate buffered saline along with superblock buffer by shaking at 50 rpm for 1 hour at 37° C. The peptide chip was then incubated with celiac-positive serum and then peptides bound to HLA molecules present in the serum were identified using a monoclonal antibody with binding specificity for HLA from a celiac-positive serum sample obtained from Bio-Serve. The celiac-positive serum sample was diluted to a concentration of 1 μg/ml in PBS containing 0.2% bovine serum albumin. The peptide chip was immersed in the diluted celiac-positive serum sample and incubated at 37° C. for 24 hours without shaking. The peptide chip was then washed by shaking it for 5 minutes at 100 rpm while immersed in PBS with Tween-20 (i.e., PBST). This procedure was repeated 3 times.

The peptide array was then analyzed to detect HLA/array peptide complexes using a labeled monoclonal antibody specific for HLA (monoclonal antibody obtained from Abcam). The labeled monoclonal antibody specific for the HLA was diluted in a solution of PBST to between 1 μg/ml and 5 μg/mL. The antibody solution was incubated with the chip for 1 hour at 37° C. to detect to the HLA monoclonal antibody/array peptide complexes that were formed. Afterwards, the chip was washed by immersing in PBST and spinning at 100 rpm for 5 minutes. This procedure was repeated thrice. The chip was washed by immersion in deionized water and spinning at 100 rpm for 5 minutes. This procedure was repeated thrice. The peptide array was then analyzed to detect HLA monoclonal antibody/array peptide complexes.

Antibody Assay (B Peptides)

B peptides were used to diagnose and identify the severity of the disease and were identified from the following antibody assay for each sample.

The antibody binding assay to identify B peptides was performed as follows using materials provided in Table 9:

A peptide array comprising peptide fragment sequences synthesized on the surface of the array was generated according to the methods described above. The peptide array was developed to test all 12 mer sequences from alpha-gliadin, including sequences where glutamine was substituted with glutamate, as described above (see, e.g., FIGS. 15 and 16). A reduction reaction was performed to remove the disulfide bonds that exist between cysteine residues. This reaction was not performed when epitopes involving cyclic peptides based on cysteine bonds are needed. Dithiothreitol was prepared in a concentration of 0.1 g per 20 mL PBS-Tween (PBST). The peptide microarray (herein referred to as the peptide chip) was immersed in the DTT solution and placed in a nitrogen atmosphere at a pressure of 40 Pa at room temperature for 1 hour. The peptide chip was washed by spinning it immersed in PBST for 5 minutes. This procedure was repeated three times. The peptide chip was then washed by spinning it while immersed in methanol for 5 minutes. The chip was then further washed while immersed in TBS buffer by spinning for 5 minutes at 100 rpm.

The peptide fragments that are very reactive were blocked by immersing the chip in 5% bovine serum albumin in phosphate buffered saline along with superblock buffer by shaking at 50 rpm for 1 hour at 37° C.

The chip was then incubated with a celiac positive sample. The sample dilutions varied according to the sample tested. Serum was normally diluted 1:100 however this may vary depending on the concentration of antibody as known to one skilled in the art. The serum was diluted in 1% BSA in solution with PBST. The chip was immersed in the diluted sample and was incubated at 37° C. for one hour without shaking.

The chip was then washed with PBST by immersing and shaking it for 5 minutes at 100 rpm. This procedure was repeated 3 times.

Secondary antibody was used to detect to the primary antibodies. Primary antibodies include antibodies of type IgG, IgA, IgM, IgD, IgE and their subtypes present in sample from an individual/subject. The secondary antibody was diluted 1:1000 in PBST and was incubated with the peptide chip for 1 hour at 37° C. in the dark. Afterwards, the chip was washed by immersion in PBST and spinning at 100 rpm for 5 minutes. This procedure was repeated thrice. The chip was washed by immersion in deionized water and spinning at 100 rpm for 5 minutes. This procedure was repeated thrice.

The peptide array was then analyzed to detect antibody/peptide complexes.

TABLE 9

Materials used in peptide array screening assays

| No. | Chemical | Vendor | Catalogue No. |
|---|---|---|---|
| 1 | Superblock blocking buffer | VWR | PI37515 |
| 2 | TBS Buffer | VWR | 97064-338 |
| 3 | PBS with tween 20 (PBST) | VWR | 95059-258 |
| 4 | DTT | SIGMA ALDRICH | D9779-10G |
| 5 | 10% BSA | VWR | 37525, 82022-636 |

| No. | Name | Vendor | Catalogue No. |
|---|---|---|---|
| | Antibodies | | |
| 1 | Alexa Fluor 488 Goat XMO IgG | Lifetech | A11001 |
| 2 | Alexa Fluor 488 Goat XHU IgG | Lifetech | A11013 |
| 3 | Alexa Fluor 647 Goat XHU IgA | Jackson Immuno Research | 109-606-011 |
| | Monoclonal Antibodies | | |
| 1 | Anti Alpha Tubulin AALEKD | ABCAM | AB7291 |
| 2 | Anti IL2 KPLEEVENL | ABCAM | AB35977 |
| 3 | Anti HA YPYDVEPDYA | ABCAM | AB130275 |
| 4 | RHSVV | ABCAM | AB26 |
| 5 | SPDDIEQWFT | ABCAM | AB28 |
| 6 | LKWLDSFTEQ | ABCAM | AB1101 |

Celiac positive samples were assayed for antibody binding to the alpha-gliadin peptide array described earlier in this Example. Celiac positive samples and controls were obtained from various sources including Bio-Serve and Bioreclamation.

The threshold values for negative binding, a weakly positive sequence, and a strongly positive celiac antibody binding 12-mer sequences were established as follows:
    <10,000=negative
    10,000-20,000=weakly positive
    >20,000=strongly positive Bioinformatic Methods for Identifying Highly Informative Peptides A set of 12-mer sequences generating weakly or strongly positive binding signals to celiac positive samples was compiled (see, e.g., Table A in Appendix A of U.S. Provisional Application No. 61/761,347, incorporated herein by reference). Using a computer programmed to undertake sequence analysis, subsequences present within this set of 12-mer sequences were determined using a series of sliding windows having a minimum length of 3 amino acids and maximum length of 11 amino acids. A list of subsequences was thus generated and stored in computer memory. The number of occurrences of each subsequence in the set of 12-mer sequences was next determined using software that checked for the occurrence of each subsequence within each of the 12-mers comprising the set of 12-mer sequences. The number of occurrences were tabulated, and the top 9-most frequently occurring subsequences were identified. We hypothesized that these subsequences were likely to represent highly informative sequences that would be useful for generating synthetic peptides that could be used to specifically identify celiac samples. For additional methodology details, see, e.g., Example 11 and FIG. 17).

The tabulated subsequence results obtained from IgA binding studies using celiac positive samples are provided, e.g., in Table B in Appendix A of U.S. Provisional Application No. 61/761,347, incorporated herein by reference. A multiplex assay was used to additionally detect binding affinity to IgG antibodies. The tabulated subsequence results obtained from IgG binding studies using celiac positive samples are provided in, e.g., Table C in Appendix A of U.S. Provisional Application No. 61/761,347, incorporated herein by reference).

It was determined that the polydiversity in the antibody is a mark of severity of the disease. The key immune dominant subsequence (e.g., epitope) that simulates antibody response amongst celiac positive subjects was found to be the peptide sequence: "QPEQPF" (SEQ ID NO: 1). However, not all celiac positive subjects showed significant binding to this 6 mer epitope sequence. Other amino acid subsequences were identified that play a key role in determining the diversity of subtypes amongst patients having celiac disease.

The 9 3-mers with the highest score were combined in each possible iteration of 2 3-mers to form 81 6 mer sequences. (FIGS. 18 and 19) with the N-term peptides listed in the first column, and the C-term peptides listed in the first row. The set of 6 mer sequences was used to form a second set of sequences which are more potent than the original deamidated sequences and was plotted using same procedure described above. The sequence QPE-QPF (SEQ ID NO: 1) was found to generate sample binding hits of 91.78% for the celiac-positive serum sample (see FIG. 18, Row % QPE, Column QPF). Results are shown in FIG. 18 for IgA binding to peptides from a celiac-positive sample, and in FIG. 19 for IgG binding to peptides from the celiac-positive serum sample. These peptides were shown to not be recognized by celiac-negative controls, or from positive samples from other autoimmune diseases, as described below.

These sequences were compared against other diseases—40 samples Rheumatoid arthritis from Bio-Serve, 20 samples Crohns disease from Bioreclamation, 20 samples Ulcerative Colitis from Bio-Serve, 20 samples Multiple Sclerosis from Bio-Serve, 20 samples Gastroparesis from Bio-Serve and 20 samples Systemic Lupus from Bio-Serve. None of these samples had antibodies against celiac sequences shown in FIGS. 18 and 19.

Antibodies against specific drugs or therapeutics can be captured using this platform hence detecting side effects.

Cytokine Inflammation Assay (C Peptides):

Inflammation binding peptides (e.g., cytokines, TNF) are highly useful in determining the disease state and severity but also increases the sensitivity of disease diagnosis. Another important aspect of the C peptides is that the response to medication can be tracked for inflammatory response. This along with the B peptides help in identifying the refractory celiac disease. The C peptides can be used in designing monoclonals that could serve as anti inflammatories. C peptides were identified from the following inflammatory assay performed on a peptide chip.

Serum from celiac samples was screened for the presence of inflammation using the peptide chip described above. A peptide array comprising peptide fragment sequences synthesized on the surface of the peptide array was generated according to the methods described above. A reduction reaction was performed to remove the disulfide bonds that exist between cysteine residues. This reaction was not performed when epitopes involving cyclic peptides based on cysteine bonds are needed. Dithiothreitol was prepared in a concentration of 0.1 g per 20 mL PBS-Tween (PBST). The peptide microarray (herein referred to as the peptide chip) was immersed in the DTT solution and placed in a nitrogen atmosphere at a pressure of 40 Pa at room temperature for 1 hour. The peptide chip was washed by spinning it immersed in PBST for 5 minutes. This procedure was repeated three times. The peptide chip was then washed by spinning it while immersed in methanol for 5 minutes. The chip was then further washed while immersed in TBS buffer by spinning for 5 minutes at 100 rpm.

The peptide fragments synthesized on the peptide chip that are very reactive were blocked by immersing the chip in 5% bovine serum albumin in phosphate buffered saline along with superblock buffer and shaking at 50 rpm for 1 hour at 37° C. The peptide chip was then incubated with the serum diluted 1:100 in PBS. The peptide chip was immersed in the diluted sample and was incubated at 37° C. for 24 hours without shaking.

The peptide chip was then washed by shaking it for 5 minutes at 100 rpm while immersed in PBST. This procedure was repeated 3 times.

A labeled monoclonal antibody was used to detect TNF binding. The dilution of the monoclonal antibody can be from 1 µg/mL to 5 µg/mL. The antibody solution was incubated with the chip for 1 hour at 37° C. to detect to the TNF/peptide complexes that were formed. Afterwards, the chip was washed by immersion in PBST and spinning at 100 rpm for 5 minutes. This procedure was repeated thrice. The chip was washed by immersion in deionized water and spinning at 100 rpm for 5 mins. This procedure was repeated thrice.

The peptide array was then analyzed to detect TNF/peptide complexes. The serum may be from a human or any animal.

Celiac Related Infections Assay:

This example provides a method of determining infections related to celiac disease patients. Antigenic peptides from bacteria, virus, fungus, parasites are tiled on the platform as 12-mer peptide sequences and an antibody assay is performed as explained above. Table E (Appendix A) provides the list of peptides, which could provide molecular mimicry of gluten peptides, that have antibodies against common in patients with celiac disorder. An antibody assay as described in the "B peptides" assay above was performed on the peptide chip having peptides from Table E. Epitope subsequence that bind antibodies in a patient having celiac disease are determined from the results of this assay.

Example 13: Method of Diagnosing Patients with Celiac Disorder Using a Peptide Array Celiac Disease Detection and Subtype Diagnosis with a Single Assay:

This embodiment provides an assay protocol where in the above mentioned antibody and cytokine assays can be performed as one single assay comprising both B peptides and C peptides identified in the assays described above. This assay protocol reduces serum usage and increases the sensitivity of diagnosis.

A peptide array comprising B peptide and C peptide fragment sequences (e.g., epitopes) synthesized on the surface of the peptide array according to methods 1-7 is provided. A reduction reaction is performed to remove the disulfide bonds that exist between cysteine residues. This reaction is not performed when epitopes involving cyclic peptides based on cysteine bonds are needed. Dithiothreitol is prepared in a concentration of 0.1 g per 20 mL PBS-Tween (PBST). The peptide microarray (herein referred to as the peptide chip) is immersed in the DTT solution and placed in a nitrogen atmosphere at a pressure of 40 Pa at room temperature for 1 hour. The peptide chip is washed by spinning it immersed in PBST for 5 minutes. This procedure is repeated three times. The peptide chip is then washed by spinning it while immersed in methanol for 5 minutes. The chip is then further washed while immersed in TBS buffer by spinning for 5 minutes at 100 rpm.

The peptide fragments synthesized on the peptide chip that are very reactive are blocked by immersing the chip in 5% bovine serum albumin in phosphate buffered saline along with superblock buffer by shaking at 50 rpm for 1 hour at 37° C. The peptide chip is then incubated with the serum diluted 1:100 in PBS. The peptide chip is immersed in the diluted sample and is incubated at 37° C. for 24 hours without shaking.

The peptide chip is then washed by shaking it for 5 minutes at 100 rpm while immersed in PBST. This procedure is repeated 3 times.

Secondary antibody is used to detect to the primary antibodies. Primary antibodies include antibodies of type IgG, IgA, IgM, IgD, IgE and their subtypes present in sample from an individual/subject. The secondary antibody is diluted 1:1000 in PBST and is incubated with the peptide chip for 1 hour at 37° C. in the dark. Afterwards, the chip is washed immersed in PBST by spinning at 100 rpm for 5 mins. This procedure is repeated thrice. The chip is washed immersed in deionized water by spinning at 100 rpm for 5 mins. This procedure is repeated thrice.

The peptide array is then analyzed to detect antibody/peptide complexes. The serum may be from a human or any animal.

Example 14: Method of Treating Patients with Celiac Disorder

A mouse model is built to test the use of T peptides discovered above as a therapeutic agent. The identified T peptides are mixed in a cocktail and administered to transgenic mice. The same peptide array platform described above is used to determine the cytokine profile and response to the peptides. IFN, IL-10 and TGF-B responses are measured after administering the peptide cocktails. IL-10 being anti-inflammatory suggests the presence of regulatory T cells in inducing T cell tolerance. A decrease in the IFN levels suggests an immune suppressive response. Hence the platform is used to identify highly specific immune suppressive peptide cocktails.

Example 15: Lithocell Process for Generating a Peptide Array

To generate the peptide array, we used a batch processing of a semiconductor manufacturing based coater/developer module in combination with the lithographic deep ultraviolet tool which enabled the process to be completely automated and hence increase throughput. The mass spectrometry data obtained from this method of peptide synthesis shows a single sharp peak as compared to the methods described in the literature which show several shallow peaks.

From the PCT application, FIG. 2 A through 2 G depict the process of manufacturing. All these manufacturing processes were performed in a combination of lithocell and bio chemistry cell. The systems were separated into two or three modules as following:

Standalone—Photo-exposure tool
Standalone—Photoresist coat module
Standalone—Biochemistry track module Any combination of above three were used to increase throughput using a batch or sequential mode processing.

Figure 20:
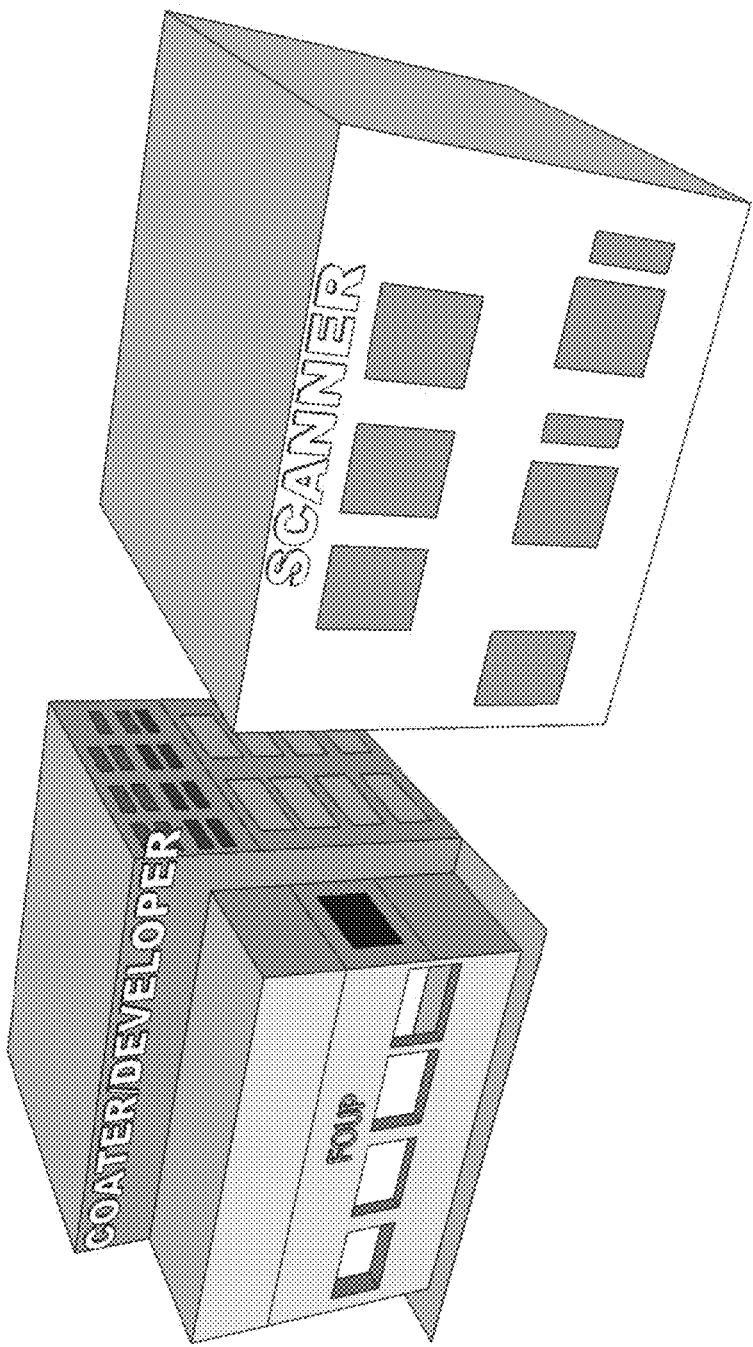
FIG. 20 depicts process flow for developing wafers in a connected coater/developer and litho cell.

This device provides a method of synthesizing biopolymers or biomolecules in a totally automated microarray synthesis tool which reduced the cycle time for doing one coupling reaction to less than 10 minutes. The entire cycle of steps as described in FIG. 2 were split into a biochemistry module process and a deprotection module process (FIG. 20). A biochemistry module process involved the coupling, coupling bake, coupling strip, capping, capping bake and the capping strip process. A deprotection module process included photoresist coating, resist pre bake, photo exposure, post exposure bake and photo resist strip. The time taken for a biochemistry module process was about 5 minutes and the time for the deprotection module process was also 5 minutes. Hence the overall time to complete one step in the sequence took less than 10 minutes.

The embodiments of the invention include a method of synthesizing peptide array using a microarray synthesizing cluster 1 million unique peptides per $cm^2$ to more than several billion unique peptides per $cm^2$ and more than 20K microarrays with 20 amino acids building block were produced in less than:

a. 5 days for 20mer peptide microarray in 24 hours per day synthesis with total of 400 amino acid coupling steps.
b. 10 days for 40mer peptide microarray in 24 hours per day synthesis with total of 800-amino acids coupling steps.
c. 15 days for 60mer peptides microarray in 24 hours per day synthesis with total of 1200 amino acids coupling steps.

Figure 21:
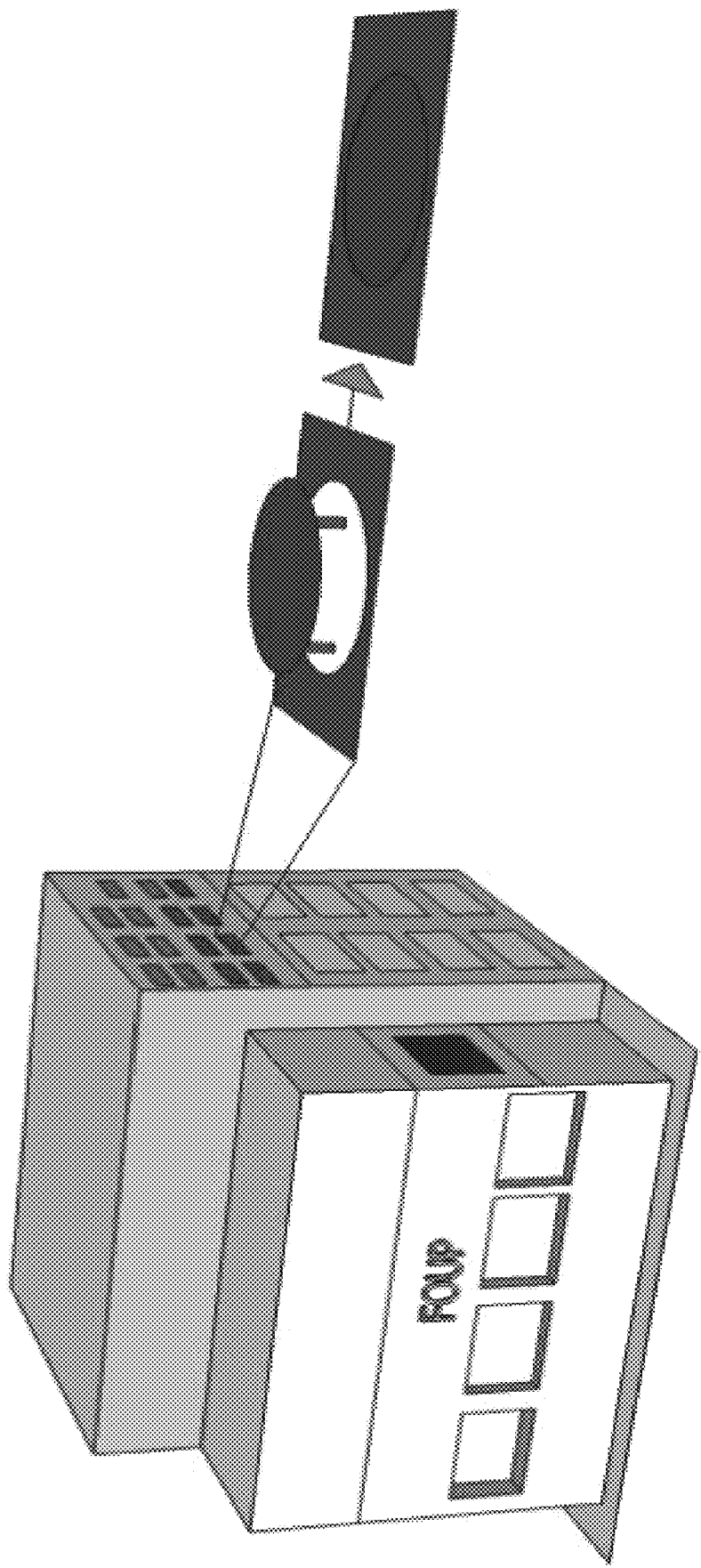
FIG. 21 shows the cooling step during wafer production according to the process flow.
Figure 22:
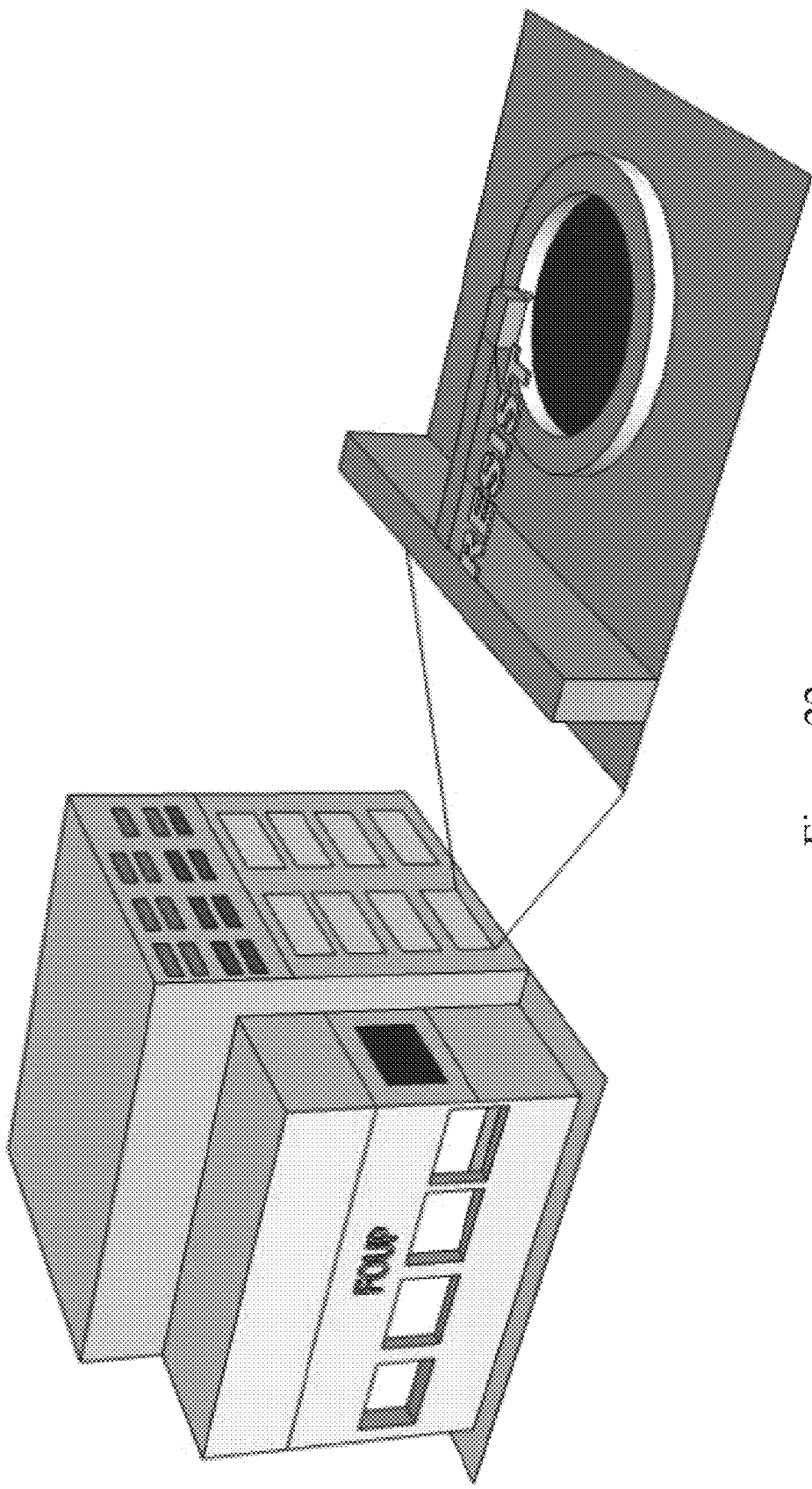
FIG. 22 depicts coating of a wafer with resist according to the process flow.

Referring to FIGS. 21 and 22, the wafers were cooled in a cool plate and then coated with photoresist.

Figure 23:
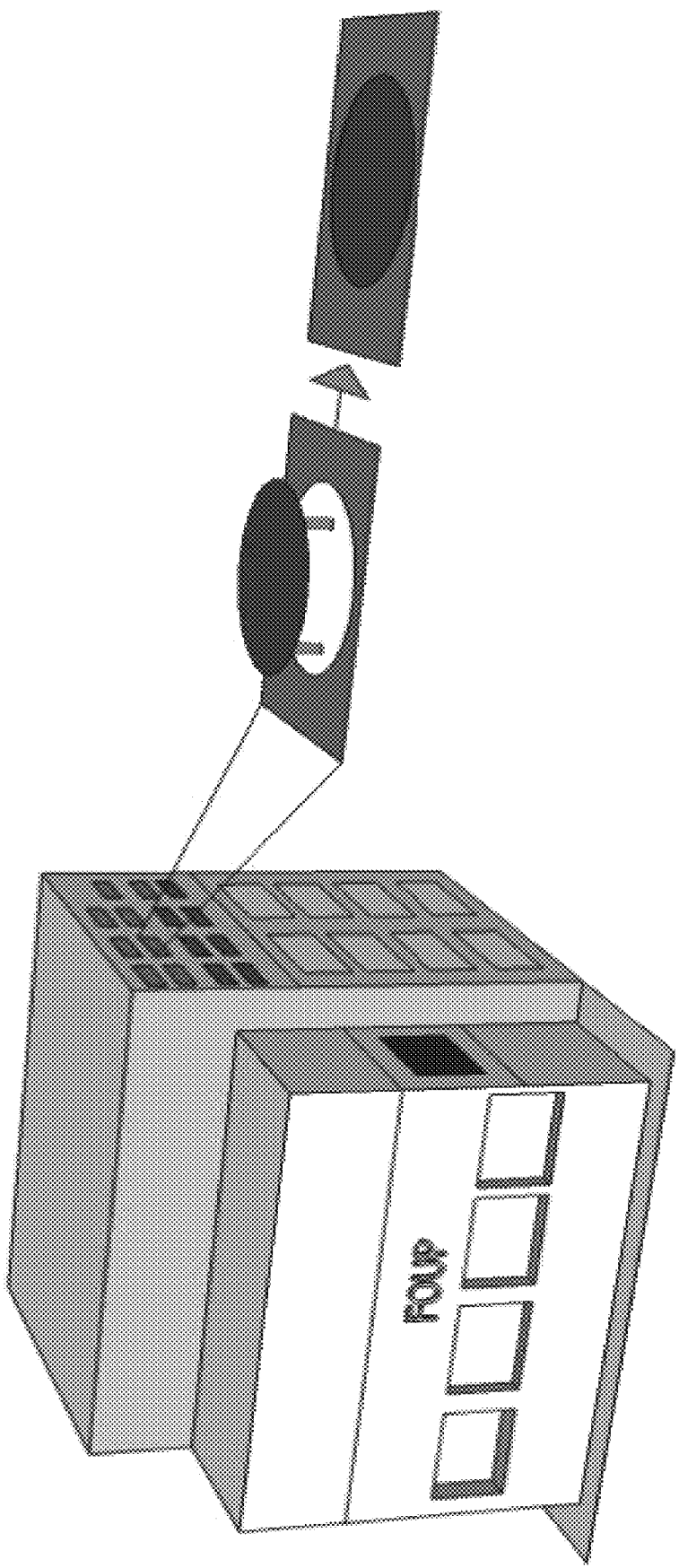
FIG. 23 depicts baking of the wafer after coating with resist according to the process flow.
Figure 24:
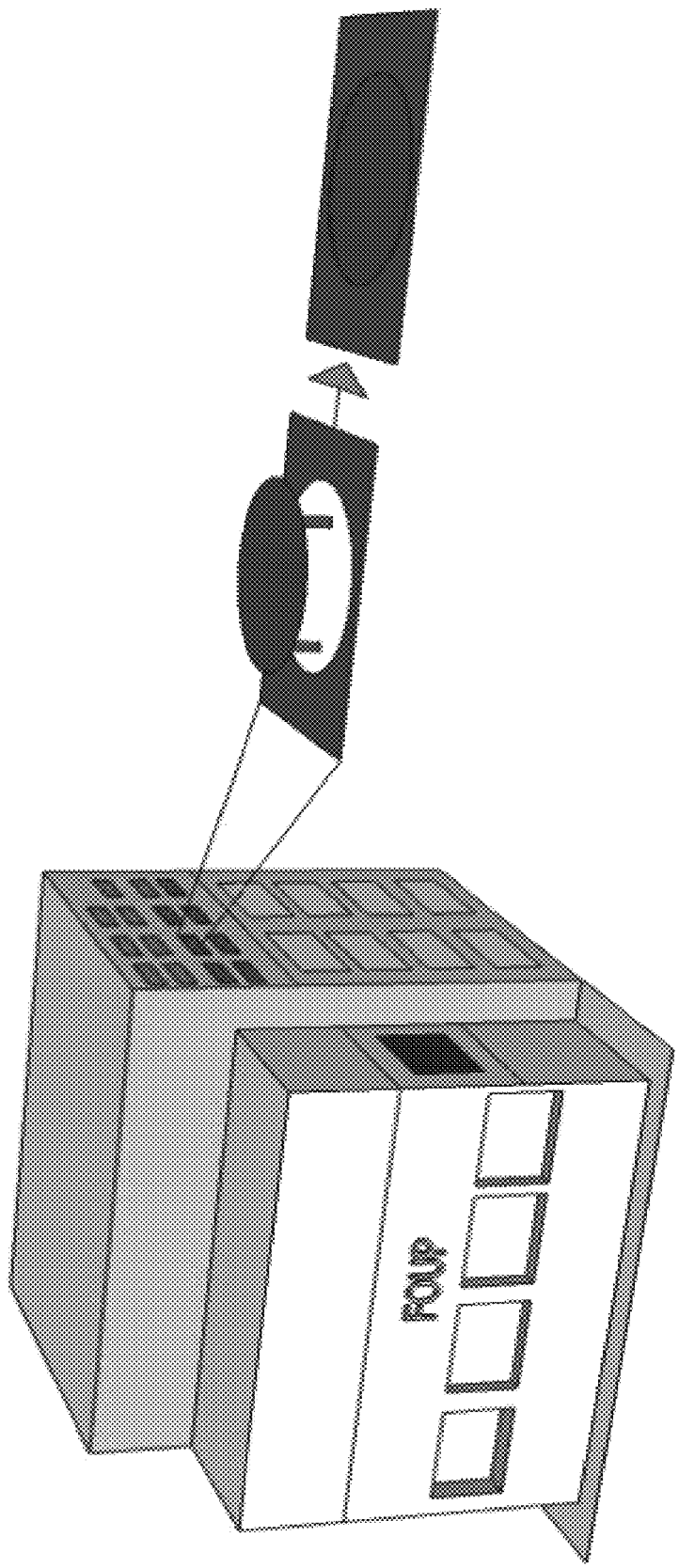
FIG. 24 depicts cooling of the wafer after baking according to the process flow.
Figure 25:
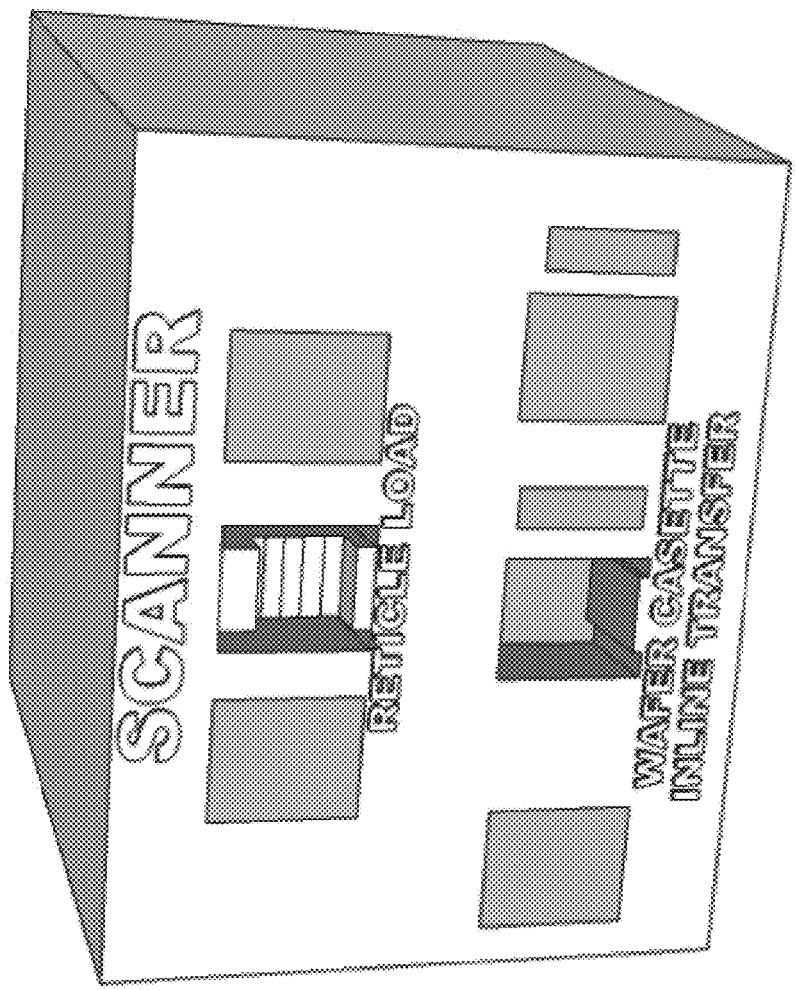
FIG. 25 depicts transfer of the wafers from the coater/developer machine to the scanner.

Referring to FIGS. 23, 24 and 25, the coated wafers were baked, cooled, and then moved inline to a deep ultraviolet exposure tool. (This is also shown in the process flow depicted in FIGS. 2A and 2B).

Figure 26:
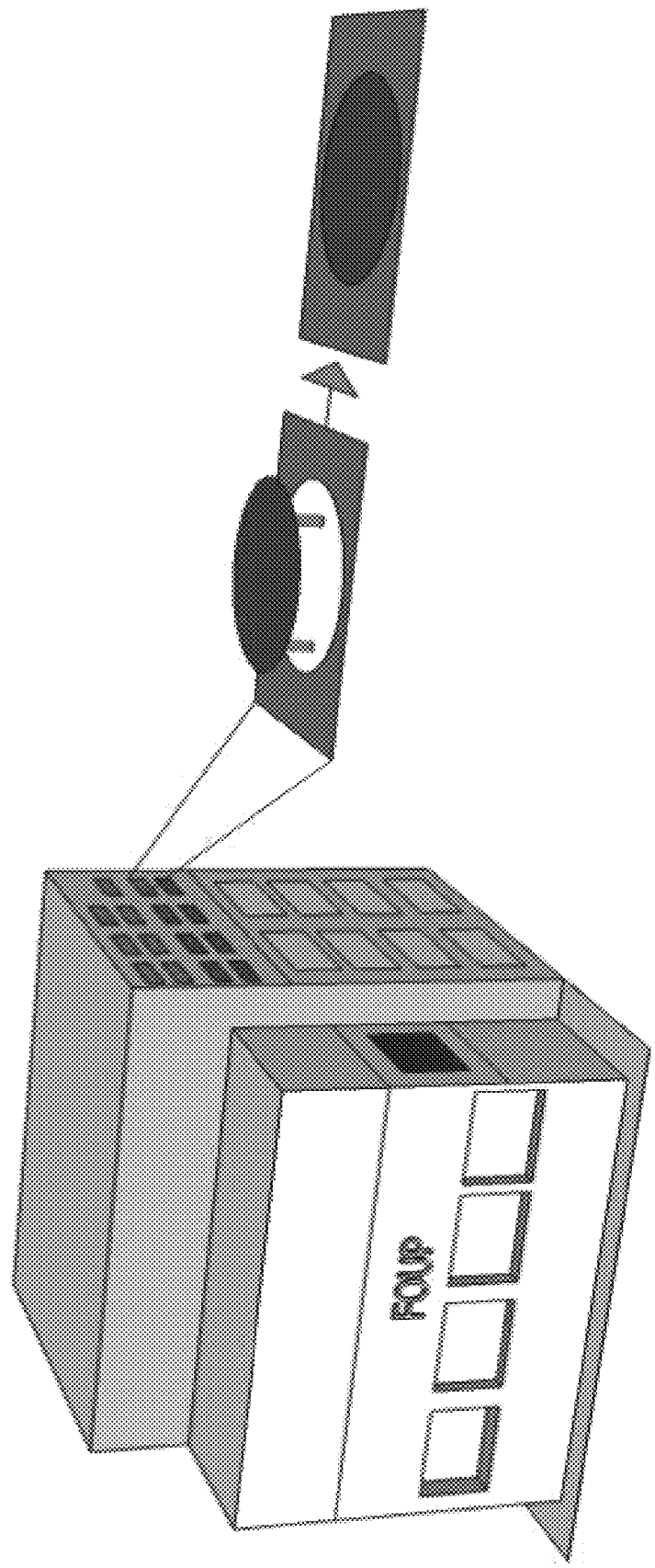
FIG. 26 depicts baking of the wafer according to the process flow.
Figure 27:
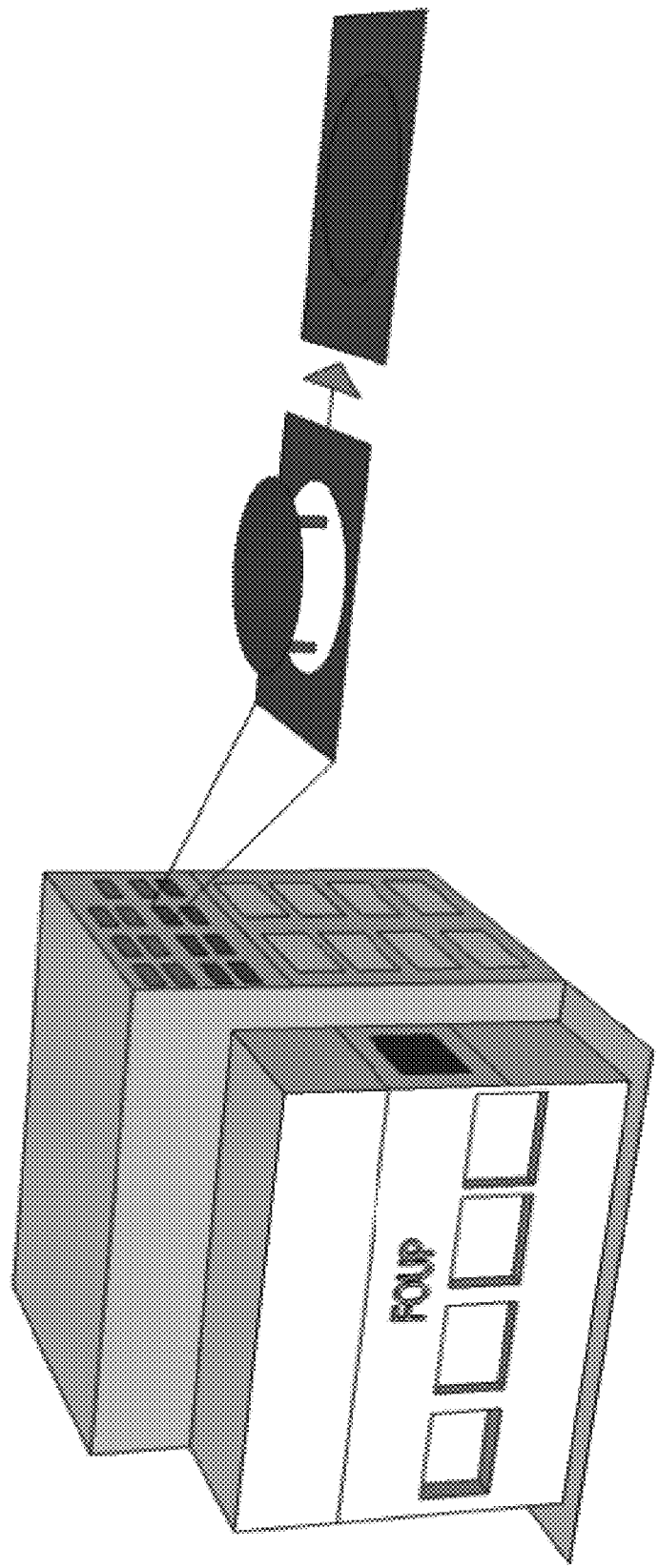
FIG. 27 depicts cooling of the wafer after baking according to the process flow.
Figure 28:
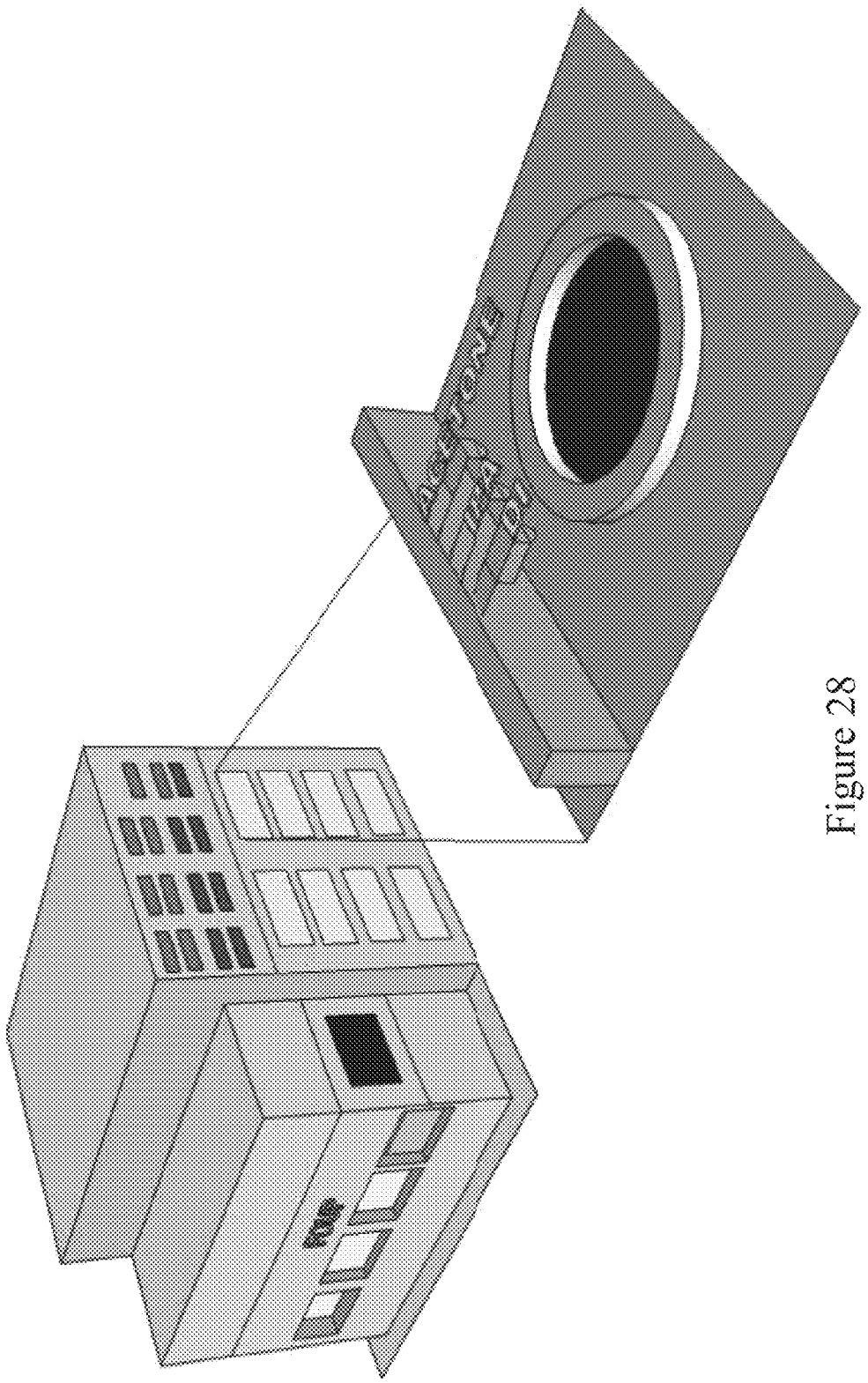
FIG. 28 depicts rinsing of the wafers with deionized water to remove the resist according to the process flow.

Referring to FIGS. 26, 27 and 28, the wafers are baked in a hot plate to enhance acid diffusion to the substrate. This does not act as a chemical amplification step as the acid generated is not amplified upon heating. Now the wafers were cooled and rinsed with DI water to strip the photoresist. (This is also shown in the process flow depicted in FIG. 2C).

Figure 35:
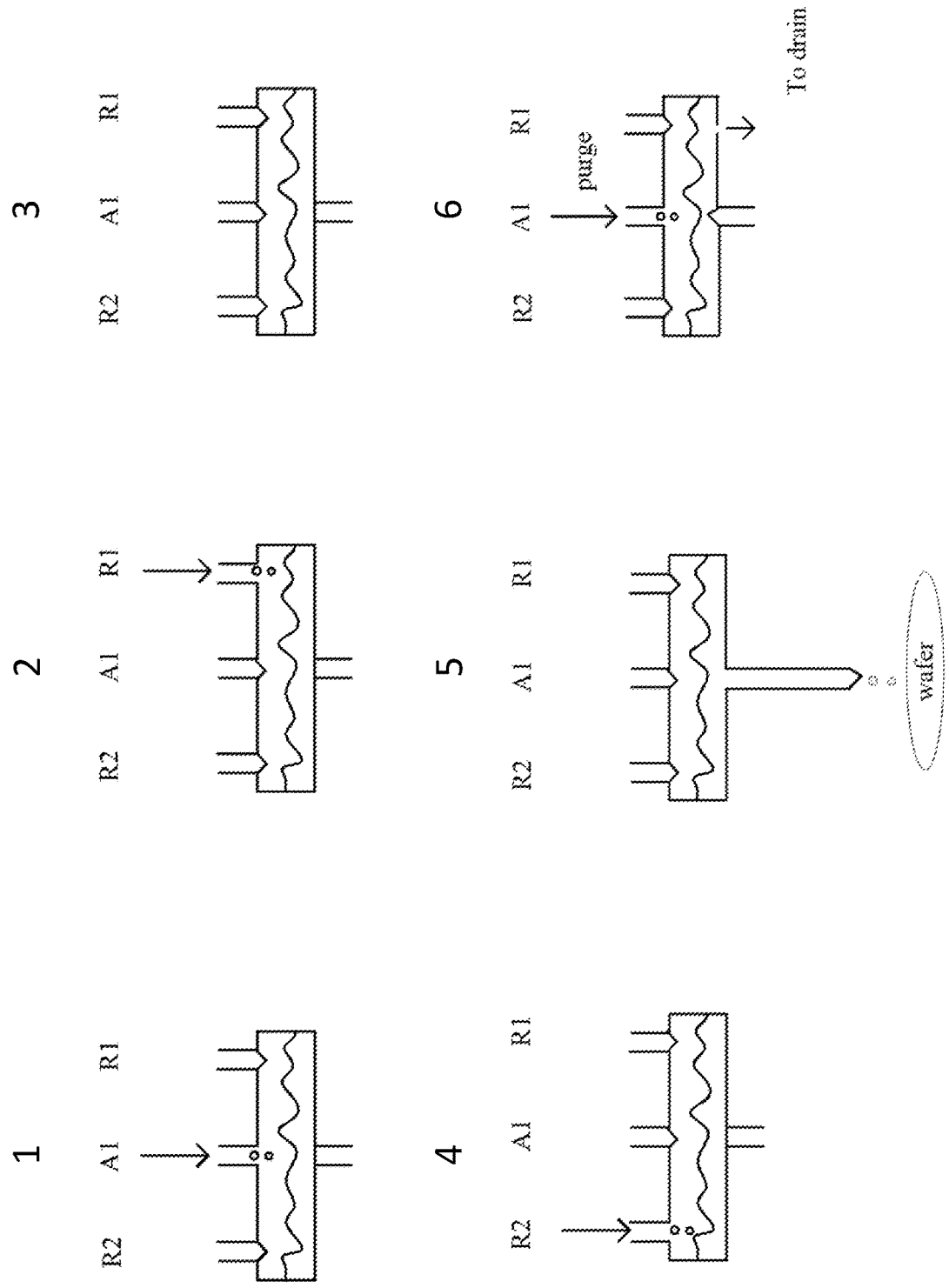
FIG. 35 depicts a diagram of steps to set up a lot of 25 wafers assuming 8 ml of AA1- AA20 per wafer.

Referring to FIGS. 29 and 30, one of the twenty amino acid coupling solutions, that were stored in Nowpak containers, were dispensed according to the following figures:

The following steps shown in FIG. 35 were followed to set up a lot of 25 wafers assuming 8 ml of AA1-AA20 per wafer:

Step 1: R1 stored reagent 1—4% by weight for each EDC and HonB dissolved in DI water. R2 stored reagent 2 DIEA. A1-A20 stored each of the naturally occurring amino acid solution. It contained premixed solutions of inert water soluble polymers (3% by weight PVP and 7% by weight PVA) dissolved in the ratio of 1:2.5 in deionized (DI) water which makes up about 10% by weight of the solution along with 2% by weight amino acid concentration. In this example, AA1 reservoir were filled with AA1 for 25*8=200 ml.

Step 2: Reagent 1 was added for 0.4*20=8 ml (0.4 ml per 10 ml of A1)

Step 3: The reservoir was heated from room temperature to 60° C. and maintained for 10 minutes starting at $t_0$.

Step 4: Heating was turned off and reagent 2 (0.4*20=8 mL) was added immediately (at $t_{10}$ min).

Step 5: At $T_{15}$ (5 minutes after reagent 2 is added and 15 minutes after T0) the mixture was dispensed onto the first wafer.

Step 6: After all 25 wafers, the reservoir was purged with A1.

This sequence of steps complete the process for one amino acid coupling.

Figure 31:
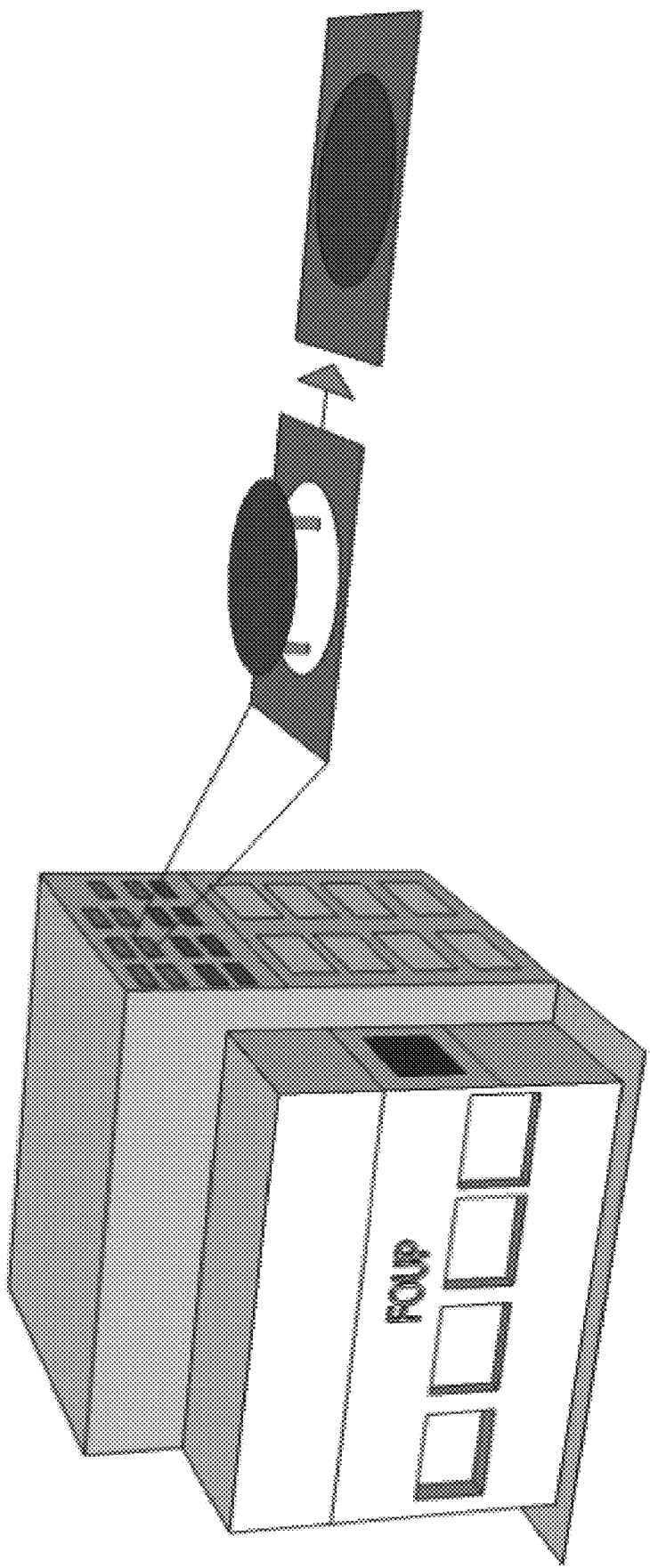
FIG. 31 depicts baking of the wafers after addition of the selected amino acid according to the process flow.
Figure 32:
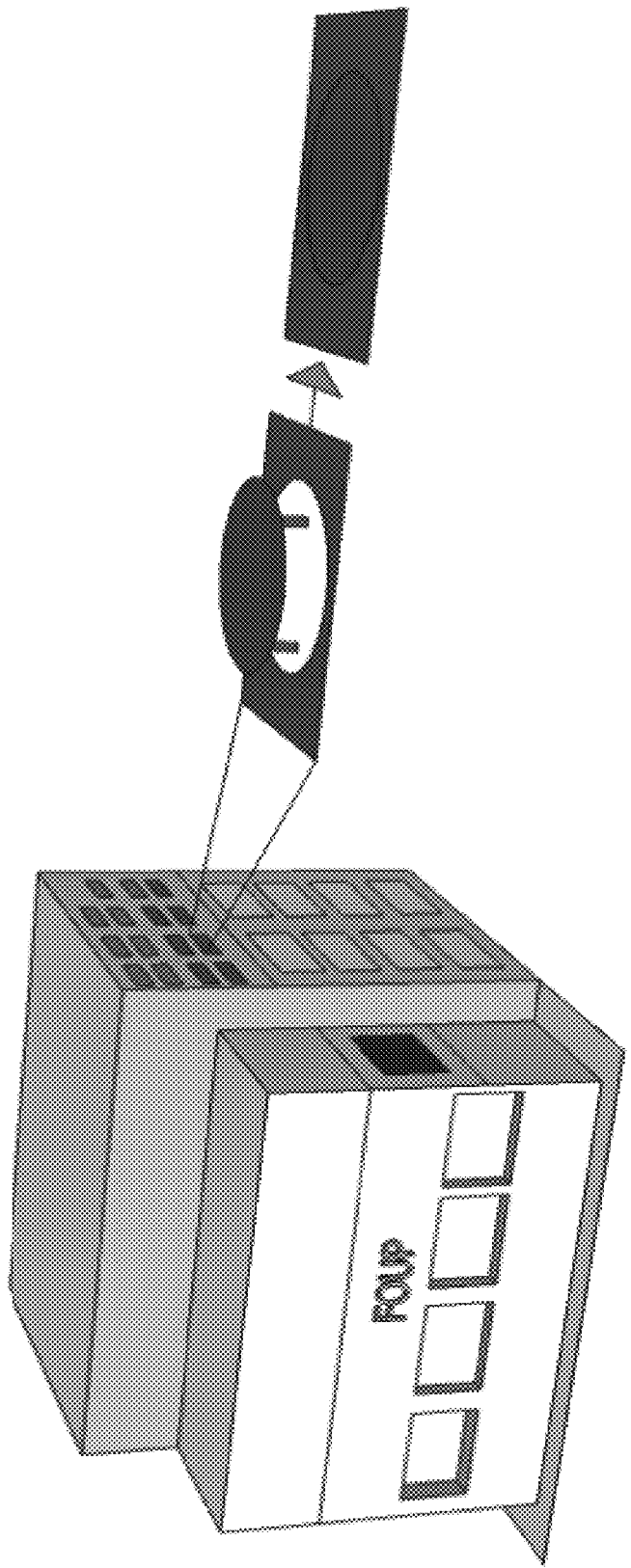
FIG. 32 depicts cooling of the wafer after baking according to the process flow.
Figure 33:
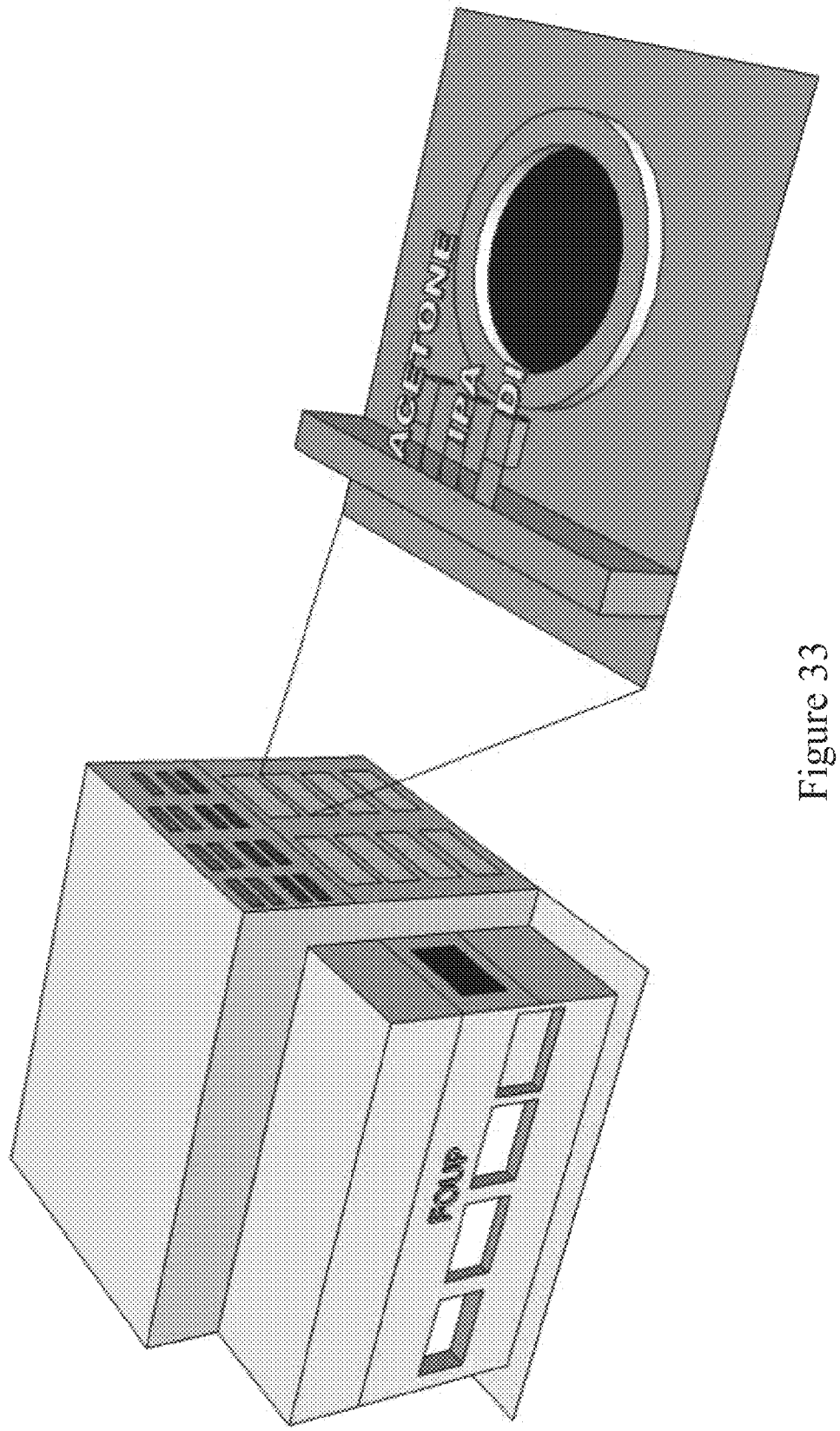
FIG. 33 depicts coating of the wafers with deionized wafer after cooling according to the process flow.

Referring to FIGS. 31-33, the wafers were then baked, cooled, and washed with DI water and the entire cycle was repeated for AA2 with a different photomask, continuing through all peptide reservoirs to complete the entire library of peptide array.

Example 16: Pillar Substrate Preparation

Figure 34:
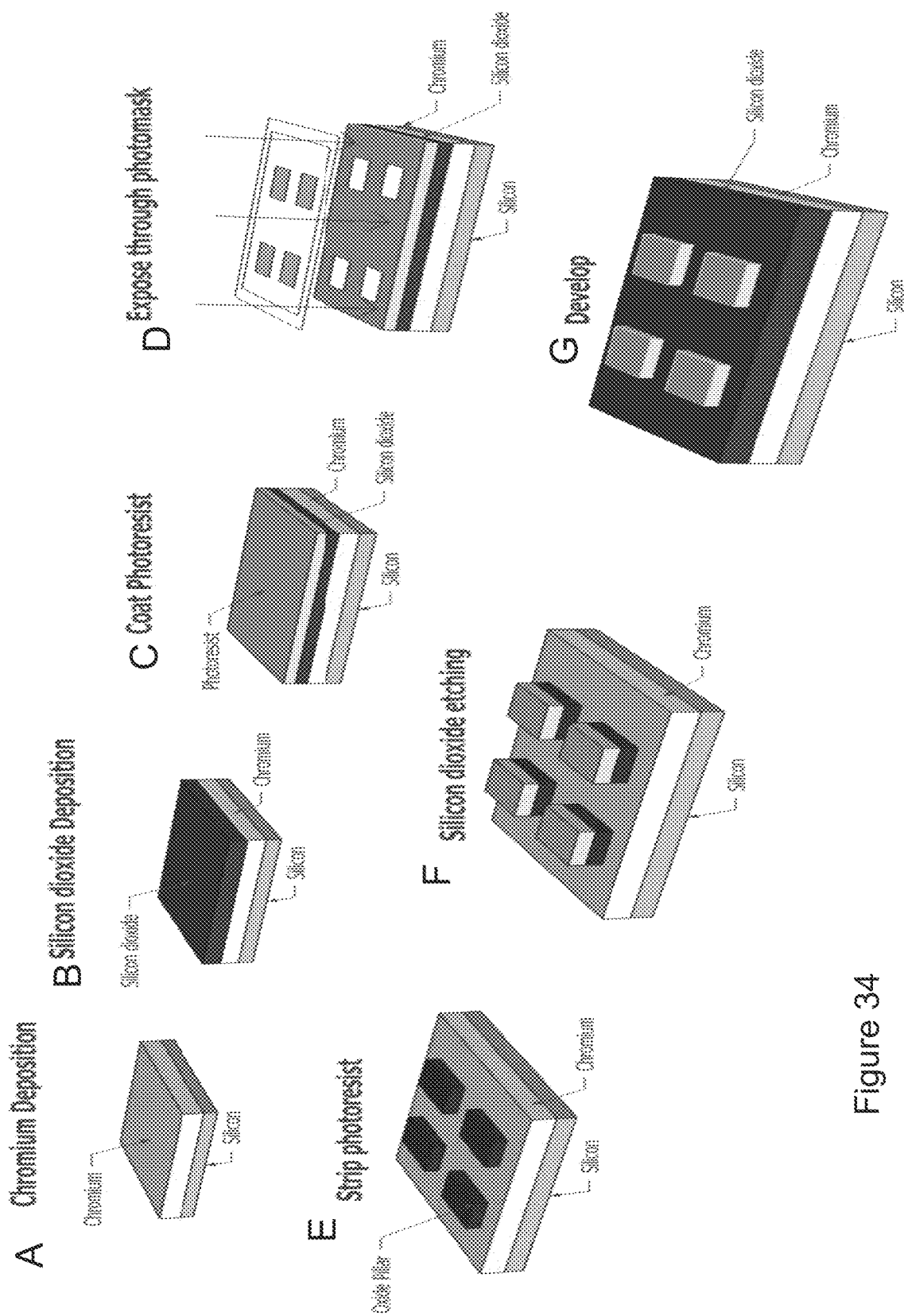
FIG. 34 depicts a step-flow diagram for substrate preparation.

Silicon wafers were obtained from University Wafers. Referring to FIG. 34A, a metal was deposited on the wafers. This metal was selected from chromium, titanium, or aluminum. The metals were deposited by a process called sputter deposition. Sputter deposition is a physical vapor deposition (PVD) method of depositing thin films by sputtering, that is ejecting, material from a "target," that is a source, which then deposits onto the wafers. The thickness of metal deposition was ensured to be at least 500 Å on top of the substrate.

Referring to FIG. 34B, silicon dioxide was deposited on the wafers. The oxide was deposited by a process called sputter deposition. Sputter deposition is a physical chemical vapor deposition (PECVD) method of depositing thin films by sputtering, that is ejecting, material from a "target," that is a source, which then deposits onto the wafers. The thickness of oxide deposition was ensured to be at least 500 Å on top of the substrate.

Referring to FIG. 34C, the first step in the preparation of a substrate was priming a starting wafer in order to promote good adhesion between a photoactive formulation (e.g., a photoresist) and a surface. Wafer cleaning was also performed, which included oxidation, oxide strip, and an ionic clean. (DI) water rinse was used to remove contaminants on the wafer surface. In wafer fabrication, silane deposition was used to promote the chemical adhesion of an organic compound (photoresist) to a non-organic substrate (wafer). The silane acts as a sort of "bridge," with properties bind to both the photoresist and wafer surface. Typically, hexamethyldisilizane (HMDS) was used. HMDS is an organosilicon compound that was applied on heated substrates in gaseous phase in a spray module or in liquid phase through puddle and spin in a developer module. This was followed by a bake step. In a puddle and spin method, HMDS was puddled onto the wafer for a specified time and then was spun and baked at temperatures of 110° C.-130° C. for 1-2 mins. In a spray module, vapors of HMDS were applied onto a heated wafer substrate at 200° C.-220° C. for 30 s-50 s.

Referring to FIG. 34C, after wafer priming, the wafers were coated with a deep ultra violet (DUV) photoresist in a photoresist coater module. Our DUV resist comprised polyhydroxystyrene-based polymers with a photoacid generator providing the solubility change. The DUV resist further comprised a photosensitizer. The matrix in the polymer comprised a protecting group for e.g., tboc attached to the end group.

The DUV resist was spin coated on the wafers in a photoresist coat module. This module comprised a vacuum chuck held inside a cup. The wafers were mechanically placed on the chuck by a robotic arm and then were spun at required speeds specified by the manufacturer to obtain the optimum thickness.

Referring to FIG. 34C, the wafers were pre-heated in a pre-heat module. The pre-heat module included a hot plate that can be set to required temperatures for the corresponding DUV resist as specified by the manufacturer. In cases for heating a batch of wafers, we used a microwave for heating.

Referring to FIG. 34D, the wafers were exposed in a deep ultra violet radiation exposure tool through patterned photo masks.

Referring to FIG. 34E, the wafers were heated in a post exposure bake module. This post exposure led to chemical amplification. The resist manufacturers provided the typical post exposure bake temperature and time for their corresponding product. When a wafer coated with a DUV photoresist was exposed to 248 nm light source through a reticle, an initial photoacid or photobase was generated. The exposed portion of the resist became soluble to the developer thereby enabling patterning of 0.25 micron dimensions. A post exposure bake module comprised a hot plate set to the required temperatures as specified by the manufacturer. The module comprised three vacuum pins on which the wafers were placed by a robotic arm.

Referring to FIG. 34E, the wafers were developed in a developer module. The developer module comprised a vacuum chuck that held wafers and pressurized nozzles that dispensed the developer solution on to the wafers. The dispense mode was either a puddle and spin mode or a spin and rinse mode. During the puddle and spin mode, the wafers remained stationery on the chuck for about 30 seconds to 1 minute when the developer solution was dispensed. This puddled the developer solution on top of the wafer. After one minute, the developer solution was spun away. During the spin and rinse mode, the developer solution was dispensed while the wafers were spun.

Referring to FIG. 34F, the oxide was etched away in those regions that are developed by means of a wet etch or a dry etch process. Etching is a process by which material is removed from the silicon substrate or from thin films on the substrate surface. When a mask layer is used to protect specific regions of the wafer surface, the goal of etching is to precisely remove the material, which is not covered by the mask. Normally, etching is classified into two types: dry etching and wet etching. Wet etching uses liquid chemicals, primarily acids to etch material, whereas dry etching uses gases in an excited state to etch material. These processes were run to achieve an etch depth of, e.g., 500 Å.

Referring to FIG. 34G, the wafers were submerged in an oxidizer solution overnight and then dipped in a Piranha solution for typically 1 hr. Piranha solution used was a 1:1 mixture of sulfuric acid and hydrogen peroxide. This solution was used to clean all the organic residues off the substrates. Since the mixture is a strong oxidizer, it removed most of the organic matter, and it hydroxylated most surfaces (i.e., add OH groups to the surface), making the surfaces hydrophilic. This process also included an additional step of plasma ashing.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A substrate coupled to a silicon wafer, comprising:
(1) a planar layer comprising chromium and having an upper surface and a lower surface;
(2) a plurality of pillars comprising silicon dioxide operatively coupled to the layer in positionally-defined locations, wherein each pillar has a planar surface extended from the layer, wherein the surface area of each pillar surface is at least 1 μm$^2$ and wherein the surface area of each pillar surface has a total area of less than 10,000 μm$^2$ and wherein the plurality of pillars are present at a density of greater than 10,000/cm$^2$, and wherein the distance between the surface of each pillar and the upper surface of the layer is between 1,000-5,000 angstroms, and wherein the distance between the surface of each pillar and the lower surface of the layer is 2,000-7,000 angstroms, and wherein the center of each pillar is at least 2,000 angstroms from the center of any other pillar, and
wherein a linker molecule having a protecting group is attached to the surface of at least one pillar, and wherein a water soluble polymer is in contact with the surface of at least one of said pillars; and
(3) a porous layer comprising dextran, said porous layer further comprising a plurality of unprotected carboxylic acid side groups, wherein said porous layer comprises pores from about 2 nm to 100 μm in diameter or a porosity of about 10-80%, and wherein said porous layer also comprises a thickness of about 0.01 μm to about 10,000 μm.

* * * * *